US012806136B2

(12) United States Patent
Quinci et al.

(10) Patent No.: US 12,806,136 B2
(45) **Date of Patent: *Nov. 24, 2026**

(54) IMPLANTABLE DEVICE FOR INTRATUMORALLY ADMINISTERING A THERAPEUTIC AGENT

(71) Applicant: Celanese EVA Performance Polymers LLC, Irving, TX (US)

(72) Inventors: Thomas Quinci, Oxford, OH (US); Brian Wilson, Deerfield, IL (US); Jeffrey Haley, Norwood, OH (US)

(73) Assignee: Celanese EVA Performance Polymers LLC, Irving, TX (US)

( * ) Notice: Subject to any disclaimer, the term of this patent is extended or adjusted under 35 U.S.C. 154(b) by 365 days.

This patent is subject to a terminal disclaimer.

(21) Appl. No.: 18/456,541

(22) Filed: Aug. 28, 2023

(65) Prior Publication Data

US 2024/0091140 A1 Mar. 21, 2024

Related U.S. Application Data

(60) Provisional application No. 63/401,760, filed on Aug. 29, 2022.

(51) Int. Cl.

| | |
|---|---|
| ***A61K 9/00*** | (2006.01) |
| ***A61K 47/32*** | (2006.01) |
| ***A61K 47/68*** | (2017.01) |

(52) U.S. Cl.

CPC ............ *A61K 9/0024* (2013.01); *A61K 47/32* (2013.01); *A61K 47/6807* (2017.08)

(58) Field of Classification Search

CPC . A61K 9/0024; A61K 47/32; A61M 5/14276; C07K 16/00

See application file for complete search history.

(56) References Cited

U.S. PATENT DOCUMENTS

| | | | |
|---|---|---|---|
| 2,425,389 | A | 8/1947 | Oxley et al. |
| 2,859,241 | A | 11/1958 | Schnizer |

(Continued)

FOREIGN PATENT DOCUMENTS

| | | |
|---|---|---|
| AU | 765149 B2 | 9/2003 |
| CA | 2176145 | 5/1995 |

(Continued)

OTHER PUBLICATIONS

Abstract—Almeida et al., "Ethylene vinyl acetate as matrix for oral sustained release dosage forms produced via hot-melt extrusion," *European Journal of Pharmaceutics and Biopharmaceutics*, vol. 77, Issue 2, Feb. 2011, pp. 297-305.

(Continued)

*Primary Examiner* — Carlos A Azpuru

(74) *Attorney, Agent, or Firm* — Dority & Manning, P.A.

(57) ABSTRACT

An implantable device for intratumoral delivery of a therapeutic agent is provided. The implantable device includes a polymer matrix within which is dispersed a pharmaceutical formulation that includes one or more therapeutic agents. The therapeutic agent(s) includes one or more antibodies. Optionally, the polymer matrix includes one or more excipients. The polymer matrix includes a hydrophobic polymer. The hydrophobic polymer has a melt flow index of from about 0.2 to about 100 grams per 10 minutes as determined in accordance with ASTM D1238-20 at a temperature of 190° C. and a load of 2.16 kilograms and/or a melting temperature of from about 20° C. to about 70° C. as determined in accordance with ASTM D3418-21.

19 Claims, 11 Drawing Sheets

(56) References Cited

U.S. PATENT DOCUMENTS 4,014,335 A 3/1977 Arnold
4,069,307 A 1/1978 Higuchi et al.
4,164,560 A 8/1979 Folkman et al.
4,357,312 A 11/1982 Hsieh et al.
4,391,797 A 7/1983 Folkman et al.
4,418,068 A 11/1983 Jones
4,588,394 A 5/1986 Schulte et al.
4,663,147 A 5/1987 DePrince
4,666,704 A 5/1987 Shalati et al.
4,792,448 A 12/1988 Ranade
4,843,170 A 6/1989 Isshiki et al.
4,863,735 A 9/1989 Kohn et al.
4,883,666 A 11/1989 Sabel et al.
4,891,225 A 1/1990 Langer et al.
4,898,734 A 2/1990 Mathiowitz et al.
4,900,556 A 2/1990 Wheatley et al.
4,933,185 A 6/1990 Wheatley et al.
4,952,406 A 8/1990 Brown et al.
4,957,119 A 9/1990 De Nijs
4,989,734 A 2/1991 Mode et al.
5,008,112 A 4/1991 DePrince et al.
5,034,506 A 7/1991 Summerton et al.
5,088,505 A 2/1992 De Nijs
5,100,668 A 3/1992 Edelman et al.
5,142,047 A 8/1992 Summerton et al.
5,150,718 A 9/1992 De Nijs
5,166,315 A 11/1992 Summerton et al.
5,185,444 A 2/1993 Summerton et al.
5,217,866 A 6/1993 Summerton et al.
5,302,397 A 4/1994 Amsden et al.
5,324,523 A 6/1994 Zsuga et al.
5,330,768 A 7/1994 Park et al.
5,378,475 A 1/1995 Smith et al.
5,439,688 A 8/1995 Orsolini et al.
5,443,505 A 8/1995 Wong et al.
5,506,337 A 4/1996 Summerton et al.
5,512,293 A 4/1996 Landrau et al.
5,514,378 A 5/1996 Mikos et al.
5,521,063 A 5/1996 Summerton et al.
5,543,465 A 8/1996 Bell et al.
5,545,409 A 8/1996 Laurencin et al.
5,593,974 A 1/1997 Rosenberg et al.
5,601,835 A 2/1997 Sabel et al.
5,626,862 A 5/1997 Brem et al.
5,626,877 A 5/1997 Amsden et al.
5,639,810 A 6/1997 Smith, III
5,686,877 A 11/1997 Keller et al.
5,698,685 A 12/1997 Summerton et al.
5,733,565 A 3/1998 Moo-Young et al.
5,783,186 A 7/1998 Arakawa et al.
5,783,567 A 7/1998 Hedley et al.
5,795,587 A 8/1998 Gao et al.
5,827,525 A 10/1998 Liao et al.
5,858,388 A 1/1999 Grossman et al.
5,877,224 A 3/1999 Brocchini et al.
5,902,598 A 5/1999 Chen et al.
5,916,584 A 6/1999 O'Donoghue et al.
5,989,581 A 11/1999 Groenewegen
6,001,386 A 12/1999 Ashton et al.
6,083,534 A 7/2000 Wallach et al.
6,096,764 A 8/2000 Bryant et al.
6,117,441 A 9/2000 Moo-Young et al.
6,159,143 A 12/2000 Lennox
6,217,895 B1 4/2001 Guo et al.
6,248,057 B1 6/2001 Mavity et al.
6,262,034 B1 7/2001 Mathiowitz et al.
6,281,015 B1 8/2001 Mooney et al.
RE37,410 E 10/2001 Brem et al.
6,331,313 B1 12/2001 Wong et al.
6,344,035 B1 2/2002 Chudzik et al.
6,375,972 B1 4/2002 Guo et al.
6,423,345 B2 7/2002 Bernstein et al.
6,459,917 B1 10/2002 Gowda
6,471,993 B1 10/2002 Shastri et al.
6,518,018 B1 2/2003 Szostak et al.
6,544,546 B1 4/2003 Joseph Groenewegen et al.
6,565,845 B2 5/2003 Cherksey et al.
6,565,874 B1 5/2003 Dunn et al.
6,572,874 B1 6/2003 Harrison et al.
6,582,959 B2 6/2003 Kim
6,620,617 B2 9/2003 Mathiowitz et al.
6,672,874 B2 1/2004 Guthrie
6,689,390 B2 2/2004 Bernstein et al.
6,703,020 B1 3/2004 Thorpe et al.
6,713,081 B2 3/2004 Robinson et al.
6,719,750 B2 4/2004 Varner et al.
6,730,322 B1 5/2004 Bernstein et al.
6,767,550 B1 7/2004 Génin et al.
6,808,710 B1 10/2004 Wood et al.
6,918,927 B2 7/2005 Bates et al.
6,964,781 B2 11/2005 Brubaker
6,984,720 B1 1/2006 Korman et al.
6,991,808 B2 1/2006 Brubaker et al.
7,005,454 B2 2/2006 Brocchini et al.
7,014,861 B2 3/2006 Roorda et al.
7,052,719 B2 5/2006 Bernstein et al.
7,060,269 B1 6/2006 Baca et al.
7,097,850 B2 8/2006 Chappa et al.
7,115,256 B1 10/2006 Allen et al.
7,169,901 B2 1/2007 Baca et al.
7,189,461 B2 3/2007 Rabasco et al.
7,195,774 B2 3/2007 Carvalho et al.
7,288,638 B2 10/2007 Jure-Kunkel et al.
7,309,689 B2 12/2007 Trigg et al.
7,402,385 B2 7/2008 Dadachova et al.
7,442,402 B2 10/2008 Chudzik et al.
7,452,866 B2 11/2008 Thorn et al.
7,488,802 B2 2/2009 Collins et al.
7,531,503 B2 5/2009 Atala et al.
7,534,449 B2 5/2009 Saltzman et al.
7,594,899 B2 9/2009 Pinchuk et al.
7,655,458 B2 2/2010 O'Reilly et al.
7,659,384 B2 2/2010 Jure-Kunkel et al.
7,666,445 B2 2/2010 Siegel et al.
7,691,977 B2 4/2010 Fuh et al.
7,708,711 B2 5/2010 Tu et al.
7,736,665 B2 6/2010 Patel et al.
7,763,277 B1 7/2010 Canham et al.
7,803,178 B2 9/2010 Whirley et al.
7,829,112 B2 11/2010 Ron et al.
7,833,168 B2 11/2010 Taylor et al.
7,833,545 B2 11/2010 Ron et al.
7,833,548 B2 11/2010 Chappa et al.
7,838,024 B2 11/2010 Ron et al.
7,871,643 B2 1/2011 Lizio et al.
7,883,718 B2 2/2011 Ron et al.
7,901,707 B2 3/2011 Allen et al.
7,989,018 B2 8/2011 McNiven et al.
7,993,672 B2 8/2011 Huang et al.
8,008,449 B2 8/2011 Korman et al.
8,021,680 B2 9/2011 Anderson et al.
8,039,010 B2 10/2011 Trogden et al.
8,088,060 B2 1/2012 Cottone, Jr. et al.
8,096,972 B2 1/2012 Varner et al.
8,097,236 B2 1/2012 Aston et al.
8,106,022 B2 1/2012 Monharan et al.
8,119,154 B2 2/2012 Huang et al.
8,137,667 B2 3/2012 Jure-Kunkel et al.
8,147,865 B2 4/2012 Huang et al.
8,168,757 B2 5/2012 Finnefrock et al.
8,173,163 B2 5/2012 Kohn et al.
8,182,464 B2 5/2012 Lee et al.
8,197,839 B2 6/2012 Martinod et al.
8,221,778 B2 7/2012 Siegel et al.
8,232,313 B2 7/2012 Munn et al.
8,236,857 B2 8/2012 Dill
8,257,730 B2 9/2012 Huang et al.
8,263,108 B2 9/2012 Gibson et al.
8,263,110 B2 9/2012 Huang et al.
8,268,314 B2 9/2012 Baehner et al.
8,273,375 B2 9/2012 Lizio et al.
8,298,565 B2 10/2012 Taylor et al.
8,298,570 B2 10/2012 Huang et al.
8,323,679 B2 12/2012 Ahmed et al.

(56) References Cited

U.S. PATENT DOCUMENTS

| | | | |
|---|---|---|---|
| 8,333,983 | B2 | 12/2012 | Groenewegen et al. |
| 8,348,877 | B2 | 1/2013 | Tu et al. |
| 8,354,509 | B2 | 1/2013 | Carven et al. |
| 8,377,062 | B2 | 2/2013 | Lutz et al. |
| 8,399,518 | B2 | 3/2013 | Morkin et al. |
| 8,426,554 | B2 | 4/2013 | Rozema et al. |
| 8,440,216 | B2 | 5/2013 | Huang et al. |
| 8,450,467 | B2 | 5/2013 | Manoharan et al. |
| 8,454,582 | B2 | 6/2013 | deJuan et al. |
| 8,465,769 | B2 | 6/2013 | Petereit et al. |
| 8,475,820 | B2 | 7/2013 | Kuzma et al. |
| 8,481,079 | B2 | 7/2013 | De Graaff et al. |
| 8,491,472 | B2 | 7/2013 | Mitelberg et al. |
| 8,496,954 | B2 | 7/2013 | Chappa et al. |
| 8,506,987 | B2 | 8/2013 | Shiah et al. |
| 8,541,028 | B2 | 9/2013 | Staas et al. |
| 8,552,157 | B2 | 10/2013 | Amatulli et al. |
| 8,568,766 | B2 | 10/2013 | Anantharamaiah et al. |
| 8,568,778 | B2 | 10/2013 | Lizio et al. |
| 8,580,735 | B2 | 11/2013 | Francois et al. |
| 8,609,089 | B2 | 12/2013 | Langermann et al. |
| 8,642,089 | B2 | 2/2014 | Petereit et al. |
| 8,647,657 | B2 | 2/2014 | Gibson et al. |
| 8,685,427 | B2 | 4/2014 | Li et al. |
| 8,697,104 | B2 | 4/2014 | Knezevich et al. |
| 8,703,130 | B2 | 4/2014 | Baehner et al. |
| 8,710,187 | B2 | 4/2014 | Binz et al. |
| 8,722,037 | B2 | 5/2014 | Veenstra et al. |
| 8,734,849 | B2 | 5/2014 | Lizio et al. |
| 8,741,329 | B2 | 6/2014 | de Graaff et al. |
| 8,747,883 | B2 | 6/2014 | Labib et al. |
| 8,750,988 | B2 | 6/2014 | Jolly et al. |
| 8,753,667 | B2 | 6/2014 | Variano et al. |
| 8,765,152 | B2 | 7/2014 | Lizio et al. |
| 8,765,166 | B2 | 7/2014 | Kopezynski et al. |
| 8,771,722 | B2 | 7/2014 | Huang et al. |
| 8,771,728 | B2 | 7/2014 | Huang et al. |
| 8,779,105 | B2 | 7/2014 | Korman et al. |
| 8,792,359 | B2 | 7/2014 | Mashino et al. |
| 8,795,242 | B2 | 8/2014 | Hoganson et al. |
| 8,795,707 | B2 | 8/2014 | Wolinsky et al. |
| 8,802,128 | B2 | 8/2014 | Robinson et al. |
| 8,802,773 | B2 | 8/2014 | Rozema et al. |
| 8,808,744 | B2 | 8/2014 | de Graaff et al. |
| 8,840,920 | B2 | 9/2014 | Nugara et al. |
| 8,852,623 | B2 | 10/2014 | Patel et al. |
| 8,858,977 | B2 | 10/2014 | Groenewegen et al. |
| 8,858,993 | B2 | 10/2014 | Gold et al. |
| 8,871,241 | B2 | 10/2014 | Chou et al. |
| 8,883,208 | B2 | 11/2014 | McGonigle et al. |
| 8,889,174 | B1 | 11/2014 | Gibson et al. |
| 8,900,587 | B2 | 12/2014 | Carven et al. |
| 8,900,615 | B2 | 12/2014 | Groenewegen et al. |
| 8,900,616 | B2 | 12/2014 | Belcheva et al. |
| 8,901,076 | B2 | 12/2014 | Binz et al. |
| 8,911,426 | B2 | 12/2014 | Coppeta et al. |
| 8,911,427 | B2 | 12/2014 | Seiler et al. |
| 8,932,346 | B2 | 1/2015 | Kuehling et al. |
| 8,945,552 | B2 | 2/2015 | Baehner et al. |
| 8,954,572 | B2 | 2/2015 | Jenkins |
| 8,962,009 | B2 | 2/2015 | Huang et al. |
| 8,962,010 | B2 | 2/2015 | Woolfson et al. |
| 8,962,011 | B2 | 2/2015 | Raspagliesi |
| 8,980,298 | B2 | 3/2015 | Schwarz |
| 8,992,979 | B2 | 3/2015 | Emanuel et al. |
| 8,999,390 | B2 | 4/2015 | Petersen et al. |
| 9,066,782 | B2 | 6/2015 | Tu et al. |
| 9,078,900 | B2 | 7/2015 | Kuzma et al. |
| 9,107,899 | B2 | 8/2015 | Furst et al. |
| 9,132,081 | B2 | 9/2015 | Loxley et al. |
| 9,132,088 | B2 | 9/2015 | Sim et al. |
| 9,175,162 | B2 | 11/2015 | Pacetti et al. |
| 9,198,947 | B2 | 12/2015 | Hadwiger et al. |
| 9,249,179 | B2 | 2/2016 | Hadwiger et al. |
| 9,289,466 | B2 | 3/2016 | Binz et al. |
| 9,296,687 | B2 | 3/2016 | George et al. |
| 9,301,926 | B2 | 4/2016 | Indolfi et al. |
| 9,301,990 | B2 | 4/2016 | Hadwiger et al. |
| 9,327,059 | B2 | 5/2016 | Huang et al. |
| 9,345,686 | B2 | 5/2016 | De Graaff |
| 9,370,444 | B2 | 6/2016 | Cunningham, Jr. |
| 9,370,558 | B2 | 6/2016 | Ali et al. |
| 9,370,582 | B2 | 6/2016 | Manoharan et al. |
| 9,464,292 | B2 | 10/2016 | Okumura et al. |
| 9,464,293 | B2 | 10/2016 | Rossi et al. |
| 9,492,400 | B2 | 11/2016 | Jon et al. |
| 9,493,728 | B2 | 11/2016 | Berrido et al. |
| 9,533,047 | B2 | 1/2017 | de Fougerolles et al. |
| 9,540,443 | B2 | 1/2017 | Hadari et al. |
| 9,585,912 | B2 | 3/2017 | Sherman et al. |
| 9,622,992 | B2 | 4/2017 | Dalton et al. |
| 9,642,658 | B2 | 5/2017 | Boyd et al. |
| 9,668,977 | B2 | 6/2017 | Schattka et al. |
| 9,687,506 | B2 | 6/2017 | Sherman et al. |
| 9,695,233 | B2 | 7/2017 | Duerr et al. |
| 9,708,396 | B2 | 7/2017 | Baehner et al. |
| 9,775,815 | B2 | 10/2017 | Schattka et al. |
| 9,782,346 | B2 | 10/2017 | Venkatraman et al. |
| 9,789,001 | B2 | 10/2017 | Tu et al. |
| 9,796,756 | B2 | 10/2017 | Hadwiger et al. |
| 9,808,420 | B2 | 11/2017 | Kopczynski et al. |
| 9,814,671 | B2 | 11/2017 | Lee |
| 9,814,777 | B2 | 11/2017 | Manoharan et al. |
| 9,821,045 | B2 | 11/2017 | Ali et al. |
| 9,844,511 | B2 | 12/2017 | Nollenberger et al. |
| 9,849,158 | B2 | 12/2017 | Binz et al. |
| 9,867,882 | B2 | 1/2018 | Manoharan et al. |
| 9,872,829 | B2 | 1/2018 | Loxley et al. |
| 9,872,912 | B2 | 1/2018 | Chiou et al. |
| 9,894,643 | B2 | 2/2018 | Moulsley |
| 9,895,318 | B2 | 2/2018 | Joshi et al. |
| 9,896,576 | B2 | 2/2018 | Zhang et al. |
| 9,931,330 | B2 | 4/2018 | Zarnitsyn et al. |
| 9,956,172 | B2 | 5/2018 | McGinity et al. |
| 9,968,647 | B2 | 5/2018 | Hadwiger et al. |
| 9,987,233 | B2 | 6/2018 | Helliwell et al. |
| 9,999,595 | B2 | 6/2018 | Rakic et al. |
| 10,010,612 | B2 | 7/2018 | Dadey et al. |
| 10,028,851 | B2 | 7/2018 | Dugan et al. |
| 10,029,034 | B2 | 7/2018 | Falotico et al. |
| 10,058,554 | B2 | 8/2018 | Luk et al. |
| 10,098,836 | B2 | 10/2018 | Csaky |
| 10,111,830 | B2 | 10/2018 | Patel et al. |
| 10,111,838 | B2 | 10/2018 | Joshi et al. |
| 10,123,971 | B2 | 11/2018 | Patel et al. |
| 10,131,910 | B2 | 11/2018 | Wyk |
| 10,144,762 | B2 | 12/2018 | Weller et al. |
| 10,155,946 | B2 | 12/2018 | Yehl et al. |
| 10,196,445 | B1 | 2/2019 | Engelhardt et al. |
| 10,226,419 | B2 | 3/2019 | Arps et al. |
| 10,286,197 | B2 | 5/2019 | Pouliot et al. |
| 10,363,214 | B2 | 7/2019 | Whitcup et al. |
| 10,413,504 | B2 | 9/2019 | de Graaff et al. |
| 10,413,612 | B2 | 9/2019 | Goldberg et al. |
| 10,414,828 | B2 | 9/2019 | Gschwind et al. |
| 10,434,063 | B2 | 10/2019 | McGinity et al. |
| 10,435,469 | B2 | 10/2019 | Goldberg et al. |
| 10,449,145 | B2 | 10/2019 | Csaky |
| 10,548,766 | B2 | 2/2020 | Cuevas |
| 10,568,949 | B2 | 2/2020 | Ali et al. |
| 10,590,193 | B2 | 3/2020 | Borras et al. |
| 10,596,103 | B2 | 3/2020 | Aarts et al. |
| 10,624,862 | B2 | 4/2020 | Wening et al. |
| 10,625,440 | B2 | 4/2020 | Morrissette |
| 10,625,444 | B2 | 4/2020 | Teffrer et al. |
| 10,639,283 | B2 | 5/2020 | Haksar et al. |
| 10,646,542 | B2 | 5/2020 | Binz et al. |
| 10,653,621 | B2 | 5/2020 | Wu et al. |
| 10,654,922 | B2 | 5/2020 | Lu et al. |
| 10,682,400 | B2 | 6/2020 | Ali et al. |
| 10,683,345 | B2 | 6/2020 | Duerr et al. |
| 10,702,551 | B2 | 7/2020 | Stephan |
| 10,806,791 | B2 | 10/2020 | Manoharan et al. |
| 10,835,604 | B2 | 11/2020 | Ngwa et al. |

(56) References Cited

U.S. PATENT DOCUMENTS

| | | | |
|---|---|---|---|
| 10,836,826 | B2 | 11/2020 | Goldberg et al. |
| 10,869,833 | B2 | 12/2020 | Kopczynski et al. |
| 10,874,768 | B2 | 12/2020 | Morgan et al. |
| 10,875,921 | B2 | 12/2020 | Akamatsu et al. |
| 10,881,609 | B2 | 1/2021 | Csaky |
| 10,913,947 | B2 | 2/2021 | Aznarez et al. |
| 11,021,539 | B2 | 6/2021 | Goldberg et al. |
| 11,110,174 | B2 | 9/2021 | Manoharan et al. |
| 11,116,776 | B2 | 9/2021 | Williams et al. |
| 11,161,916 | B2 | 11/2021 | Gschwind et al. |
| 11,242,395 | B2 | 2/2022 | Luo et al. |
| 11,324,935 | B2 | 5/2022 | Munster et al. |
| 11,464,857 | B2 | 10/2022 | Sloey et al. |
| 11,666,653 | B2 | 6/2023 | Manoharan et al. |
| 11,690,806 | B2 | 7/2023 | Schneider |
| 11,690,807 | B2 | 7/2023 | Schneider |
| 11,746,147 | B2 | 9/2023 | Lu et al. |
| 12,226,524 | B2 | 2/2025 | Schwendeman et al. |
| 12,312,585 | B2 | 5/2025 | Wang et al. |
| 2002/0081556 | A1 | 6/2002 | Tseng et al. |
| 2003/0149008 | A1 | 8/2003 | Sahadevan |
| 2003/0152625 | A1 | 8/2003 | Groenewegen et al. |
| 2003/0203000 | A1 | 10/2003 | Schwarz et al. |
| 2004/0092534 | A1 | 5/2004 | Yam et al. |
| 2004/0121014 | A1 | 6/2004 | Guo et al. |
| 2004/0146516 | A1 | 7/2004 | Roben et al. |
| 2004/0157244 | A1 | 8/2004 | Budahazi et al. |
| 2004/0192598 | A1 | 9/2004 | Kragie |
| 2004/0224000 | A1 | 11/2004 | Deghenghi |
| 2004/0262223 | A1 | 12/2004 | Strook et al. |
| 2005/0031668 | A1 | 2/2005 | Patel et al. |
| 2005/0137537 | A1 | 6/2005 | Watson et al. |
| 2005/0163844 | A1 | 7/2005 | Ashton |
| 2005/0220895 | A1 | 10/2005 | Bucalo et al. |
| 2005/0244462 | A1 | 11/2005 | Farooq |
| 2006/0003008 | A1 | 1/2006 | Gibson et al. |
| 2006/0052757 | A1 | 3/2006 | Fischer, Jr. et al. |
| 2006/0089410 | A1 | 4/2006 | Bucalo et al. |
| 2006/0141049 | A1 | 6/2006 | Lyons et al. |
| 2006/0147437 | A1 | 7/2006 | Allen et al. |
| 2006/0160745 | A1 | 7/2006 | Igari et al. |
| 2006/0188543 | A1 | 8/2006 | Feng |
| 2007/0043332 | A1 | 2/2007 | Malcolm et al. |
| 2007/0128294 | A1 | 6/2007 | Bucalo et al. |
| 2007/0134332 | A1 | 6/2007 | Turnell et al. |
| 2007/0179097 | A1 | 8/2007 | Furuya et al. |
| 2007/0231406 | A1 | 10/2007 | Bucalo et al. |
| 2007/0248637 | A1 | 10/2007 | Chappa et al. |
| 2007/0253959 | A1 | 11/2007 | Ferrara et al. |
| 2007/0260203 | A1 | 11/2007 | Donello et al. |
| 2007/0275031 | A1 | 11/2007 | Patel et al. |
| 2007/0282425 | A1 | 12/2007 | Kleine et al. |
| 2008/0145406 | A1 | 6/2008 | Asgharian et al. |
| 2008/0166391 | A1 | 7/2008 | Gibson et al. |
| 2008/0181900 | A1 | 7/2008 | Ferrara et al. |
| 2008/0241218 | A1 | 10/2008 | McMorrow et al. |
| 2008/0299168 | A1 | 12/2008 | Dadey et al. |
| 2009/0011007 | A1 | 1/2009 | Meier et al. |
| 2009/0035381 | A1 | 2/2009 | Stankus et al. |
| 2009/0092650 | A1 | 4/2009 | Warren et al. |
| 2009/0104243 | A1 | 4/2009 | Utkhede et al. |
| 2009/0117168 | A1 | 5/2009 | Keenan |
| 2009/0130176 | A1 | 5/2009 | Bossy-Nobs et al. |
| 2009/0142313 | A1 | 6/2009 | Talling et al. |
| 2009/0169556 | A1 | 7/2009 | Ferrara et al. |
| 2009/0173906 | A1 | 7/2009 | Park et al. |
| 2009/0239814 | A1 | 9/2009 | Manoharan et al. |
| 2009/0247608 | A1 | 10/2009 | Manoharan et al. |
| 2009/0280155 | A1 | 11/2009 | Chappa et al. |
| 2009/0311304 | A1 | 12/2009 | Borck et al. |
| 2010/0015218 | A1 | 1/2010 | Jadhav et al. |
| 2010/0047306 | A1 | 2/2010 | Loeffler et al. |
| 2010/0051575 | A1 | 3/2010 | Ou |
| 2010/0104619 | A1 | 4/2010 | De Graaff et al. |
| 2010/0111967 | A1 | 5/2010 | Baehner et al. |
| 2010/0119523 | A1 | 5/2010 | Ferrara et al. |
| 2010/0129425 | A1 | 5/2010 | De Graaff et al. |
| 2010/0158799 | A1 | 6/2010 | Chudzik et al. |
| 2010/0158980 | A1 | 6/2010 | Kopczynski et al. |
| 2010/0203066 | A1 | 8/2010 | Zhao et al. |
| 2010/0203104 | A1 | 8/2010 | De Graff et al. |
| 2010/0268288 | A1 | 10/2010 | Hunter et al. |
| 2010/0273254 | A1 | 10/2010 | Budahazi et al. |
| 2010/0278725 | A1 | 11/2010 | Liu et al. |
| 2010/0285097 | A1 | 11/2010 | Talling et al. |
| 2010/0303883 | A1 | 12/2010 | Pollock et al. |
| 2010/0316652 | A1 | 12/2010 | Ferrara et al. |
| 2011/0038936 | A1 | 2/2011 | Griswold et al. |
| 2011/0045076 | A1 | 2/2011 | Kiser et al. |
| 2011/0105990 | A1 | 5/2011 | Silvestrini |
| 2011/0207668 | A1 | 8/2011 | Binz et al. |
| 2011/0230963 | A1 | 9/2011 | Cuevas |
| 2011/0236388 | A1 | 9/2011 | Baehner et al. |
| 2011/0280922 | A1 | 11/2011 | Ron et al. |
| 2011/0287024 | A1 | 11/2011 | Ferrara et al. |
| 2012/0029042 | A1 | 2/2012 | King |
| 2012/0078362 | A1 | 3/2012 | Haffner et al. |
| 2012/0136042 | A1 | 5/2012 | Manoharan et al. |
| 2012/0157509 | A1 | 6/2012 | Hadwiger et al. |
| 2012/0164193 | A1 | 6/2012 | Dill |
| 2012/0172412 | A1 | 7/2012 | Rozema et al. |
| 2012/0207682 | A1 | 8/2012 | Ashton |
| 2012/0213725 | A1 | 8/2012 | Galleguillos et al. |
| 2012/0225129 | A1 | 9/2012 | Eliasof et al. |
| 2012/0268288 | A1 | 10/2012 | Cousin et al. |
| 2012/0276209 | A1 | 11/2012 | Cullis et al. |
| 2012/0277852 | A1 | 11/2012 | Shukia et al. |
| 2012/0302622 | A1 | 11/2012 | Eliasof et al. |
| 2012/0321627 | A1 | 12/2012 | Baehner et al. |
| 2013/0028911 | A1 | 1/2013 | Ferrara et al. |
| 2013/0037977 | A1 | 2/2013 | Burke et al. |
| 2013/0078248 | A1 | 3/2013 | Gschwind et al. |
| 2013/0116197 | A1 | 5/2013 | Binz et al. |
| 2013/0122096 | A1 | 5/2013 | Shemi et al. |
| 2013/0156845 | A1 | 6/2013 | Manoharan et al. |
| 2013/0178512 | A1 | 7/2013 | Manoharan et al. |
| 2013/0190484 | A1 | 7/2013 | Rozema et al. |
| 2013/0195951 | A1 | 8/2013 | Patel et al. |
| 2013/0202673 | A1 | 8/2013 | Patel et al. |
| 2013/0218081 | A1 | 8/2013 | Roth |
| 2013/0273137 | A1 | 10/2013 | Mandell et al. |
| 2013/0287688 | A1 | 10/2013 | Jain et al. |
| 2013/0316001 | A1 | 11/2013 | Popov et al. |
| 2014/0037746 | A1 | 2/2014 | Ashton et al. |
| 2014/0044738 | A1 | 2/2014 | Langermann et al. |
| 2014/0086995 | A1 | 3/2014 | Ratner et al. |
| 2014/0088131 | A1 | 3/2014 | Patel et al. |
| 2014/0094407 | A1 | 4/2014 | Ron et al. |
| 2014/0127228 | A1 | 5/2014 | Marks et al. |
| 2014/0135381 | A1 | 5/2014 | Hadwiger et al. |
| 2014/0179761 | A1 | 6/2014 | Manoharan et al. |
| 2014/0209100 | A1 | 7/2014 | Kiser et al. |
| 2014/0212355 | A1 | 7/2014 | Trollsas et al. |
| 2014/0221295 | A1 | 8/2014 | Binz et al. |
| 2014/0234381 | A1 | 8/2014 | Tao et al. |
| 2014/0234389 | A1 | 8/2014 | Shiah et al. |
| 2014/0271765 | A1 | 9/2014 | Patel |
| 2014/0296322 | A1 | 10/2014 | Eliasof et al. |
| 2014/0314966 | A1 | 10/2014 | Fink et al. |
| 2014/0328884 | A1 | 11/2014 | Reyes et al. |
| 2014/0343080 | A1 | 11/2014 | Siegel et al. |
| 2014/0363484 | A1 | 12/2014 | Koyakutty et al. |
| 2014/0377276 | A1 | 12/2014 | Ferrara et al. |
| 2015/0004166 | A1 | 1/2015 | Baehner et al. |
| 2015/0004213 | A1 | 1/2015 | Ron |
| 2015/0011615 | A1 | 1/2015 | Manoharan et al. |
| 2015/0119444 | A1 | 4/2015 | Manoharan et al. |
| 2015/0140062 | A1 | 5/2015 | Shiah et al. |
| 2015/0190348 | A1 | 7/2015 | Haksar et al. |
| 2015/0191535 | A1 | 7/2015 | Baehner et al. |
| 2015/0199445 | A1 | 7/2015 | Abajian et al. |
| 2015/0202076 | A1 | 7/2015 | Wijzen |
| 2015/0209440 | A1 | 7/2015 | Eliasof et al. |
| 2015/0209488 | A1 | 7/2015 | Siegel et al. |

(56) References Cited

U.S. PATENT DOCUMENTS

| | | | |
|---|---|---|---|
| 2015/0230971 A1 | 8/2015 | Wildemeersch | |
| 2015/0258120 A1 | 9/2015 | Zarnitsyn et al. | |
| 2015/0274640 A1 | 10/2015 | Wardell et al. | |
| 2015/0297509 A1 | 10/2015 | Schwarz | |
| 2015/0306230 A1 | 10/2015 | Combs et al. | |
| 2015/0342894 A1 | 12/2015 | Anderson | |
| 2015/0344539 A1 | 12/2015 | Binz et al. | |
| 2015/0366825 A1 | 12/2015 | Joshi et al. | |
| 2016/0008399 A1 | 1/2016 | Stephan | |
| 2016/0022571 A1 | 1/2016 | Schwarz et al. | |
| 2016/0051691 A1 | 2/2016 | Manoharan et al. | |
| 2016/0067071 A1 | 3/2016 | Jose et al. | |
| 2016/0081933 A1 | 3/2016 | Hensel et al. | |
| 2016/0102120 A1 | 4/2016 | Hadwiger et al. | |
| 2016/0130348 A1 | 5/2016 | Langermann et al. | |
| 2016/0143844 A1 | 5/2016 | Carrasquillo et al. | |
| 2016/0206633 A1 | 7/2016 | Barth et al. | |
| 2016/0263185 A1 | 9/2016 | Binz et al. | |
| 2016/0289677 A1 | 10/2016 | Albaek et al. | |
| 2016/0302965 A1 | 10/2016 | Erickson et al. | |
| 2016/0375137 A9 | 12/2016 | Manoharan et al. | |
| 2017/0022505 A1 | 1/2017 | Hadwiger et al. | |
| 2017/0043152 A1 | 2/2017 | Bizup | |
| 2017/0121513 A1 | 5/2017 | Zhang et al. | |
| 2017/0135380 A1 | 5/2017 | Stewart et al. | |
| 2017/0240626 A1 | 8/2017 | Baehner et al. | |
| 2017/0246117 A1 | 8/2017 | Helliwell et al. | |
| 2017/0247475 A1 | 8/2017 | Gschwind et al. | |
| 2017/0369566 A1 | 12/2017 | Baehner et al. | |
| 2018/0049988 A1 | 2/2018 | Chapanian et al. | |
| 2018/0085474 A1 | 3/2018 | Almarsson et al. | |
| 2018/0125780 A1 | 5/2018 | Grattoni et al. | |
| 2018/0125932 A1 | 5/2018 | Binz et al. | |
| 2018/0140556 A1 | 5/2018 | Joshi et al. | |
| 2018/0171386 A1 | 6/2018 | Parekkadan et al. | |
| 2018/0214507 A1 | 8/2018 | Kacker et al. | |
| 2018/0256606 A1 | 9/2018 | Petereit et al. | |
| 2018/0280194 A1 | 10/2018 | Heitzmann et al. | |
| 2018/0326070 A1 | 11/2018 | Manoharan et al. | |
| 2018/0333296 A1 | 11/2018 | Heitzmann et al. | |
| 2019/0046434 A1 | 2/2019 | Mariz et al. | |
| 2019/0099493 A1 | 4/2019 | Manoharan et al. | |
| 2019/0112354 A1 | 4/2019 | Forsayeth et al. | |
| 2019/0142882 A1 | 5/2019 | Shepherd et al. | |
| 2019/0184018 A1 | 6/2019 | Manoharan et al. | |
| 2019/0184145 A1 | 6/2019 | Munster et al. | |
| 2019/0307885 A1 | 10/2019 | Zugates et al. | |
| 2019/0345503 A1 | 11/2019 | Chang et al. | |
| 2019/0358166 A1 | 11/2019 | Schneider | |
| 2019/0358167 A1* | 11/2019 | Schneider ............ | A61K 9/5073 |
| 2019/0382492 A1 | 12/2019 | Goldberg et al. | |
| 2020/0000976 A1 | 1/2020 | Jeffery | |
| 2020/0010569 A1 | 1/2020 | Gschwind et al. | |
| 2020/0093852 A1 | 3/2020 | Nelms et al. | |
| 2020/0113829 A1 | 4/2020 | Chang et al. | |
| 2020/0138707 A1 | 5/2020 | McGinity et al. | |
| 2020/0138729 A1 | 5/2020 | Schwartz et al. | |
| 2020/0179374 A1 | 6/2020 | Orefice et al. | |
| 2020/0197327 A1 | 6/2020 | Wening et al. | |
| 2020/0297853 A1 | 9/2020 | Manoharan et al. | |
| 2020/0316159 A1 | 10/2020 | Ghatnekar | |
| 2020/0353062 A1 | 11/2020 | Sammatur et al. | |
| 2021/0007973 A1 | 1/2021 | Patel et al. | |
| 2021/0047394 A1 | 2/2021 | Baehner et al. | |
| 2021/0069293 A1 | 3/2021 | Binz et al. | |
| 2021/0095013 A1 | 4/2021 | Duerr et al. | |
| 2021/0113664 A1 | 4/2021 | Patel et al. | |
| 2021/0155782 A1 | 5/2021 | Blasius et al. | |
| 2021/0177742 A1 | 6/2021 | Patel | |
| 2022/0008541 A1 | 1/2022 | Manoharan et al. | |
| 2022/0017642 A1 | 1/2022 | Gschwind et al. | |
| 2022/0143189 A1 | 5/2022 | Manoharan et al. | |
| 2022/0313616 A1 | 10/2022 | Haley et al. | |
| 2022/0313725 A1 | 10/2022 | Haley et al. | |
| 2022/0347105 A1 | 11/2022 | Schneider et al. | |
| 2023/0027209 A1 | 1/2023 | Haley et al. | |
| 2023/0047191 A1 | 2/2023 | Wilson et al. | |
| 2023/0092955 A1 | 3/2023 | Gyanani et al. | |
| 2023/0104358 A1 | 4/2023 | Gyanani et al. | |
| 2023/0149298 A1 | 5/2023 | Patel et al. | |
| 2023/0181357 A1 | 6/2023 | Pinchuk et al. | |
| 2023/0212277 A1 | 7/2023 | Duerr et al. | |
| 2023/0233375 A1 | 7/2023 | Patel et al. | |
| 2023/0233455 A1 | 7/2023 | Patel et al. | |
| 2023/0263724 A1 | 8/2023 | Haley et al. | |
| 2023/0277469 A1 | 9/2023 | Schneider | |
| 2023/0277470 A1 | 9/2023 | Schneider | |
| 2023/0285276 A1 | 9/2023 | Haley et al. | |
| 2023/0364009 A1 | 11/2023 | Haley et al. | |
| 2023/0404907 A1 | 12/2023 | Haley et al. | |
| 2024/0180463 A1 | 6/2024 | Haley et al. | |
| 2024/0245615 A1 | 7/2024 | Schneider | |
| 2024/0269065 A1 | 8/2024 | Haley et al. | |
| 2025/0101417 A1 | 3/2025 | Haley et al. | |
| 2026/0021049 A1 | 1/2026 | Schneider et al. | |

FOREIGN PATENT DOCUMENTS

| | | | |
|---|---|---|---|
| CN | 101011345 | A | 8/2007 |
| CN | 101385698 | A | 3/2009 |
| CN | 103435424 | B | 3/2016 |
| CN | 112315898 | A | 2/2021 |
| DE | 102013011399 | A1 | 2/2014 |
| EP | 0 290 891 | A1 | 11/1988 |
| EP | 2 265 293 | B1 | 11/2015 |
| JP | H 10230148 | A | 9/1998 |
| KR | 20210010226 | A | 1/2021 |
| UA | 103635 | C2 | 11/2013 |
| WO | WO 94/10202 | A1 | 5/1994 |
| WO | WO 94/23738 | A1 | 10/1994 |
| WO | WO 98/45332 | A2 | 10/1998 |
| WO | WO 2000/075319 | A1 | 12/2000 |
| WO | WO 01/4749 | A1 | 7/2001 |
| WO | WO02062352 | A2 | 8/2002 |
| WO | WO 2004/044141 | A2 | 5/2004 |
| WO | WO 2006/063242 | A1 | 6/2006 |
| WO | WO 2009/129459 | A1 | 10/2009 |
| WO | WO 2010/133757 | A1 | 11/2010 |
| WO | WO 2010/133761 | A1 | 11/2010 |
| WO | WO 2011/116132 | A1 | 9/2011 |
| WO | WO 2011/126937 | A1 | 10/2011 |
| WO | WO 2013/178811 | A1 | 12/2013 |
| WO | WO 2013/178812 | A1 | 12/2013 |
| WO | WO 2014/009465 | A1 | 1/2014 |
| WO | WO 2014/160026 | A2 | 10/2014 |
| WO | WO 2015/083978 | A1 | 6/2015 |
| WO | WO 2016/064959 | A1 | 4/2016 |
| WO | WO 2016/079204 | A1 | 5/2016 |
| WO | WO 2016/180764 | A1 | 11/2016 |
| WO | WO 2017/040855 | A1 | 3/2017 |
| WO | WO 2017/197199 | A1 | 11/2017 |
| WO | WO 2018/067882 | A1 | 4/2018 |
| WO | WO 2019/154776 | A1 | 8/2019 |
| WO | WO 2019/213128 | A1 | 11/2019 |
| WO | WO 2020/006240 | A1 | 1/2020 |
| WO | WO 2020/041500 | A1 | 2/2020 |
| WO | WO 2020/081622 | A1 | 4/2020 |
| WO | WO 2020/081633 | A1 | 4/2020 |
| WO | WO 2020/128062 | | 6/2020 |
| WO | WO 2020/198737 | A1 | 10/2020 |
| WO | 2021/081117 | A2 | 4/2021 |
| WO | WO2021122822 | A1 | 6/2021 |
| WO | WO 2021/195163 | A1 | 9/2021 |

OTHER PUBLICATIONS

Abstract of Almeida, A. et al., "Sustained release from hot-melt extruded matrices based on ethylene vinyl acetate and polyethylene oxide," *European Journal of Pharmaceutics and Biopharmaceutics*, vol. 82, Issue 3, Nov. 2012, pp. 526-533.

Abstract of Bacus, S. et al., :Differentiation of cultured human breast cancer cell (AU-565 and MCF-7 associated with loss of cell

(56) References Cited

OTHER PUBLICATIONS surface HER-2/neu antigen. *Molecular Carinogenesis* vol. 3, Issue 6.1990. 7 pages.
Abstract—Patel et al. ; Ethylene-vinyl acetate (EVA) based implant for ocular inflammation. *Invest. Ophthalmol. Vis. Sci.* 2022;63(7):4154-F0146.
Abstract—Tagliabue et al., "Selection of monoclonal antibodies which induce internalization and phosphorylation of p185HER2 and grown inhibition of cells with HER2/NEU gene amplification," Int. J Cancer. Apr. 1, 1991;47(6):933-7, 1 page.
Agarwal et al., "Injectable implants for the sustained release of protein and peptide drugs," *Drug Discovery Today*, vol. 18, Nos. 7/8, Apr. 2013, pp. 337-349.
Ahmed et al., "Recent Advances in Polymeric Implants," *AAPS PharmSciTech*, (2019) 20: 300, 10 pages.
Arteaga, et al. p185c-erbB-2 Signaling Enhances Cisplatin-induced Cytotoxicity in Humab Breast Carcinoma Cells: Association between an Ongenic Receptor Tyrosine Kinase and Grud-induced DNA repair. *Cancer Research* 54, pp. 3758-3765, Jul. 15, 1994.
Bacus, S. et al. "Tumor-inhibitory Monoclonal Antibodies to the HER-2/Neu Receptor Induce Differentiation of Human Breast Cancer Cells." *Cancer Research* 52, pp. 2580-2589, May 1, 1992.
Bausch & Lomb Inc., "Vitrasert," Jan. 13, 2005. 22 pages.
Bix et al., "Elvax as a slow-release delivery agent for a platelet-activating factor receptor agonist and antagonist," *Journal of Neuroscience Methods*, 77, 1997, pp. 67-74.
Bloch et al., "Nerve Growth Factor- and Neurotrophin-3-Releasing Guidance Channels Promote Regeneration of the Transected Rat Dorsal Root," *Experimental Neurology* 172, 2001, pp. 425-432.
Boyer et al., "Relative Cytotoxic Activity of Immunotoxins Reactive with Different Epitopes on the Extracellular Domain of the c-erbB-2 (HER-2/neu) Gene Product p185," *Int. J. Cancer*: 82, 1999, pp. 525-531.
Broudy et al. Isolation and Characterization of a Monoclonal Antibody that Recognizes the Human c-kit Receptor. *The American Society of Hematology*. 1992. 9 pages.
Datasheet for Dexamethasone from Hello Bio, Inc., 2 pages.
Daukss et al., "Microscale implantable drug delivery systems: emerging IP strategies," *News & Analysis Biobusiness Briefs*, Nature Reviews, Drug Discovery, Nov. 2016, vol. 15, pp. 740-741.
Doughty et al., "Short Communication—Neurotrophin-3 promotes cerebellar granulate cell exit from the EGL." *European Journal of Neuroscience*, vol. 10, 1998, pp. 3007-3011.
DOW Product Information for Elvax™ EVS copolymer resins grade selection guide from The Dow Chemical Company, 2020, 4 pages.
Feng et al., "Twin-screw extrusion of sustained-release oral dosage forms and medical implants," *Drug Delivery and Translations Research*, 2018, 8, pp. 1694-1713.
Gadd et al. A Murine Monoclonal Antibody Specific for a cell-surface antigen expressed by a sub-group of human myeloid leukemias. Leukemia Research vol. 9, No. 11, pp.—1329-1336. Feb. 12, 1985.
Garcia-Estrada, "Polymeric Implants for the Treatment of the Intraocular Eye Diseases: Trends in Biodegradable and Non-Biodegradable Materials, " *Pharmaceutics* 2021, 13, 701, 20 pages.
Hancock, et al. "A Monoclonal Antibody against the c-erbB-2 Protein Enhances the Cytotoxicity of cis-Diamminedichloroplatinum against Human Breast and Ovarian Tumor Cell Lines." *Cancer Research* 51, pp. 4575-4580, Sep. 1, 1991.
Harwerth, et al. Monoclonal Antibodies against the Extracellular Domain of the erbB-2 Receptor Function as Partial Ligand Agonists. *The Journal of Biological Chemistry* vol. 267, No. 21, Issue of Jul. 25, pp. 15160-15167, 1992.
Jong et al., "Controlled release of plasmid DNA," *Journal of Controlled Release*, Release 47, 1997, pp. 123-134.
Kasprzyl, et a;. "Therapy of an Animal Model of Human Gastric Cancer Using a Combination of Anti-erbB-2 Monoclonal Antibodies." *Cancer Research* 52, pp. 2771-2776, May 15, 1992.
Kimball et al., "A novel approach to administration of peptides in women: Systemic absorption of a GnRH agonist vial transvaginal ring delivery system," *Journal of Controlled Release* 233, 2016, pp. 19-28.
Kindblom et al. Gastrointestinal Stromal Tumors Show Phenotypic Characteristics of the Interstitial Cells of Cajal. *American Journal of Pathology*, vol. 152, No. 5, May 1998. pp. 1-11.
Klapper et al. "A subclass of tumor-inhibitory monoclonal antibodies to ErbB-2/HER2 blocks crosstalk with growth factor receptors." *Oncogene* (1997) 14, pp. 2099 2109.
Kucinaks-Lipka, "Polyurethanes Crosslinked with Poly(vinyl alcohol) as a Slowly-Degradable and Hydrophilic Materials of Potential Use in Regenerative Medicine," *Materials*, 2018, 11, 351, 19 pages.
Kuo-Haller et al., "Vaccine delivery by polymeric vehicles in the mouse reproductive tract induce sustained local and systemic immunity," *Mol. Pharm*., Oct. 4, 2010, 7(5), pp. 1585-1595.
Langer et al., "Polymers for the sustained release of proteins and other macromolecules," *Nature*, vol. 263, pp. 797-800.
Loxley, Andrew, "Hot Melt-Extrusion in the Production of Intravaginal Rings Containing Antiretroviral Drugs," *ANTEC* 2010, May 18, 2010, 28 pages.
Maier et al., Requirements for the Internalization of a Murine Monoclonal Antibody Directed against the HER-2/neu Gene Product c-erbB-2.*Cancer Research* 51, 5361-5369, Oct. 1, 1991. 9 pages.
Master Dissertation of Pharm. Kristof Dhaenens entitled "Ethylene Vinyl Acetate as Matrix for Oral Sustained Release Multiple-Unit Dosage Forms Produced via Hot-Melt Extrusion," 2009-2010, Universiteit Gent, Department of Pharmaceutics, 61 pages.
McKenzie et al. Generation and characterization of monoclonal antibodies specific for the human neu oncogene products, p. 185. *Oncogene*, May 1, 1989, 4(5):543-548.
Overview of materials for Ethylene Vinyl Acetate Copolymer (EVA), Film Grade, www.matweb.com/search/datasheet, 2011, 2 pages.
Pan et al., "New paradigms on siRNA local application," *BMB Reports* 2015, pp. 147-152.
Paper—Stanković et al., "Polymeric formulations for drug release prepared by Hot Melt Extrusion, Application and characterization," pp. 16-49.
Preis et al., "Short Communication—A Single-Step Immunization by Sustained Antigen Release," *Journal of Immunological Methods*, 28, 1979, pp. 193-197.
Ramgopal et al., "Sustained Release of Complexed and Naked DNA from Polymer Films," *Journal of Biomedical Materials Research Part B: Applied Biomaterials*, 2007, pp. 496-503.
Rinaldi et al., "Antisense oligonucleotides: the next frontier for treatment of neurological disorders," *Nature Reviews/Neurology*, 2017, pp. 1-13.
Saltzman et al., "Intracranial Delivery of Recombinant Nerve Growth Factor: Release Kinetics and Protein Distribution for Three Delivery Systems," *Pharmaceutical Research*, vol. 16, No. 2, 1999, pp. 232-240.
Saltzman et al., "Transport rates of proteins in porous materials with known microgeometry," *Biophys. J.* (*Biophysical Society*), vol. 55, Jan. 1989, pp. 163-171.
Schneider et al., "Applications of ethylene vinyl acetate copolymers (EVA) in drug delivery systems," *Journal of Controlled Release* 262, 2017, pp. 284-295.
Shawver, et al. Ligand-like Effects Induced by Anti-c-erbB-2 Antibodies Do Not Correlate with and Are Not Required for Growth Inhibition of Human Carcinoma Cells. *Cancer Research* 54, pp. 1367-1373, Mar. 1, 1994.
Shin et al., "Controlled release of triprolidine using ethylene-vinyl acetate membrane and matrix systems," *European Journal of Pharmaceutics and Biopharmaceutics* 54, May 5, 2002, pp. 201-206.
Stancovski, I. et al. "Mechanistic aspects of the opposing effects of monoclonal antibodies to the ERBB2 receptor on tumor growth." *Proc. Natl. Acad. Sci. USA*. vol. 88, pp. 8691-8695, Oct. 1991.
Wadhwa et al., "Opportunities and Challenges in the Delivery of mRNA-Based Vaccines," *Pharmaceutics*, 2020, 12, 102, pp. 1-27.

(56) References Cited

OTHER PUBLICATIONS

Xu et al. "Antibody-induced growth inhibition is mediated through immunochemically and functionally distinct epitopes on the extracellular domain of the c-erbb-2 (her-2/neu) gene product p. 185." Feb. 1, 1993. *International Journal of Cancer*. vol. 53, Issue 3.
Zeng et al., "Formulation and Delivery Technologies for mRNA Vaccines," *Curr Top Microbiol Immunol*., 2022, 440, Dec. 2, 2021, pp. 1-37.
International Search Report and Written Opinion for PCT/US2023/31236 dated Nov. 21, 2023, 9 pages.
Koutsamanis et al., "Controlled-Release from High-Loaded Reservoir-Type Systems—A Case Study of Ethylene-Vinyl Acetate and Progesterone." *Pharmaceutics*, 2020, 12, 19 pages.
Elvax 760, obtained from WayBack Machine https://web.archive.org/web/20210122035942/https://www.dow.com/en-us/pdp.elvax-760-ethylene-vinyl-acetate-copolymer.1893165z.html#properties on May 15, 2024, published Jan. 22, 2021, (Year:2021).
Product Information Celanese Ateva® 4030AC Ethylene Vinyl Acetate Copolymer, 2024, 1 page (https://www.matweb/com/search/datasheet_print_aspx?matguid+bf54a0f56c394074b9cf703fea6e4).
BenEzra, David., "In Vivo Angiogenic Activity of Interleukins," *Arch. Ophthalmol*., vol. 108, Apr. 1990, pp. 573-576.
Short, Brian G., "Safety Evaluation of Ocular Drug Delivery Formulations: Techniques and Practical Considerations," *Toxicologic Pathology*, 2008, 15 pages.
Cao et al., "Recent advances in intraocular sustained-release drug delivery devices," *Drug Discov Today*, Aug. 24, 2019(8), pp. 1694-1700.
Govender et al., "Polymers in pharmaceutical additive manufacturing: A balancing act between printability and product performance," *Advanced Drug Delivery Reviews*, 177, 2021, 27 pages.
Chang Rae Sung: "PLGA Depots for Controlled Release of Bevacizumab", Online, Jan. 1, 2016 (Jan. 1, 2016), pp. 1-158.
Mohamed et al: "Sustained Delivery of Immunoglobulins from Polymer Microsources on a Narrow Surface of the Developing Rat Brain" Journal of Neuroscience Methods, [online] vol. 84, No. 1-2, Oct. 1, 1998 (Oct. 1, 1998), pp. 17-28.

* cited by examiner

IMPLANTABLE DEVICE FOR INTRATUMORALLY ADMINISTERING A THERAPEUTIC AGENT

RELATED APPLICATION

The present application is based upon and claims priority to U.S. Provisional Patent Application Ser. No. 63/401,760, having a filing date of Aug. 29, 2022, which is incorporated herein by reference.

BACKGROUND OF THE DISCLOSURE

There are a variety of treatment options for treating cancer. Such treatments can include surgery, radiation therapy, and chemotherapy. However, these methods suffer from increased side effects and many drawbacks. Other methods of treating cancer include immunotherapy, often requiring the administration of proteins, or antibodies to the patient. While antibodies have the potential for a multitude of therapeutic benefits, it has been traditionally difficult to controllably deliver sufficient amounts of these compounds in specific sites (e.g., within the tumor) over a sustained period of time.

Implantable delivery devices are formed by dispersing a pharmaceutical formulation into a matrix polymer. These dispersed drug molecules can diffuse through the implant and be released into a patient. Unfortunately, drug elution is highly dependent upon the diffusion coefficient of the drug molecule, which in turn, generally decreases with increasing molecular weight of the drug molecule. Thus, antibodies tend to have a lower diffusion coefficient due to their larger molecular weight. Various attempts have been made to help improve and control the release rate of certain types of drug compounds from an implantable device.

In light of these difficulties, a need continues to exist for an implantable delivery device that is compatible with and capable of delivering a therapeutic agent, such as an antibody, locally to a tumor over a sustained period of time.

SUMMARY OF THE DISCLOSURE

In accordance with one embodiment of the present disclosure, an implantable device for delivery of an antibody intratumorally is disclosed. The implantable device comprises a polymer matrix within which is dispersed a pharmaceutical formulation that includes one or more therapeutic agents and optionally, one or more excipients. The therapeutic agents include one or more antibodies, and the polymer matrix contains a hydrophobic polymer having a melt flow index of from about 0.2 to about 100 grams per 10 minutes as determined in accordance with ASTM D1238-20 at a temperature of 190° C. and a load of 2.16 kilograms and/or a melting temperature of from about 20° C. to about 70° C. as determined in accordance with ASTM D3418-21.

Other features and aspects of the present disclosure are set forth in greater detail below.

BRIEF DESCRIPTION OF THE FIGURES

A full and enabling disclosure of the present disclosure, including the best mode thereof, directed to one of ordinary skill in the art, is set forth more particularly in the remainder of the specification, which makes reference to the appended figures in which.

Figure 1:
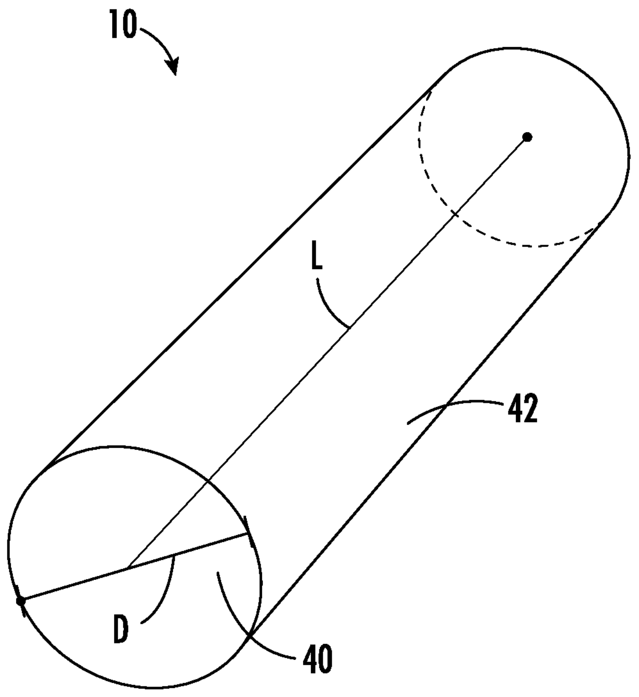
FIG. 1 is a perspective view of one embodiment of the implantable medical device of the present disclosure.

Repeat use of references characters in the present specification and drawing is intended to represent same or analogous features or elements of the disclosure.

DETAILED DESCRIPTION

It is to be understood by one of ordinary skill in the art that the present discussion is a description of exemplary embodiments only and is not intended as limiting the broader aspects of the present disclosure.

Generally speaking, the present disclosure is directed to an implantable device that is capable of delivering an antibody that can prohibit and/or treat a condition, disease, and/or cosmetic state in a patient (e.g., human, pet, farm animal, etc.). The implantable device contains a polymer matrix (e.g., core polymer matrix) that includes a hydrophobic polymer and a pharmaceutical formulation that is dispersed within the polymer matrix. The pharmaceutical formulation includes one or more therapeutic agents that include one or more antibodies and one or more optional excipients, such as buffering agents, stabilizers (e.g., surfactants, saccharides, etc.), and so forth.

Through selective control over the particular nature and concentration of the components of the implantable device, the present inventors have discovered that the resulting device can be effective for sustained release of an antibody over a prolonged period of time. For example, the implantable device can release an antibody for a time period of about 5 days or more, in some embodiments about 10 days or more, in some embodiments from about 20 days to about 210 days, and in some embodiments, from about 30 days to about 180 days.

Various embodiments of the present disclosure will now be described in more detail.

I. Polymer Matrix

As indicated above, the polymer matrix includes at least one polymer that is generally hydrophobic in nature so that it can retain its structural integrity for a certain period of time when placed in an aqueous environment, such as the body of a mammal, and stable enough to be stored for an extended period before use. The polymer matrix can be utilized to form a core or core polymer matrix as is discussed further hereinbelow. Examples of suitable hydrophobic polymers for this purpose may include, for instance, silicone polymer, polyolefins, polyvinyl chloride, polycarbonates, polysulphones, styrene acrylonitrile copolymers, polyurethanes, silicone polyether-urethanes, polycarbonate-urethanes, silicone polycarbonate-urethanes, etc., as well as combinations thereof. Of course, hydrophilic polymers that are coated or otherwise encapsulated with a hydrophobic polymer are also considered "hydrophobic polymers" and suitable for use in the polymer matrix. The melt flow index of the hydrophobic polymer(s) and resulting polymer matrix may also range from about 0.2 to about 100 g/10 min, in some embodiments from about 5 to about 90 g/10 min, in some embodiments from about 10 to about 80 g/10 min, and in some embodiments, from about 30 to about 70 g/10 min, as determined in accordance with ASTM D1238-20 at a temperature of 190° C. and a load of 2.16 kilograms. The density of the hydrophobic polymer(s) and resulting polymer matrix may also range from about 0.900 to about 1.00 gram per cubic centimeter (g/cm$^3$), in some embodiments from about 0.910 to about 0.980 g/cm$^3$, and in some embodiments, from about 0.940 to about 0.970 g/cm$^3$, as determined in accordance with ASTM D1505-18. Further, the melting temperature of the hydrophobic polymer(s) and resulting polymer matrix may likewise range from about 40° C. to about 140° C., in some embodiments from about 50° C. to about 125° C., and in some embodiments, from about 60° C. to about 120° C., as determined in accordance with ASTM D3418-21.

In certain embodiments, the polymer matrix may contain a semi-crystalline olefin copolymer. Such copolymers are generally derived from at least one olefin monomer (e.g., ethylene, propylene, etc.) and at least one polar monomer that is grafted onto the polymer backbone and/or incorporated as a constituent of the polymer (e.g., block or random copolymers). Suitable polar monomers include, for instance, a vinyl acetate, vinyl alcohol, maleic anhydride, maleic acid, (meth)acrylic acid (e.g., acrylic acid, methacrylic acid, etc.), (meth)acrylate (e.g., acrylate, methacrylate, ethyl acrylate, methyl methacrylate, ethyl methacrylate, etc.), and so forth. A wide variety of such copolymers may generally be employed in the polymer composition, such as ethylene vinyl acetate copolymers, ethylene (meth)acrylic acid polymers (e.g., ethylene acrylic acid copolymers and partially neutralized ionomers of these copolymers, ethylene methacrylic acid copolymers and partially neutralized ionomers of these copolymers, etc.), ethylene (meth)acrylate polymers (e.g., ethylene methylacrylate copolymers, ethylene ethyl acrylate copolymers, ethylene butyl acrylate copolymers, etc.), and so forth. Regardless of the particular monomers selected, certain aspects of the copolymer can be selectively controlled to help achieve the desired release properties. For instance, the polar monomer content of the copolymer may be selectively controlled to be within a range of from about 10 wt. % to about 60 wt. %, in some embodiments from about 20 wt. % to about 60 wt. %, in some embodiments from about 25 wt. % to about 50 wt. %, in some embodiments from about 30 wt. % to about 48 wt. %, and in some embodiments, from about 35 wt. % to about 45 wt. % of the copolymer. Conversely, the olefin monomer content of the copolymer may likewise be within a range of from about 40 wt. % to about 90 wt. %, in some embodiments from about 40 wt. % to about 80 wt. %, in some embodiments from about 50 wt. % to about 75 wt. %, in some embodiments from about 50 wt. % to about 80 wt. %, in some embodiments from about 52 wt. % to about 70 wt. %, and in some embodiments, from about 55 wt. % to about 65 wt. %. Among other things, such a comonomer content can help achieve a controllable, sustained release profile of the pharmaceutical formulation, while also still having a relatively low melting temperature that is more similar in nature to the melting temperature of the hydrophobic polymer(s).

In one particular embodiment, for example, the polymer matrix may contain at least one ethylene vinyl acetate polymer, which is a copolymer that is derived from at least one ethylene monomer (olefin monomer) and at least one vinyl acetate monomer (polar monomer). The melting temperature, monomer content, melt flow index, and/or density may be within the ranges noted above. Particularly suitable examples of ethylene vinyl acetate copolymers that may be employed include those available from Celanese under the designation ATEVA® (e.g., ATEVA® 4030AC); Dow under the designation ELVAX® (e.g., ELVAX® 40W); and Arkema under the designation EVATANE® (e.g., EVATANE 40-55).

Any of a variety of techniques may generally be used to form the ethylene vinyl acetate copolymer(s) with the desired properties as is known in the art. In one embodiment, the polymer is produced by copolymerizing an ethylene monomer and a vinyl acetate monomer in a high pressure reaction. Vinyl acetate may be produced from the oxidation of butane to yield acetic anhydride and acetaldehyde, which can react together to form ethylidene diacetate. Ethylidene diacetate can then be thermally decomposed in the presence of an acid catalyst to form the vinyl acetate monomer. Examples of suitable acid catalysts include aromatic sulfonic acids (e.g., benzene sulfonic acid, toluene sulfonic acid, ethylbenzene sulfonic acid, xylene sulfonic acid, and naphthalene sulfonic acid), sulfuric acid, and alkanesulfonic acids, such as described in U.S. Pat. No. 2,425,389 to Oxley et al.; U.S. Pat. No. 2,859,241 to Schnizer; and U.S. Pat. No. 4,843,170 to Isshiki et al. The vinyl acetate monomer can also be produced by reacting acetic anhydride with hydrogen in the presence of a catalyst instead of acetaldehyde. This process converts vinyl acetate directly from acetic anhydride and hydrogen without the need to produce ethylidene diacetate. In yet another embodiment, the vinyl acetate monomer can be produced from the reaction of acetaldehyde and a ketene in the presence of a suitable solid catalyst, such as a perfluorosulfonic acid resin or zeolite.

In certain embodiments, it may also be desirable to employ blends of a first hydrophobic polymer and a second hydrophobic polymer such that the overall blend and polymer matrix have a melting temperature and/or melt flow index within the range noted above. For example, the polymer matrix may contain a first hydrophobic polymer (e.g., ethylene vinyl acetate copolymer) and a second hydrophobic polymer (e.g., ethylene vinyl acetate copolymer) having a melting temperature that is greater than the melting temperature of the first polymer. The second polymer may likewise have a melt flow index that is the same, lower, or higher than the corresponding melt flow index of the first polymer. The first polymer may, for instance, have a melting temperature of from about 20° C. to about 60° C., in some embodiments from about 25° C. to about 55° C., and in some embodiments, from about 30° C. to about 50° C., such as determined in accordance with ASTM D3418-21, and/or a melt flow index of from about 40 to about 900 g/10 min, in some embodiments from about 50 to about 500 g/10 min, and in some embodiments, from about 55 to about 250 g/10 min, as determined in accordance with ASTM D1238-20 at a temperature of 190° C. and a load of 2.16 kilograms. The second polymer may likewise have a melting temperature of from about 50° C. to about 100° C., in some embodiments from about 55° C. to about 90° C., and in some embodiments, from about 60° C. to about 80° C., such as determined in accordance with ASTM D3418-21, and/or a melt flow index of from about 0.2 to about 55 g/10 min, in some embodiments from about 0.5 to about 50 g/10 min, and in some embodiments, from about 1 to about 40 g/10 min, as determined in accordance with ASTM D1238-20 at a temperature of 190° C. and a load of 2.16 kilograms. The first polymer may constitute from about 20 wt. % to about 80 wt. %, in some embodiments from about 30 wt. % to about 70 wt. %, and in some embodiments, from about 40 wt. % to about 60 wt. % of the polymer matrix, and the second polymer may likewise constitute from about 20 wt. % to about 80 wt. %, in some embodiments from about 30 wt. % to about 70 wt. %, and in some embodiments, from about 40 wt. % to about 60 wt. % of the polymer matrix.

Typically, hydrophobic polymer(s), such as ethylene vinyl acetate copolymer(s), constitute the entire polymer matrix. In other words, the polymer matrix may be generally free of hydrophilic polymers, such as alkyl celluloses and hydroxyalkyl celluloses (e.g., ethylcellulose, methylcellulose, and hydroxymethylcellulose), polyvinylpyrrolidone, and so forth. Namely, hydrophilic polymers generally constitute no more than about 10 wt. % of the polymer matrix, in some embodiments no more than about 5 wt. % of the polymer matrix, and in some embodiments, from 0 wt. % to about 2 wt. % of the polymer matrix (e.g., 0 wt. %). For example, ethylene vinyl acetate copolymers may constitute the entire polymer matrix. In other embodiments, ethylene vinyl acetate copolymers may be blended with other types of hydrophobic polymers. In such embodiments, ethylene vinyl acetate copolymer(s) may constitute from about from about 70 wt. % to about 99.999 wt. %, in some embodiments from about 80 wt. % to about 99.99 wt. %, and in some embodiments, from about 90 wt. % to about 99.9 wt. % of the polymer content of the polymer matrix, while other hydrophobic polymers constitute from about 0.001 wt. % to about 30 wt. %, in some embodiments from about 0.01 wt. % to about 20 wt. %, and in some embodiments, from about 0.1 wt. % to about 10 wt. % of the polymer content of the polymer matrix.

II. Pharmaceutical Formulation

A. Therapeutic Agents

A pharmaceutical formulation is also dispersed within the polymer matrix that contains one or more therapeutic agents, which include at least one antibody that can prohibit and/or treat a condition, disease, and/or cosmetic state in a patient. As used herein, the term "antibody" (Ab) generally includes, by way of example, both naturally occurring and non-naturally occurring Abs, monoclonal and polyclonal Abs, chimeric and humanized Abs; human or nonhuman Abs, wholly synthetic Abs, single chain Abs, etc. A nonhuman Ab may be humanized by recombinant methods to reduce its immunogenicity in man. The term "antibody" also includes an antigen-binding fragment or an antigen-binding portion of any of the disclosed immunoglobulins or peptides, and includes a monovalent and a divalent fragment or portion, and a single chain Ab. Particularly suitable antibodies may include monoclonal antibodies ("MAbs"), multispecific (e.g., bispecific) antibodies, or combinations thereof. The term "monoclonal antibody" generally refers to a non-naturally occurring preparation of Ab molecules of single molecular composition, i.e., Ab molecules whose primary sequences are essentially identical, and which exhibits a single binding specificity and affinity for a particular epitope. Multispecific antibodies, on the other hand, can bind simultaneously to different antigens (e.g., two antigens). Such antibodies are generally produced by hybridoma, recombinant, transgenic or other techniques known to those skilled in the art. A "human" antibody refers to an Ab having variable regions in which both the framework and complementarity-determining regions (CDRs) are derived from human germline immunoglobulin sequences. Furthermore, if the Ab contains a constant region, the constant region also is derived from human germline immunoglobulin sequences. The human Abs may include amino acid residues not encoded by human germline immunoglobulin sequences (e.g., mutations introduced by random or site-specific mutagenesis in vitro or by somatic mutation in vivo). However, the term "human antibody", as used herein, is not intended to include Abs in which CDR sequences derived from the germline of another mammalian species, such as a mouse, have been grafted onto human framework sequences.

In some embodiments, the antibody (including a fragment thereof) can neutralize, block, inhibit, abrogate, reduce, and/or interfere with one or more biological activities (e.g., mitogenic, angiogenic and/or vascular permeability) of a proliferating cell. Such antibodies may, for instance, bind to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), neural apoptosis-regulated proteinase 1, beta-amyloid, reticulon 4 (RTN4)/Neurite Outgrowth Inhibitor (NOGO-A), nerve growth factor (NGF), LINGO-1, myelin-associated glycoprotein, etc., as well as combinations thereof.

In one particular embodiment, for example, the antibody may be an anti-PD-1 and/or anti-PD-L1 antibody, such as employed as immune checkpoint inhibitors for treating cancer. PD-1 (or Programmed Death-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. PD-L1 (or Programmed Death Ligand-1) is one of two cell surface glycoprotein ligands for PD-1 (the other being PD-L2) that downregulate T cell activation and cytokine secretion upon binding to PD-1. The term "PD-L1" as used herein includes human PD-L1 (hPD- LI), variants, isoforms, and species homologs of hPD-LI, and analogs having at least one common epitope with hPD-LI. The complete hPD-LI sequence can be found under GenBank Accession No. Q9NZQ7. HuMAbs that bind specifically to PD-1 with high affinity have been described, for instance, in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication No. WO 2012/145493. For example, the anti-PD-1 MAb may be nivolumab. Nivolumab (also known as Opdivo®; formerly designated 5C4, BMS-936558, MDX-1106, or ONO-4538) is a fully human IgG4 (S228P) PD-1 immune checkpoint inhibitor Ab that selectively prevents interaction with PD-1 ligands (PD-LI and PD-L2), thereby blocking the downregulation of antitumor T-cell functions (U.S. Pat. No. 8,008,449). In another embodiment, the anti-PD-1 mAb is pembrolizumab, as well as antigen-binding variants thereof. Pembrolizumab (also known as Keytruda®, lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587). In other embodiments, the anti-PD-1 MAb is MED10608 (formerly AMP-514) as described, for example, in U.S. Pat. No. 8,609,089. Yet other examples of humanized monoclonal antibodies include Pidilizumab (CT-011), BGB-A317, etc., as well as antigen-binding variants thereof.

In another particular embodiment, for example, the antibody may be an anti-CTLA-4 (cytotoxic T-lymphocyte associated protein-4) antibody, such as employed as immune checkpoint inhibitors for treating cancer. CLTA-4 is a protein receptor that downregulates the immune system. The term "CTLA-4" as used herein includes human CTLA-4 (hCTLA-4), variants, isoforms, and species homologs of hCTLA-4, and analogs having at least one common epitope with hCTLA-4. Specifically, CLTA-4 is an immunoglobulin cell surface receptor and an inhibitor of T cell activation and primarily expresses naive T cells after activation and FoxP3+ regulatory T cells (Tregs). T cell activation is dependent not only on T cell receptor (TCR) binding with an antigen presented via an Adenomatous polyposis coli (APC), but also in the presence of a costimulatory second signal, typically through binding of CD28 expressed on the T cell to CD80/86 found on the APC. Absences of this secondary signal may lead the T cell to recognize the presented peptide as a "self-antigen" or to develop tolerance to the antigen. CTLA-4 is a competitive homolog for CD28 that has a higher affinity to CD80 (B7-1), and to a lesser extent CD68 (B7-2) compared with CD28, leading to inhibition of T cell stimulation. TCR signaling immediately upregulates cell surface CTLA-4 expression, reaching peak expression at 2 to 3 days after activation, providing a negative feedback loop upon T cell activation. CTLA-4 within intracellular vesicles is also quickly transported to the immunologic synapse following T cell activation. At the immunologic synapse, CTLA-4 is stabilized by CD80/CD86 binding, allowing it to collect and inhibit CD28 binding. Accordingly, inclusion of an anti-CTLA-4 antibody can disrupt the inhibitory mechanism of CTLA-4. Antibodies that bind specifically to CLTA-4 have been described, for instance, in in U.S. Pat. Nos. 6,984,720 and 10,196,445.

In certain embodiments, the anti-CTLA-4 antibody can be Ipilimumab. Ipilimumab (also known as Yervoy®, designated MDX101) is a fully humanized IgG1 kappa immunoglobulin directed against CTLA-4. Ipilimumab has an approximate molecular weight of 148 kDa. Ipilimumab is produced in mammalian (Chinese hamster ovary) cell culture. Ipilimumab is a negative regulator of T-cell activity. Ipilimumab binds to CTLA-4 and blocks the interaction of CTLA-4 with its ligands, CD80 and CD86. Blockage of CTLA-4 by Ipilimumab has been shown to augment T-cell activation and proliferation, including the activation and proliferation of tumor infiltrating T-effector cells. Inhibition of CLTA-4 signaling can also reduce T-regulatory cell function, which may contribute to a general increase in T cell responsiveness, including the anti-tumor immune response.

Another example of a suitable antibody is an anti-VEGF antibody, which is an antibody or antibody fragment (e.g., Fab or a scFV fragment) that specifically binds to a VEGF receptor. Anti-VEGF antibodies act, for example, by interfering with the binding of VEGF to a cellular receptor, by interfering with vascular endothelial cell activation after VEGF binding to a cellular receptor, and/or by killing cells activated by VEGF. An anti-VEGF antibody will usually not bind to other VEGF homologues (e.g., VEGF-B or VEGF-C) or other growth factors (e.g., PIGF, PDGF or bFGF). Suitable anti-VEGF antibodies may include monoclonal and/or bispecific anti-VEGF antibodies, such as A4.6.1, bevacizumab, ranibizumab, G6, B20, 2C3, and other antibodies such as described in U.S. Pat. Nos. 6,582,959, 6,703,020, 7,060,269, 7,169,901, 7,691,977, and 10,590,193; U.S. Patent Publication No. 2009/0169556; WO 94/10202; WO 98/45332; WO 96/30046, WO 2019/154776; WO 2010/040508; WO 2011/117329; WO 2012/131078; WO 2015/083978; WO 2017/197199; and WO 2014/009465, all of which are incorporated herein by reference. For example, the anti-VEGF antibody may be ranibizumab and/or bevacizumab, as well as antigen-binding variants thereof. Ranibizumab (molecular weight of 48 kD) is a humanized monoclonal Fab fragment directed against VEGF-A having the light and heavy chain variable domain sequences of Y0317 as described in SEQ ID Nos. 115 and 116 of U.S. Pat. No. 7,060,269. Ranibizumab inhibits endothelial cell proliferation and neovascularization and may be used for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularization (CNV) secondary to pathologic myopia. Bevacizumab (molecular weight of 149 kD) is likewise a full-length, humanized murine monoclonal antibody that recognizes all isoforms of VEGF, and which is the parent antibody of ranibizumab. In another embodiment, the anti-VEGF antibody may also be a bispecific antibody that contains a first antigen binding site that binds to human vascular endothelial growth factor (e.g., VEGF-A) and a second antigen binding site that binds to human angiopoietin-2 (ANG-2). One example of such an anti-VEGF antibody is faricimab (molecular weight of 150 kD), which is described in WO 2019/154776 and WO 2014/009465 and is composed of an anti-Ang-2 antigen-binding fragment (Fab), an anti-VEGF-A Fab, and a modified fragment crystallizable region (Fc region).

Yet another suitable antibody is an anti-HER2 antibody. Such antibodies may be full length anti-HER2 antibodies; anti-HER2 antibody fragments having the same biological activity; including amino acid sequence variants and/or glycosylation variants of such antibodies or antibody fragments. Examples of humanized anti-HER2 antibodies include trastuzumab, pertuzumab, and margetuximab, as well as antigen-binding variants thereof. Yet other anti-HER2 antibodies with various properties have been described in Tagliabue et al., Int. J. Cancer, 47:933-937 (1991); McKenzie et al., Oncogene, 4:543-548 (1989); Cancer Res., 51:5361-5369 (1991); Bacus et al., Molecular Carcinogenesis, 3:350-362 (1990); Stancovski et al., PNAS (USA), 88:8691-8695 (1991); Bacus et al., Cancer Research, 52:2580-2589 (1992); Xu et al., Int. J. Cancer, 53:401-408 (1993); WO94/00136; Kasprzyk et al., Cancer Research, 52:2771-2776 (1992); Hancock et al., Cancer Res., 51:4575-4580 (1991); Shawver et al., Cancer Res., 54:1367-1373 (1994); Arteaga et al., Cancer Res., 54:3758-3765 (1994); Harwerth et al., J. Biol. Chem., 267:15160-15167 (1992); U.S. Pat. No. 5,783,186; and Klapper et al., Oncogene, 14:2099-2109 (1997).

Yet another suitable antibody is an anti-cKIT antibody. Such antibodies may be full length anti-cKIT antibodies; anti-cKIT antibody fragments having the same biological activity; including amino acid sequence variants and/or glycosylation variants of such antibodies or antibody fragments. cKIT is a single transmembrane, receptor tyrosine kinase inhibitor that binds the ligand stem cell factor (SCF). SCF induces homodimerization of cKIT, which activates its tyrosine kinase activity and signals through both the PI3-AKT and MAPK pathways as described in Kindblom et al., Am J. Path. 1998 152(5): 1259. Anti-cKIT antibodies with various properties are described in Gadd et al., Leuk. Res. 1985 (9): 1329, Broudy et al., Blood 1992 79(2):338, U.S. Pat. Nos. 8,552,157, and 9,540,443.

Another suitable antibody is an anti-4-1 BB antibody (anti-CD137). CD137 (4-1 BB) is a member of the tumor necrosis receptor (TNF-R) gene family, which includes proteins involved in regulation of cell proliferation, differentiation, and programmed cell death. Suitable anti-4-1 BB antibodies include urelumab (BMS-663513), which is a fully human IgG4 monoclonal antibody. Other suitable anti-4-1 BB antibodies are described in U.S. Pat. Nos. 7,288,638, 7,659,384, 8,137,667, 10,875,921, 11,242,395.

Typically, the antibody is present in the formulation as a naked antibody. However, if desired, the therapeutic agent can include an antibody drug conjugate (ADC). ADCs are a rapidly growing class of targeted therapeutics, represent a promising new approach toward improving both the selectivity and the cytotoxic activity of cancer drugs (e.g., cytotoxic agents). ADCs have three components: (1) a monoclonal antibody conjugated through a (2) linker to a (3) cytotoxin. The cytotoxins are attached to either lysine or cysteine sidechains on the antibody through linkers that react selectively with primary amines on lysine or with sulfhydryl groups on cysteine.

The maximum number of linkers/drugs that can be conjugated depends on the number of reactive amino or sulfhydryl groups that are present on the antibody. A typical antibody contains up to 90 lysines as potential conjugation sites; however, the typical number of cytotoxins per antibody for most ADCs is typically between 2 and 4 due to aggregation of ADCs with higher numbers of cytotoxins. As a result, conventional lysine linked ADCs are heterogeneous mixtures that contain from 0 to 10 cytotoxins per antibody conjugated to different amino groups on the antibody. Antibody cysteines can also be used for conjugation to cytotoxins through linkers that contain maleimides or other thiol specific functional groups. A typical antibody contains 4, or sometimes 5, interchain disulfide bonds (2 between the heavy chains and 2 between heavy and light chains) that covalently bond the heavy and light chains together and contribute to the stability of the antibodies in vivo. These interchain disulfides can be selectively reduced with dithiothreitol, tris(2-carboxyethyl)phosphine, or other mild reducing agents to afford 8 reactive sulfhydryl groups for conjugation. Cysteine linked ADCs are less heterogeneous than lysine linked ADCs because there are fewer potential conjugation sites; however, they also tend to be less stable due to partial loss of the interchain disulfide bonds during conjugation, since current cysteine linkers bond to only one sulfur atom. The typical number of cytotoxins per antibody for cysteine linked ADCs can also be 2 to 4. For example, ADCETRIS is a heterogeneous mixture that contains 0 to 8 monomethylauristatin E residues per antibody conjugated through cysteines.

Key factors in the success of an ADC include that the monoclonal antibody is cancer antigen specific, non-immunogenic, low toxicity, and internalized by cancer cells; the cytotoxin is highly potent and is suitable for linker attachment; while the linker may be specific for cysteine (S) or lysine (N) binding, is stable in circulation, may be protease cleavable and/or pH sensitive, and is suitable for attachment to the cytotoxin. When used to treat cancer, for example, the ADC and/or antigen to which the antibody is bound may be internalized by the cell, resulting in increased therapeutic efficacy of the ADC in killing the cancer cell to which it binds.

The ADC can include at least one of the monoclonal antibodies described hereinabove with at least one cytotoxic agent (e.g., a chemotherapeutic agent as described hereinbelow). For instance, the ADC can comprise an anti-CLTA-4 antibody (e.g., ipilimumab) linked to one or more chemotherapeutic agents. In another example, the ADC can include an anti-PD1 antibody (e.g., nivolumab, pembrolizumab, or pidilizumab) linked to one or more chemotherapeutic agents. In another example, the ADC can include an anti-VEGF antibody (e.g., faricimab) linked to one or more chemotherapeutic agents. In another example, the ADC can include an anti-HER2 antibody (e.g., trastuzumab, pertuzumab, and margetuximab) linked to one or more chemotherapeutic agents. In yet another example, the ADC can include an anti-cKIT antibody linked to one or more chemotherapeutic agents. Suitable ADCs including anti-cKIT antibodies are described in PCT Publication No. WO 2014/150937.

The number of molecules of a drug (e.g., chemotherapeutic agent) conjugated per antibody is known as the drug-to-antibody ratio (DAR). The DAR can affect the potency and overall toxicity of the ADC. For instance, if the DAR is too low then the ACD may not be capable of providing therapeutically effective results, while if the DAR is too high, the patient may experience unwanted side effects. Given reaction and processing conditions, the DAR for ADS typically ranges anywhere from 0 to 15, such as from about 0 to 8. Accordingly, the ADCs disclosed herein can have a DAR ranging from 0 to 15, such as 1 to 14, such as 2 to 13, such as 3 to 12, such as 4 to 11, such as 5 to 10, such as 6 to 9. In certain embodiments, the ADC has a DAR of 2 to 4.

The DAR for a manufacturing batch of ADC can be determined empirically using spectrophotometric measurements and ADC therapeutic compositions typically contain a mixture of ADC species that differ in drug load. Thus, the DAR for an ADC batch represents the average DAR of the ADC species within the batch. Varying DARs per batch contributes to potency variability. In order to reduce potency variability, the ADCs contained within a batch utilized in the present pharmaceutical formulation can include an average DAR of from about 2 to about 8, such as from about 2 to about 6, such as from about 2 to 4. In a certain example, the average DAR of the ADCs is about 3 to about 5, such as about 4.

Suitable FDA-approved ADCs for use in the pharmaceutical formulation of the present disclosure also include gemtuzumab ozogamicin (Mylotarg™), brentuximab vedotin (Adetris™), trastuzumab ematansine (Kadcyla™), inotuzumab ozogamicin (Besponsa™), moxetumomab pasudotox (Lumoxiti™), polatuzumab vedotin-piiq (Polivy™), enfortumab vedontin (Padcev™), trastuzumab deruxtecan (Enhertu™), sacituzumab govitecan (Trodelvy™), belantamab mafodotin-blmf (Blenrep™), locastuximab tesirine-lpyl (Zylonta™), tisotumab vedotin-tftv (Tivdak™), and combinations thereof. Other suitable ADCs include mirvetuximab soravtansin (IMGN853), transtuzumab duocarmazine (SYD985), depatuxizumab mafodotin (AGX-414), disitimab vedotin (RC48-ADC), and combinations thereof. Other suitable ADCs include Mirvetuximab soravtansine (IMGN853), Transtuzumab duocarmazine (SYD985), Depatuxizumab mafodotin (ABT-414), Disitimab vedotin (RC48-ADC), and combinations thereof. In other embodiments, the ADC can include an antibody that is linked to other types of molecules such as oligonucleotides, radionuclides, and protein toxins.

Antibodies of the present disclosure can also include radiolabeled antibodies. Such antibodies include a radioactive substance conjugated to the antibody configured to provide radioactivity directly to cancer cells. Suitable radiolabeled antibodies include ibritumomab tiuxetan (Zevalin™). Radiolabeled antibodies include any of the antibodies disclosed herein that are conjugated with a radioactive material, such as Yttrium-90. Other radiolabeled antibodies are described in International Patent Application No. WO 2009/0538203 and U.S. Pat. No. 7,402,385.

Antibodies of the present disclosure can also include multispecific antibodies, such as bispecific antibodies (BsAbs). Multispecific antibodies refer to any antibody that can bind simultaneously to two or more different antigens, while BsAbs refers to an antibody that can bind simultaneously to two different antigens. One example BsAb is a bispecific T cell engager (BiTE) with one arm targeting CD3 on T cells and the other recognizing target proteins on tumor cells, thereby activating the T cells to kill the tumor cells. In addition to their interaction with T cells, BsABs have also been designed to engage other effector ells, such as natural killer (NK) cells and macrophages for cancer therapy. Suitable BsAbs include blinatumomab (BLINCYTO™) which targets both CD19 and CD3 and catumaxomab (Removab™) which targets human EpCAM and human CD3 receptors. Other suitable BsAbs include AMG 330 (anti-CD3/CD33), AMG 427 (anti-CD3/FLT3), AMG 673 (anti-CD3/CD33), AMG 701 (anti-CD3/BCMA), AMG 160 (anti-CD3/prostate specific membrane antigen (PSMA)), AMG 596 (anti-CD3/epidermal growth factor receptor (EGFR) and AMG 757 (anti-CD3/DLL-3), all developed by Amgen.

Other suitable BsABs or multispecific antibodies can include those currently FDA-approved and/or under clinical trial testing including Blinatumomab/Blincyto/MT1 03/MEDI-538/AMG103 (clinical trials identifiers NCT01466179 NCT02013167), AFM11 (clinical trials identifier NCT02848911), AMG562 (clinical trials identifier NCT03571828), REGN1979 (clinical trials identifier NCT03888105), Glofitamab/R07082859 (clinical trials identifier NCT03075696), Plamotamab/XmAb13676 (clinical trials identifier NCT02924402), Mosunetuzumab/RG7828/RO703081 (clinical trials identifier NCT04313608), GEN3013 (clinical trials identifier NCT03625037), AMG673 (clinical trials identifier NCT03224819), AMV-564 (clinical trials identifier NCT03144245), ISB 1342 (clinical trials identifier NCT03309111), JNJ-63709178 (clinical trials identifier NCT02715011), SAR440234 (clinical trials identifier NCT03594955), Vibecotamab/Xmab14045 (clinical trials identifier NCT02730312), AMG420/BI 836909 (clinical trials identifier NCT03836053), CC-93269/EM801 (clinical trials identifier NCT03486067), Teclistamab/JNJ-64007957 (clinical trials identifier NCT04557098), PF-06863135 (clinical trials identifier NCT04649359), REGN5458 (clinical trials identifier NCT03761108), Catumaxomab/removab (clinical trials identifier NCT03070392), RG6194/BTRC4017A (clinical trials identifier NCT03448042), M802 (clinical trials identifier NCT04501770), GBR1302 (clinical trials identifier NCT03983395), Cibisatamab/RG7802/RO6958688 (clinical trials identifier NCT03866239), AMG211 (clinical trials identifier NCT02291614), AMG160 (clinical trials identifier NCT03792841), MOR209/ES414 (clinical trials identifier NCT02262910), Pasotuxizumab/BAY2010112 (clinical trials identifier NCT01723475), REGN5678 (clinical trials identifier NCT03972657), FS120 (clinical trials identifier NCT04648202), PRS-343 (clinical trials identifier NCT03330561), AFM13 (clinical trials identifiers NCT03192202, NCT04101331), AFM24 (clinical trials identifier NCT04259450), GTB-3550, OXS-35504 (clinical trials identifier NCT03214666), MED15752 (clinical trials identifier NCT04522323), AK104 (clinical trials identifier NCT04172454), XmAb20717 (clinical trials identifier NCT03517488), MGD019 (clinical trials identifier NCT03761017), MGD013 (clinical trials identifier NCT03219268), R07121661, RG7769 (clinical trials identifier NCT03708328), KN046 (clinical trials identifiers NCT03872791, NCT04474119, NCT04469725, NCT03733951), FS118 (clinical trials identifier NCT03440437), LY3415244 (clinical trials identifier NCT03752177), 1B1318/LY3434172 (clinical trials identifier NCT03875157), 1B1315 1B1318/LY3434172 (clinical trials identifier NCT04162327), AK 12 (clinical trials identifier NCT04047290), 1B1319 (clinical trials identifier NCT04708210), FS222 (clinical trials identifier NCT04740424), MCLA-145 (clinical trials identifier NCT03922204), ATOR 1015 (clinical trials identifier NCT03782467), XmAb23104 (clinical trials identifier NCT03752398), TG-1801/NI-1701 (clinical trials identifier NCT03804996), IMM0306 (clinical trials identifier CTR20192612), 1B1322 (clinical trials identifiers NCT04338659, NCT04328831), HX009 (clinical trials identifier NCT04097769), JNJ-61186372/Amivantamab (clinical trials identifier NCT02609776), MCLA-158 (clinical trials identifier NCT03526835), MCLA-128/Zenocutuzumab (clinical trials identifier NCT03321981), KN026 (clinical trials identifier NCT04521179), MBS301 (clinical trials identifier NCT03842085), ZW25 (clinical trials identifier NCT02892123), ZW49 (clinical trials identifier NCT03821233), MM-141 (clinical trials identifier NCT02399137), BI 836880 (clinical trials identifiers NCT03972150, NCT03697304), RO5520985/Vanucizumab (clinical trials identifier NCT02141295), ABT-165/Dilpacimab (clinical trials identifier NCT01946074), OMP-305B83/Navicixizumab (clinical trials identifier NCT03030287), RG7386/RO6874813 (clinical trials identifier NCT02558140), OXS-1550/DT2219ARL (clinical trials identifier NCT02370160), and combinations thereof.

As noted above, the antibodies can include antibody fragments (Fabs). Such FDA-approved Fabs include Ranibizumab (Lucentis™), Abciximab (ReoPro™), Certolizumab pegol (Cimzia™), Idarucizumab (Praxbind™), Digoxin Immune Fab (DigiFab™), crotalidae—polyvalent immune fab (CroFab™) arotalidae—polyvalent immune Fab (Anavip™), centruroides immune F(ab')2 (Anascorp™), Brolucizumab (Beovu™), Caplacizumab (Cablivi™), or combinations thereof. Additionally Fabs that can be utilized in the present device also include Copper Cu 64-DOTA-B-Fab (clinical trials identifier NCT02708511), CSR02-Fab-TF (clinical trials identifier NCT04601428), Ranibizumab (clinical trials identifier NCT00540930), Naptumomab estafenatox (clinical trials identifier NCT00420888), IMCgp100 (clinical trials identifier NCT01209676), L19-IL2 (clinical trials identifier NCT02086721), rM28 (clinical trials identifier NCT00204594), D2C7-IT (clinical trials identifier NCT02303678), NM21-1480 (clinical trials identifier NCT04442126), Vicinium (clinical trials identifier NCT02449239), [124 I] PSCA-Minibody (clinical trials identifier NCT02092948), 6B111-OCIK (clinical trials identifier NCT03542669), T84.66 (clinical trials identifier NCT00647153), BCMA VHH CAR-T Cell (clinical trials identifier NCT03664661), CD19/20 bispecific VHH-derived CAR-T Cells (clinical trials identifier NCT03881761), ALX-0651 (clinical trials identifier NCT01374503), aPD1-MSLN-CAR T cells (clinical trials identifiers NCT04489862, NCT04503980), [131 1]-SGMIB anti-HER2 VHH1 (clinical trials identifier NCT02683083), 68-Ga NOTA-anti-MMR-VHH2 (clinical trials identifier NCT04168528), 68-GaNOTA-anti-HER2 VHH1 VHH (clinical trials identifiers NCT03924466, NCT03331601), 99mTc-MIRC208 (clinical trials identifier NCT04591652), TAS226 (clinical trials identifier NCT01529307), and combinations thereof.

In embodiments, the antibodies can include antibody cytokine fusion proteins fusion proteins, referred to as immunocytokines. Cytokines constitute a broad and loosely defined class of relatively small proteins that regulate the immune response. The systemic administration of proinflammatory cytokines is often associated with severe off target toxicity, particularly flu-like symptoms, which may limit the dose and prevent the escalation of dosages needed for developing therapeutically effective regimens. Similar to ADCs, utilization of cytokines with antibodies or antibody fragments as vehicles has been used for the targeted delivery of immunomodulatory cytokines (such as interleukin (IL)-2, IL-12, and tumor necrosis factor (TNF) including TNFa and TNFb) to leverage the local tumor microenvironment (TME) and activate anticancer immune responses. Suitable immunocytokines that may be used in accordance with the present disclosure include, but are not limited to, L191L2 (clinical trials identifier NCT01058538), L19TNFa (clinical trials identifier NCT01253837), F161L2 (clinical trials identifier NCT01134250), hu14.18-IL2 (clinical trials identifier NCT00003750), huKS-IL2 (EMD 273066) (clinical trials identifier NCT00132522), DI-Leu16-IL2 (anti-CD20-IL2) (clinical trials identifier NCT01374288), NHS-IL12 (clinical trials identifier NCT04303117), NHS-IL2-LT (EMD 521873) (clinical trials identifier NCT00879866), Anti-CEA-IL2v (cergutuzumab amunaleukin) (clinical trials identifier NCT02350673), and combinations thereof.

Antibodies of the present disclosure also include antibody-small interfering RNA (siRNA) conjugates (ARCs). Since antibodies show high specificity toward overexpressed antigens in certain cell types or tissues, antibodies can be utilized to target delivery of siRNA molecules. siRNA molecules can be linked to the antibodies with covalent linkages with lysine or cysteine residues. Accordingly, antibodies utilized herein can include the disclosed antibodies linked with one or more siRNA molecules for treating cancer. Such ARCs can be used to treat a variety of cancers. Utilization of ARCs to treat cancer has had a few drawbacks, namely ARCs may not readily enter the cell due to the negative charge of the appended siRNA, which makes it difficult to overcome the thermodynamic barriers presented by the cell membrane. As such, ARCs can be incorporated into the device of the present disclosure and released within the tumor cells themselves, eliminating thermodynamic barriers at the cell membrane.

Regardless of the type of antibody employed, it is generally stable at high enough temperatures so that it can be incorporated into the polymer matrix at or near the melting temperature of the polymer matrix without significantly degrading (e.g., melting) during manufacturing or use of the device. For example, the antibody may remain stable at temperatures of from about 20° C. to about 100° C., in some embodiments from about 25° C. to about 80° C., in some embodiments from about 30° C. to about 70° C., in some embodiments from about 35° C. to about 65° C., and in some embodiments, from about 40° C. to about 60° C. The antibody may be inherently stable at such temperatures, or it may also be encapsulated or otherwise protected by a carrier component that is stable at such temperatures, such as a carrier component containing peptides, proteins, carbohydrates (e.g., sugars), polymers, lipids, etc.

In certain embodiments, the pharmaceutical formulation may only contain antibodies (e.g., one antibody) as a therapeutic agent. Of course, in other embodiments, the formulation may contain an antibody in combination with one or more additional types of therapeutic agents. Such additional therapeutic agents may be a macromolecular compound having a relatively large molecular weight, such as about 1 kilodaltons (kDa) or more, in some embodiments from about 2 kDa to about 1000 kDa, in some embodiments from about 20 kDa to about 950 kDa, in some embodiments from about 50 kDa to about 750 kDa, and in some embodiments, from about 100 kDa to about 500 kDa, or any range therebetween. The macromolecular compound may, for instance, include a protein, peptide, enzyme, antibody, interferon, interleukin, blood factor, vaccine, nucleotide, lipid, or an analogue, derivative, or combination thereof. Alternatively, small molecule therapeutic agents may also be employed, such as those having a molecular weight of less than about 1,000 Da, in some embodiments about 900 Da or less, in some embodiments from about 10 to about 800 Da, and in some embodiments, from about 20 to about 700 Da, or any range therebetween.

Particular examples of suitable additional therapeutic agents may include, for instance, non-steroidal anti-inflammatories (e.g., salicylate, indomethacin, ibuprofen, diclofenac, flurbiprofen, piroxicam); antiallergenics (e.g., sodium chromoglycate, antazoline, methapyriline, chlorpheniramine, cetrizine, pyrilamine, prophenpyridamine); anti-proliferative agents (e.g., 1,3-cis retinoic acid); decongestants (e.g., phenylephrine, naphazoline, tetrahydrazoline); miotics and anti-cholinesterase (e.g., pilocarpine, salicylate, carbachol, acetylcholine chloride, physostigmine, eserine, diisopropyl fluorophosphate, phospholine iodine, demecarium bromide); antineoplastics (e.g., carmustine, cisplatin, fluorouracil); immunological drugs (e.g., vaccines and immune stimulants); chemotherapeutic agents; hormonal agents (e.g., estrogens, estradiol, progestational, progesterone, insulin, calcitonin, parathyroid hormone, peptide and vasopressin hypothalamus releasing factor); immunosuppressive agents, growth hormone antagonists, growth factors (e.g., epidermal growth factor, fibroblast growth factor, platelet derived growth factor, transforming growth factor beta, somatotropin, fibronectin); inhibitors of angiogenesis (e.g., angiostatin, anecortave acetate, thrombospondin, etc.); interferons (e.g., interferon alpha-2b, peg interferon alpha-2a, interferon alpha-2b+ribavirin, pegylated interferon-2a, interferon beta-1a, interferon beta); interleukins (e.g., interleukin-2); vaccines (e.g., whole viral particles, recombinant proteins, subunit proteins, gp41, gp120, gp140, DNA vaccines, plasmids, bacterial vaccines, polysaccharides, extracellular capsular polysaccharides); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; corticosteroids (e.g., dexamethasone), tyrosine kinase inhibitors (e.g., axitinib, bosutinib, cabozantinib, crizotinib, dasatinib, erlotinib, gefitinib, imatinib, lapatinib, nilotinib, pazopanib, ponatinib, ruxolitinib, sorafenib, sunitinib, vatalanib, vemurafenib, etc.), and so forth, as well as combinations of any of the foregoing.

Therapeutic agents can also include chemotherapeutic agents. Suitable chemotherapeutic agents include, but are not limited to alkylating agents, platinum drugs, antimetabolites, antitumor antibiotics, topoisomerase inhibitors, mitotic inhibitors, corticosteroids, and other miscellaneous chemotherapeutic agents. Alkylating agents directly damage DNA to prevent the cancer cell from reproducing illustrative examples of which include, nitrogen mustards (such as, mechlorethamine (nitrogen mustard), chlorambucil, cyclophosphamide (Cytoxan®), ifosfamide, and melphalan), nitrosoureas (including streptozocin, carmustine (BCNU), and lomustine), alkyl sulfonates (e.g., busulfan), triazines (such as, dacarbazine (DTIC) and temozolomide (TEMODAR®), and ethylenimines (e.g., thiotepa and altretamine (hexamethylmelamine)). The platinum drugs are sometimes grouped with alkylating agents because they kill cells in a similar way. Examples of platinum drugs include cisplatin, carboplatin, and oxalaplatin. Antimetabolites interfere with DNA and RNA growth by substituting for the normal building blocks of RNA and DNA. Examples of antimetabolites include, 5-fluorouracil (5-FU), 6-mercaptopurine (6-MP), capecitabine (XELODA®), cladribine, clofarabine, cytarabin (ARA-C®), foxuridine, fludarabine, gemcitabine (GEMZAR®), hydroxyurea, methotrexate, pemetrexed (ALIMTA®), pentostatin, and thioguanine. Anti-tumor antibiotics either break down DNA strands or slow down or stop DNA synthesis, thereby retarding the proliferation of cancer cells. Currently available anti-tumor antibiotics include anthracyclines (such as, daunorubicin, doxorubicin (ADRIAMYCIN®), epirubicin, and idarubicin), actinomycin-D, bleomycin, dactinomycin, mitomycin-C, and plicamycin. Topoisomerase inhibitors interfere with topoisomerases, which help separate the strands of DNA during cell proliferation. Examples of topoisomerase I inhibitors include camptothecin (CPT), irinotecan (CPT-11), and topotecan. Examples of topoisomerase II inhibitors include etoposide (VP-16), mitoxantrone, and teniposide. Mitotic inhibitors can stop mitosis or inhibit the synthesis of proteins involved in cell reproduction. Examples of mitotic inhibitors include, taxanes (such as, paclitaxel (TAXOL®) and docetaxel (TAXOTERE®)), epothilones, (e.g., ixabepilone (IXEMPRA®)), *vinca* alkaloids (such as, vinblastine, vincristine (ONCOVIN®), and vinorelbine (NAVELBINE®)), and estramustine.

Additional therapeutic agents can also include selective estrogen receptor modulators (SERMs). SERMs are agents that bind to estrogen receptors but that have the ability to act either as agonists or antagonists in different tissues. For example, certain SERMs act as agonists on the bone and uterus estrogen receptors and act as antagonists on the breast estrogen receptors. Growth of certain forms of cancers (e.g., breast cancers) may be dependent on estrogen. Accordingly, selective SERMS that act as antagonists on breast tissue can be used in the treatment of breast cancer. Additionally, SERMs can be useful in preventing post-menopausal osteoporosis and certain metastatic breast cancers. SERMs are small ligands of the estrogen receptor that are capable of inducing a wide variety of conformational changes in the receptor and thereby eliciting a variety of distinct biological profiles. SERMs not only affect the growth of breast cancer tissue but also influence other physiological processes.

SERMs modulate the proliferation of uterine tissue, skeletal bone density, and cardiovascular health, including plasma cholesterol levels. In general, estrogen stimulates breast and endometrial tissue proliferation, enhances bone density, and lowers plasma cholesterol. Many SERMs are bifunctional in that they antagonize some of these functions while stimulating others. For example, tamoxifen, which is a partial agonist/antagonist at the estrogen receptor inhibits estrogen-induced breast cancer cell proliferation but stimulates endometrial tissue growth and prevents bone loss.

Suitable SERMs include ospemifene, raloxifene, tamoxifene, toremifene, lasofoxifene, bazedoxifene, clomiphene citrate, ormeloxifenem, tibolone, idoxifene, or combinations thereof. SERM polymorphs, isomers, hydrates, solvates, or derivatives thereof are all meant to be encompassed in the scope of the present disclosure and shall be understood to fall under the term "SERM". Raloxifene and tamoxifene are some of the most commonly prescribed and utilized SERMs.

Raloxifene is an estrogen agonist/antagonist, which belongs to the benzothiophene class of compounds. Raloxifene is represented by structural formula (1).

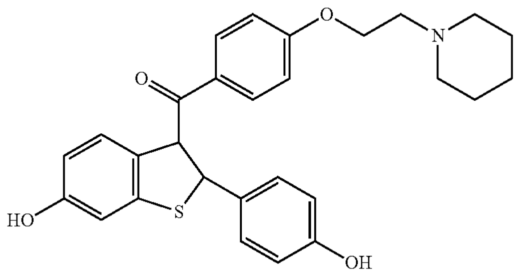

(1)

A chemical name for raloxifene hydrochloride is methanone, [6-hydroxy-2-(4-hydroxyphenyl)benzo[b]thiene-3-yl]-[4-[2-(1-piperidinyl)ethoxy]phenyl]-, hydrochloride. Raloxifene hydrochloride has the empirical formula $C_{28}H_{27}NO_4S\cdot HCl$, corresponding to a molecular weight of 510.05. Raloxifene hydrochloride is an off-white to pale yellow solid that is very slightly soluble in water, the water solubility being approximately 0.3 g/ml at 25° C., and significantly lower in simulated gastric fluid (SGF) USP (0.003 mg/ml) and simulated intestinal fluid (SIF) USP (0.002 mg/ml), at 37° C. Raloxifene and its derivatives as anti-estrogenic or anti-androgenic compounds are disclosed in U.S. Pat. No. 4,418,068.

Tamoxifen is the trans-isomer of a triphenylethylene derivative. The chemical name is (Z)2-[4-(1,2-diphenyl-1-butenyl)phenoxy]-N,N-dimethylethanamine 2-hydroxy-1,2, 3-propanetricarboxylate (1:1). The structural formula, empirical formula, and molecular weight are as follows:

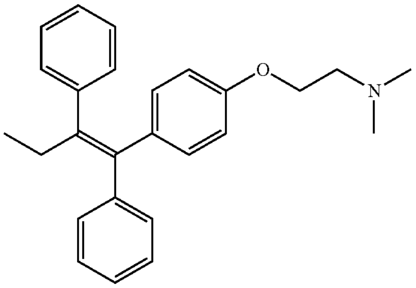 [SMILES: CC/C(=C(\c1ccccc1)c1ccc(OCCN(C)C)cc1)c1ccccc1]

The empirical formula of tamoxifene is $C_{32}H_{37}NO_8$ and it has a molecular weight of 563.62 Tamoxifen citrate has a pKa' of 8.85. The equilibrium solubility in water at 37° C. is 0.5 mg/mL, and is 0.2 mg/mL in 0.02 N HCl at 37° C.

Additional therapeutic agents can also include one or more aromatase inhibitors. Aromatase inhibitors refer to a class of agents that are capable of stopping the production of estrogen in post-menopausal women. Aromatase inhibitors work by blocking the enzyme aromatase, which functions to inhibit the conversion of testosterone and/or androgen into estradiol in the body. Accordingly, the reduction in the action of aromatase reduces the amount of estrogen in the body, therefore less estrogen is available to stimulate the growth of hormone-receptor-positive breast cancer cells. Further, aromatase inhibitors do not stop the ovaries from making estrogen, therefore, they are more commonly used to treat postmenopausal women.

Suitable examples of aromatase inhibitors include: exemestane, atamestane, formestane, fadrozole, letrozole, pentrozole, anastrozole, vorozole, or combinations thereof. In another embodiment, the aromatase inhibitor can include non-selective aromatase inhibitors such as Aminoglutethimide and Testolactone (Teslac). In yet another embodiment, aromatase inhibitors may include any other selective or non-selective chemical known to people skilled in the art that inhibits the enzyme aromatase and may prevent estrogen from being formed from its metabolic precursors. Aromatase inhibitor polymorphs, isomers, hydrates, solvates, or derivatives thereof are all meant to be encompassed in the scope of the present disclosure and shall be understood to fall under the term "aromatase inhibitor".

The weight ratio of the pharmaceutical formulation to the polymer matrix can range from about 0.3 to about 2, such as from about 0.5 to about 1.75, such as from about 0.7 to about 1.5, such as from about 1 to about 1.2. The pharmaceutical formulation can comprise from about 20 wt. % to about 80 wt. % of the device, such as from about 30 wt. % to about 70 wt. %, such as from about 20 wt. % to about 50 wt. %.

B. Excipients

In certain embodiments, the pharmaceutical formulation may contain only therapeutic agents (e.g., antibodies). Because therapeutic agents are generally water-soluble, the relative amount of such agents may be selectively controlled to help achieve the desired release rate. Namely, when only therapeutic agents are present, the weight ratio of the therapeutic agents to the polymer matrix is typically controlled within a range of from about 0.3 to about 2, in some embodiments from about 0.5 to about 1.5, in some embodiments from about 0.75 to about 0.9, and in some embodiments, from about 0.8 to about 0.85, and the therapeutic agent(s) may likewise constitute from about 30 wt. % to about 75 wt. %, such as 40 wt. % to about 60 wt. %, such as about 41 wt. % to about 48 wt. %, and in some embodiments, from about 42 wt. % to about 47 wt. % of the device.

Of course, as indicated above, the pharmaceutical formulation may also optionally contain one or more excipients, such as buffering agents, saccharides (e.g., sugars, sugar alcohols, etc.), surfactants, antimicrobial agents, preservatives, cell permeability enhancers, etc., to enhance properties and processability. Because these excipients are generally water-soluble, the relative amount of such excipients may also be selectively controlled to help achieve the desired release rate. For example, when excipients are present, the weight ratio of the therapeutic agents to the polymer matrix may be from about 0.3 to about 2, in some embodiments from about 0.75 to about 1.5, in some embodiments from about 0.35 to about 1.0, in some embodiments from about 0.5 to about 1, and in some embodiments from about 0.38 to about 0.45. Likewise, the optional excipient(s) may constitute from about 10 wt. % to about 80 wt. %, and in some embodiments, from about 20 wt. % to about 70 wt. %, and in some embodiments, from about 40 wt. % to about 60 wt. % of the pharmaceutical formulation, and therapeutic agent(s) (e.g., antibodies) may likewise constitute about 20 wt. % to about 90 wt. %, and in some embodiments, from about 30 wt. % to about 80 wt. %, and in some embodiments, from about 40 wt. % to about 60 wt. % of the pharmaceutical formulation.

The pH of the pharmaceutical formulation may, for example, desirably be within a range of from about 5.5 to about 7.5, and in some embodiments, from about 5.7 to about 6.3. To help achieve the desired level, one or more buffering agents may be employed. Exemplary buffering agents may include, for instance, a histidine buffer, such as L-histidine, L-histidine hydrochloride, L-histidine hydrochloride monohydrate, histidine succinate, histidine acetate, histidine citrate, histidine chloride or histidine sulfate, etc., as well as combinations thereof. Other suitable buffering agents may include, for instance, a salt of a metal (e.g., sodium) and an acid, such as a carboxylic acid (e.g., acetic acid, succinic acid, citric acid, etc.), phosphoric acid, etc. Such salts may include, for instance, sodium succinate, sodium acetate, sodium acetate/acetic acid, sodium phosphate, etc. When employed, the optional buffering agent(s) may constitute from about 0.01 wt. % to about 20 wt. %, and in some embodiments, from about 0.1 wt. % to about 10 wt. %, and in some embodiments, from about 0.5 wt. % to about 5 wt. % of the pharmaceutical formulation.

If desired, one or more saccharides may also be employed in the formulation to help act as a degradation stabilizer for the antibodies. Particularly suitable saccharides include, for instance, monosaccharides (e.g., dextrose, fructose, galactose, ribose, deoxyribose, etc.); disaccharides (e.g., sucrose, lactose, maltose, trehalose, etc.); sugar alcohols (e.g., xylitol, sorbitol, mannitol, maltitol, erythritol, galactitol, inositol, lactitol, etc.); and so forth, as well as combinations thereof. Trehalose (e.g., α,α-trehalose or α,α-trehalose dihydrate) is particularly suitable for use in the formulation. When employed, saccharides may constitute from about 10 wt. % to about 70 wt. %, and in some embodiments, from about 20 wt. % to about 65 wt. %, and in some embodiments, from about 30 wt. % to about 60 wt. % of the pharmaceutical formulation.

Surfactants may also be employed as an optional stabilizer for the formulation. Nonionic surfactants, which typically have a hydrophobic base (e.g., long chain alkyl group or an alkylated aryl group) and a hydrophilic chain (e.g., chain containing ethoxy and/or propoxy moieties), are particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. Particularly suitable nonionic surfactants may include ethylene oxide condensates of fatty alcohols, polyoxyethylene ethers of fatty acids, polyoxyethylene sorbitan fatty acid esters, and sorbitan fatty acid esters, etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 10 to 14 carbon atoms. Sorbitan fatty acid esters (e.g., monoesters, diester, triesters, etc.) that have been modified with polyoxyethylene are one particularly useful group of nonionic surfactants. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Examples of such materials are commercially available under the designation TWEEN® (e.g., TWEEN® 20, or polyethylene (20) sorbitan monoolaurate). When employed, surfactants may constitute from about 0.001 wt. % to about 5 wt. %, and in some embodiments, from about 0.01 wt. % to about 2 wt. %, and in some embodiments, from about 0.05 wt. % to about 1 wt. % of the solids content of the pharmaceutical formulation.

If desired, the pharmaceutical formulation may be antibody formulations that are commercially available for the treatment of certain conditions. For example, one suitable pharmaceutical formulation may be KEYTRUDA™ which contains an anti-PD1 monoclonal antibody (pembrolizumab) in combination with L-histidine, polysorbate 80, and sucrose. Another suitable formulation may be OPDIVO™, which contains an anti-PD1 monoclonal antibody (nivolumab) in combination with mannitol, pentetic acid, polysorbate 80, sodium chloride, sodium citrate dihydrate, and optionally hydrochloric acid or sodium hydroxide. Another suitable pharmaceutical formulation may be YERVOY™, which contains an anti-CLTA-4 monoclonal antibody (ipilimumab) in combination with diethylene triamine pentaacetic acid (DTPA), mannitol, polysorbate 80, sodium chloride, and tris hydrochloride. Another suitable pharmaceutical formulation may be HERCEPTIN™, which contains an anti-HER2 monoclonal antibody (trastuzumab) in combination with α,α-trehalose dihydrate, L-histidine, L-histidine hydrochloride, and polyethylene (20) sorbitan monolaurate. Another suitable formulation may be AVASTIN™, which contains an anti-VEGF monoclonal antibody (bevacizumab) in combination with trehalose dihydrate, sodium phosphate, and polyethylene (20) sorbitan monolaurate. Similarly, yet another suitable formulation may be XOLAIR™, which contains an anti-IgE monoclonal antibody (omalizumab) in combination with sucrose, histidine, histidine hydrochloride monohydrate, and polyethylene (20) sorbitan monolaurate.

Regardless of any optional excipients employed, it is generally desired that the pharmaceutical formulation is in the form of a dehydrated particulate material prior to being incorporated into the polymer matrix. In certain embodiments, for example, a liquid formulation may be dehydrated under reduced pressure using standard freeze-drying equipment or an equivalent apparatus. The antibody and/or other excipients may also be frozen in liquid nitrogen before dehydration and then placed under reduced pressure. Spray drying may also be employed to form such a particulate material. During spray drying, moisture may form a film around the particles that lowers the temperature below the temperature of the outer environment, thus minimizing the likelihood that the antibody will degrade during the drying process. In addition, various techniques (e.g., electrostatic approaches) can be employed to atomize droplets and allow for lower temperatures to be used.

III. Membrane Layer(s)

The implantable device can optionally include one or more membrane layers (e.g., a first membrane layer) that is positioned adjacent to an outer surface of a core. Additional membrane layers (e.g., a second membrane layer, a third membrane layer, etc.) may be layered on the core as desired. The number of membrane layers may vary depending on the particular configuration of the device, the nature of the therapeutic agent, and the desired release profile. For example, in certain embodiments, the device may contain only one membrane layer.

Regardless of the particular configuration employed, the membrane polymer matrix can include at least one ethylene vinyl acetate copolymer, such as described in more detail above. The vinyl acetate content of the copolymer may be selectively controlled to be within a range of from about 10 wt. % to about 60 wt. %, in some embodiments from about 20 wt. % to about 60 wt. %, in some embodiments from about 25 wt. % to about 50 wt. %, in some embodiments from about 30 wt. % to about 48 wt. %, and in some embodiments, from about 35 wt. % to about 45 wt. % of the copolymer. Conversely, the ethylene content of the copolymer may likewise be within a range of from about 40 wt. % to about 90 wt. %, in some embodiments from about 40 wt. % to about 80 wt. %, in some embodiments from about 50 wt. % to about 75 wt. %, in some embodiments from about 50 wt. % to about 80 wt. %, in some embodiments from about 52 wt. % to about 70 wt. %, and in some embodiments, from about 55 wt. % to about 65 wt. %. The melt flow index of the ethylene vinyl acetate copolymer(s) and resulting polymer matrix may also range from about 0.2 to about 400 g/10 min, in some embodiments 0.2 to about 100 g/10 min, in some embodiments from about 5 to about 90 g/10 min, in some embodiments from about 10 to about 80 g/10 min, and in some embodiments, from about 30 to about 70 g/10 min, as determined in accordance with ASTM D1238-20 at a temperature of 190° C. and a load of 2.16 kilograms. The melting temperature of the ethylene vinyl acetate copolymer may also range from about 40° C. to about 140° C., in some embodiments from about 50° C. to about 125° C., and in some embodiments, from about 60° C. to about 120° C., as determined in accordance with ASTM D3418-15. The density of the ethylene vinyl acetate copolymer(s) may also range from about 0.900 to about 1.00 gram per cubic centimeter ($g/cm^3$), in some embodiments from about 0.910 to about 0.980 $g/cm^3$, and in some embodiments, from about 0.940 to about 0.970 $g/cm^3$, as determined in accordance with ASTM D1505-18. Particularly suitable examples of ethylene vinyl acetate copolymers that may be employed include those available from Celanese under the designation ATEVA® (e.g., ATEVA® 4030AC); Dow under the designation ELVAX® (e.g., ELVAX® 40W); and Arkema under the designation EVATANE® (e.g., EVATANE 40-55). In embodiments, the ethylene vinyl acetate copolymer in the membrane polymer matrix is from about 20 wt. % to about 90 wt. %, such as from about 30 wt. % to about 80 wt. %, such as from about 40 wt. % to about 70 wt. %.

In certain cases, ethylene vinyl acetate copolymer(s) constitute the entire polymer content of the membrane polymer matrix. In other cases, however, it may be desired to include other polymers, such as other hydrophobic polymers. When employed, it is generally desired that such other polymers constitute from about 0.001 wt. % to about 30 wt. %, in some embodiments from about 0.01 wt. % to about 20 wt. %, and in some embodiments, from about 0.1 wt. % to about 10 wt. % of the polymer content of the polymer matrix. In such cases, ethylene vinyl acetate copolymer(s) may constitute about from about 70 wt. % to about 99.999 wt. %, in some embodiments from about 80 wt. % to about 99.99 wt. %, and in some embodiments, from about 90 wt. % to about 99.9 wt. % of the polymer content of the polymer matrix. The membrane polymer matrix typically constitutes from about 50 wt. % to 99 wt. %, in some embodiments, from about 55 wt. % to about 98 wt. %, in some embodiments from about 60 wt. % to about 96 wt. %, and in some embodiments, from about 70 wt. % to about 95 wt. % of a membrane layer.

To help further control the release rate from the implantable medical device, a hydrophilic compound may also be incorporated into the membrane layer(s) that is soluble and/or swellable in water. When employed, the weight ratio of the ethylene vinyl acetate copolymer(s) the hydrophilic compounds within the membrane layer may range about 0.25 to about 200, in some embodiments from about 0.4 to about 80, in some embodiments from about 0.8 to about 20, in some embodiments from about 1 to about 16, and in some embodiments, from about 1.2 to about 10. Such hydrophilic compounds may, for example, constitute from about 1 wt. % to about 60 wt. %, in some embodiments from about 2 wt. % to about 50 wt. %, and in some embodiments, from about 5 wt. % to about 40 wt. % of the core, while ethylene vinyl acetate copolymer(s) typically constitute from about 40 wt. % to about 99 wt. %, in some embodiments from about 50 wt. % to about 98 wt. %, and in some embodiments, from about 60 wt. % to about 95 wt. % of the core. Suitable hydrophilic compounds may include, for instance, polymers, non-polymeric materials (e.g., glycerin, saccharides, sugar alcohols, salts, etc.), etc. Examples of suitable hydrophilic polymers include, for instance, sodium, potassium and calcium alginates, carboxymethylcellulose, agar, gelatin, polyvinyl alcohols, polyalkylene glycols (e.g., polyethylene glycol), collagen, pectin, chitin, chitosan, poly-1-caprolactone, polyvinylpyrrolidone, poly(vinylpyrrolidone-co-vinyl acetate), polysaccharides, hydrophilic polyurethane, polyhydroxyacrylate, dextran, xanthan, hydroxypropyl cellulose, methylcellulose, proteins, ethylene vinyl alcohol copolymers, water-soluble polysilanes and silicones, water-soluble polyurethanes, etc., as well as combinations thereof. Particularly suitable hydrophilic polymers are polyalkylene glycols, such as those having a molecular weight of from about 100 to 500,000 grams per mole, in some embodiments from about 500 to 200,000 grams per mole, and in some embodiments, from about 1,000 to about 100,000 grams per mole. Specific examples of such polyalkylene glycols include, for instance, polyethylene glycols, polypropylene glycols polytetramethylene glycols, polyepichlorohydrins, etc.

Optionally, the membrane layer(s) include a plurality of water-soluble particles distributed within a membrane polymer matrix. The particle size of the water-soluble particles is controlled to help achieve the desired delivery rate. More particularly, the median diameter (D50) of the particles is about 100 micrometers or less, in some embodiments about 80 micrometers or less, in some embodiments about 60 micrometers or less, and in some embodiments, from about 1 to about 40 micrometers, such as determined using a laser scattering particle size distribution analyzer (e.g., LA-960 from Horiba). The particles may also have a narrow size distribution such that 90% or more of the particles by volume (D90) have a diameter within the ranges noted above. In addition to controlling the particle size, the materials employed to form the water-soluble particles are also selected to achieve the desired release profile. More particularly, the water-soluble particles generally contain a hydroxy-functional compound that is not polymeric. The term "hydroxy-functional" generally means that the compound contains at least one hydroxyl group, and in certain cases, multiple hydroxyl groups, such as 2 or more, in some embodiments 3 or more, in some embodiments 4 to 20, and in some embodiments, from 5 to 16 hydroxyl groups. The term "non-polymeric" likewise generally means that the compound does not contain a significant number of repeating units, such as no more than 10 repeating units, in some embodiments no or more than 5 repeating units, in some embodiments no more than 3 repeating units, and in some embodiments, no more than 2 repeating units. In some cases, such a compound lacks any repeating units. Such non-polymeric compounds thus a relatively low molecular weight, such as from about 1 to about 650 grams per mole, in some embodiments from about 5 to about 600 grams per mole, in some embodiments from about 10 to about 550 grams per mole, in some embodiments from about 50 to about 500 grams per mole, in some embodiments from about 80 to about 450 grams per mole, and in some embodiments, from about 100 to about 400 grams per mole. Particularly suitable non-polymeric, hydroxy-functional compounds that may be employed in the present disclosure include, for instance, saccharides and derivatives thereof, such as monosaccharides (e.g., dextrose, fructose, galactose, ribose, deoxyribose, etc.); disaccharides (e.g., sucrose, lactose, maltose, etc.); sugar alcohols (e.g., xylitol, sorbitol, mannitol, maltitol, erythritol, galactitol, isomalt, inositol, lactitol, etc.); and so forth, as well as combinations thereof. If utilized, the water-soluble particles typically constitute from about 1 wt. % to about 50 wt. %, in some embodiments from about 2 wt. % to about 45 wt. %, in some embodiments from about 4 wt. % to about 40 wt. %, and in some embodiments, from about 5 wt. % to about 30 wt. % of a membrane layer.

When employing multiple membrane layers, it is typically desired that each membrane layer contains a polymer matrix includes an ethylene vinyl acetate copolymer. Additionally, each of the membrane layers can include a plurality of water-soluble particles distributed within a membrane polymer matrix that includes an ethylene vinyl acetate copolymer. For example, a first membrane layer may contain first water-soluble particles distributed within a first membrane polymer matrix and a second membrane layer may contain second water-soluble particles distributed within a second membrane polymer matrix. In such embodiments, the first and second polymer matrices may each contain an ethylene vinyl acetate copolymer. The water-soluble particles and ethylene vinyl acetate copolymer(s) within one membrane layer may be the same or different than those employed in another membrane layer. In one embodiment, for instance, both the first and second membrane polymer matrices employ the same ethylene vinyl acetate copolymer(s) and the water-soluble particles within each layer have the same particle size and/or are formed from the same material.

Likewise, the ethylene vinyl acetate copolymer(s) used in the membrane layer(s) may also be the same or different the hydrophobic polymer(s) employed in the core. In one embodiment, for instance, both the core and the membrane layer(s) employ the same ethylene vinyl acetate copolymer. In yet other embodiments, the membrane layer(s) may employ an ethylene vinyl acetate copolymer that has a lower melt flow index than a hydrophobic polymer employed in the core. Among other things, this can further help control the release of the therapeutic agent from the device. For example, the ratio of the melt flow index of a hydrophobic polymer employed in the core to the melt flow index of an ethylene vinyl acetate copolymer employed in the membrane layer(s) may be from about 1 to about 20, in some embodiments about 2 to about 15, and in some embodiments, from about 4 to about 12.

Optionally, the membrane can include one or more porous membranes configured to facilitate release of the therapeutic agent from the device. The porous membrane can be formed from suitable materials such as polytetrafluorehtylene (PTFE), polyethersulfone (PES), and combinations thereof. Suitable PFTEs including modified PTFE (mPTFE) and expanded PTFE (ePTFE). The porous membrane can include a variety of porous materials, including microporous materials. For instance, the porous membrane includes microporous ePTFE, microporous PES, and combinations thereof.

In certain other embodiments, the device can include one or more membrane layer formed form a polymer material configured to restrict release of the therapeutic agent or to direct release of the therapeutic agent to certain regions or areas of the device. For instance, certain polymeric materials can be used as membrane materials to restrict release of the therapeutic agent. Suitable polymeric materials can include polyoxymethylene (POM), liquid crystal polymers (LCPs), and combinations thereof. Other materials that can form part or all of the membrane include metal materials, metalloids, or metal oxides, such a titanium.

If desired, membrane layer(s) used in the device may optionally contain a therapeutic agent, such as described below, which is also dispersed within the membrane polymer matrix. The therapeutic agent in the membrane layer(s) may be the same or different than the therapeutic agent employed in the core. When such a therapeutic agent is employed in a membrane layer, the membrane layer generally contains the therapeutic agent in an amount such that the ratio of the concentration (wt. %) of the therapeutic agent in the core to the concentration (wt. %) of the therapeutic agent in the membrane layer is greater than 1, in some embodiments about 1.5 or more, and in some embodiments, from about 1.8 to about 4. When employed, therapeutic agents typically constitute only from about 1 wt. % to about 40 wt. %, in some embodiments from about 5 wt. % to about 35 wt. %, and in some embodiments, from about 10 wt. % to about 30 wt. % of a membrane layer. Of course, in other embodiments, the membrane layer is generally free of therapeutic agents prior to release from the core. When multiple membrane layers are employed, each membrane layer may generally contain the therapeutic agent in an amount such that the ratio of the weight percentage of the therapeutic agent in the core to the weight percentage of the therapeutic agent in the membrane layer is greater than 1, in some embodiments about 1.5 or more, and in some embodiments, from about 1.8 to about 4.

The membrane layer(s) may also optionally contain one or more excipients as described above, such as radiocontrast agents, bulking agents, plasticizers, surfactants, crosslinking agents, flow aids, colorizing agents (e.g., chlorophyll, methylene blue, etc.), antioxidants, stabilizers, lubricants, other types of antimicrobial agents, preservatives, etc. to enhance properties and processability. When employed, the optional excipient(s) typically constitute from about 0.01 wt. % to about 60 wt. %, and in some embodiments, from about 0.05 wt. % to about 50 wt. %, and in some embodiments, from about 0.1 wt. % to about 40 wt. % of a membrane layer.

The membrane layer(s) may be formed using the same or a different technique than used to form the core, such as by hot-melt extrusion, compression molding (e.g., vacuum compression molding), injection molding, solvent casting, dip coating, spray coating, microextrusion, coacervation, etc. In other embodiments, the membrane layer(s) can be wrapped around the core and heat sealed to the core. For instance, the membrane layer (s) can be helically, radially, or longitudinally wrapped around the core and heat sealed. In one embodiment, a hot-melt extrusion technique may be employed. The core and membrane layer(s) may also be formed separately or simultaneously. In one embodiment, for instance, the core and membrane layer(s) are separately formed and then combined together using a known bonding technique, such as by stamping, hot sealing, adhesive bonding, etc. Compression molding (e.g., vacuum compression molding) may also be employed to form the implantable device. As described above, the core and membrane layer(s) may be each individually formed by heating and compressing the respective polymer compression into the desired shape while under vacuum. Once formed, the core and membrane layer(s) may be stacked together to form a multi-layer precursor and thereafter and compression molded in the manner as described above to form the resulting implantable device.

IV. Implantable Device

The implantable device may be formed through a variety of known techniques, such as by hot-melt extrusion, injection molding, solvent casting, dip coating, spray coating, microextrusion, coacervation, etc. In one embodiment, a hot-melt extrusion technique may be employed. Hot-melt extrusion is generally a solvent-free process in which the components of the device (e.g., hydrophobic polymer(s), antibodies, optional excipients, etc.) may be melt blended and optionally shaped in a continuous manufacturing process to enable consistent output quality at high throughput rates. This technique is particularly well suited to certain types of hydrophobic polymers (e.g., ethylene vinyl acetate copolymers) that can exhibit a high degree of long-chain branching with a broad molecular weight distribution. This combination of traits can lead to shear thinning of the copolymer during the extrusion process, which help facilitates hot-melt extrusion. Furthermore, the polar comonomer units can serve as an "internal" plasticizer by inhibiting crystallization of the olefin chain segments. This may lead to a lower melting point of the polymer, which further enhances its ability to be processed with the antibody.

During a hot-melt extrusion process, melt blending generally occurs at a temperature that is similar to or even less than the melting temperature of the antibodies. Melt blending may also occur at a temperature that is similar to or slightly above the melting temperature of the hydrophobic polymer(s). The ratio of the melt blending temperature to the degradation temperature of the antibody may, for instance, be about 2 or less, in some embodiments about 1.8 or less, in some embodiments from about 0.1 to about 1.6, in some embodiments from about 0.2 to about 1.5, and in some embodiments, from about 0.4 to about 1.2. The melt blending temperature may, for example, be from about 30° C. to about 100° C., in some embodiments, from about 40° C. to about 80° C., and in some embodiments, from about 50° C. to about 70° C. Any of a variety of melt blending techniques may generally be employed. For example, the components may be supplied separately or in combination to an extruder that includes at least one screw rotatably mounted and received within a barrel (e.g., cylindrical barrel). The extruder may be a single screw or twin screw extruder. For example, one embodiment of a single screw extruder may contain a housing or barrel and a screw rotatably driven on one end by a suitable drive (typically including a motor and gearbox). If desired, a twin-screw extruder may be employed that contains two separate screws. The configuration of the screw is not particularly critical and it may contain any number and/or orientation of threads and channels as is known in the art. For example, the screw typically contains a thread that forms a generally helical channel radially extending around the center of the screw. A feed section and melt section may be defined along the length of the screw. The feed section is the input portion of the barrel where the hydrophobic polymer(s) and/or antibody are added. The melt section is the phase change section in which the copolymer is changed from a solid to a liquid-like state. While there is no precisely defined delineation of these sections when the extruder is manufactured, it is well within the ordinary skill of those in this art to reliably identify the feed section and the melt section in which phase change from solid to liquid is occurring. Although not necessarily required, the extruder may also have a mixing section that is located adjacent to the output end of the barrel and downstream from the melting section. If desired, one or more distributive and/or dispersive mixing elements may be employed within the mixing and/or melting sections of the extruder. Suitable distributive mixers for single screw extruders may include, for instance, Saxon, DuImage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin mixers.

If desired, the ratio of the length ("L") to diameter ("D") of the screw may be selected to achieve an optimum balance between throughput and blending of the components. The L/D value may, for instance, range from about 10 to about 50, in some embodiments from about 15 to about 45, and in some embodiments from about 20 to about 40. The length of the screw may, for instance, range from about 0.1 to about 5 meters, in some embodiments from about 0.4 to about 4 meters, and in some embodiments, from about 0.5 to about 2 meters. The diameter of the screw may likewise be from about 5 to about 150 millimeters, in some embodiments from about 10 to about 120 millimeters, and in some embodiments, from about 20 to about 80 millimeters. In addition to the length and diameter, other aspects of the extruder may also be selected to help achieve the desired degree of blending. For example, the speed of the screw may be selected to achieve the desired residence time, shear rate, melt processing temperature, etc. For example, the screw speed may range from about 10 to about 800 revolutions per minute ("rpm"), in some embodiments from about 20 to about 500 rpm, and in some embodiments, from about 30 to about 400 rpm. The apparent shear rate during melt blending may also range from about 100 $seconds^{-1}$ to about 10,000 $seconds^{-1}$, in some embodiments from about 500 $seconds^{-1}$ to about 5000 $seconds^{-1}$, and in some embodiments, from about 800 $seconds^{-1}$ to about 1200 $seconds^{-1}$. The apparent shear rate is equal to $4\,Q/\pi R^3$, where Q is the volumetric flow rate ("$m^3/s$") of the polymer melt and R is the radius ("m") of the capillary (e.g., extruder die) through which the melted polymer flows.

Once melt blended together, the resulting polymer composition may be extruded through an orifice (e.g., die) and formed into pellets, sheets, fibers, filaments, etc., which may be thereafter shaped into the implantable device using a variety of known shaping techniques, such as injection molding, compression molding, nanomolding, overmolding, blow molding, three-dimensional printing, etc. Injection molding may, for example, occur in two main phases—i.e., an injection phase and holding phase. During the injection phase, a mold cavity is filled with the molten polymer composition. The holding phase is initiated after completion of the injection phase in which the holding pressure is controlled to pack additional material into the cavity and compensate for volumetric shrinkage that occurs during cooling. After the shot has built, it can then be cooled. Once cooling is complete, the molding cycle is completed when the mold opens and the part is ejected, such as with the assistance of ejector pins within the mold. Any suitable injection molding equipment may generally be employed in the present disclosure. In one embodiment, an injection molding apparatus may be employed that includes a first mold base and a second mold base, which together define a mold cavity having the shape of the implantable device. The molding apparatus includes a resin flow path that extends from an outer exterior surface of the first mold half through a sprue to a mold cavity. The polymer composition may be supplied to the resin flow path using a variety of techniques. For example, the composition may be supplied (e.g., in the form of pellets) to a feed hopper attached to an extruder barrel that contains a rotating screw (not shown). As the screw rotates, the pellets are moved forward and undergo pressure and friction, which generates heat to melt the pellets. A cooling mechanism may also be provided to solidify the resin into the desired shape for the implantable device (e.g., disc, rod, etc.) within the mold cavity. For instance, the mold bases may include one or more cooling lines through which a cooling medium flows to impart the desired mold temperature to the surface of the mold bases for solidifying the molten material. The mold temperature (e.g., temperature of a surface of the mold) may range from about 50° C. to about 120° C., in some embodiments from about 60° C. to about 110° C., and in some embodiments, from about 70° C. to about 90° C.

As indicated above, another suitable technique for forming an implantable device of a desired shape and size is three-dimensional printing. During this process, the polymer composition may be incorporated into a printer cartridge that is readily adapted for use with a printer system. The printer cartridge may, for example, contains a spool or other similar device that carries the polymer composition. When supplied in the form of filaments, for example, the spool may have a generally cylindrical rim about which the filaments are wound. The spool may likewise define a bore or spindle that allows it to be readily mounted to the printer during use. Any of a variety of three-dimensional printer systems can be employed in the present disclosure. Particularly suitable printer systems are extrusion-based systems, which are often referred to as "fused deposition modeling" systems. For example, the polymer composition may be supplied to a build chamber of a print head that contains a platen and gantry. The platen may move along a vertical z-axis based on signals provided from a computer-operated controller. The gantry is a guide rail system that may be configured to move the print head in a horizontal x-y plane within the build chamber based on signals provided from controller. The print head is supported by the gantry and is configured for printing the build structure on the platen in a layer-by-layer manner, based on signals provided from the controller. For example, the print head may be a dual-tip extrusion head.

Compression molding (e.g., vacuum compression molding) may also be employed. In such a method, a layer of the device may be formed by heating and compressing the polymer compression into the desired shape while under vacuum. More particularly, the process may include forming the polymer composition into a precursor that fits within a chamber of a compression mold, heating the precursor, and compression molding the precursor into the desired layer while the precursor is heated. The polymer composition may be formed into a precursor through various techniques, such as by dry power mixing, extrusion, etc. The temperature during compression may range from about 50° C. to about 120° C., in some embodiments from about 60° C. to about 110° C., and in some embodiments, from about 70° C. to about 90° C. A vacuum source may also apply a negative pressure to the precursor during molding to help ensure that it retains a precise shape. Examples of such compression molding techniques are described, for instance, in U.S. Pat. No. 10,625,444 to Treffer, et al., which is incorporated herein in its entirety by reference thereto.

The resulting implantable medical device may have a variety of different geometric shapes, such as cylindrical (rod), disc, ring, doughnut, helical, elliptical, triangular, ovular, etc. In one embodiment, for example, the implantable medical device may have a generally circular cross-sectional so that the overall structure is in the form of a cylinder (rod) or disc. The implantable medical device also has a relatively small size, such as a thickness (e.g., diameter) of from about 0.1 to about 10 millimeters, in some embodiments from about 0.1 to about 5 millimeters, in some embodiments from about 0.3 to about 2 millimeters, and in some embodiments, from about 0.4 to about 0.8 millimeters. The length of the implantable medical device may vary, but is typically from about 1 to about 250 millimeters, in some embodiments from about 2 to about 200 millimeters, in some embodiments from about 10 to about 150 millimeters, and in some embodiments, from about 20 to about 100 millimeters.

Figure 2:
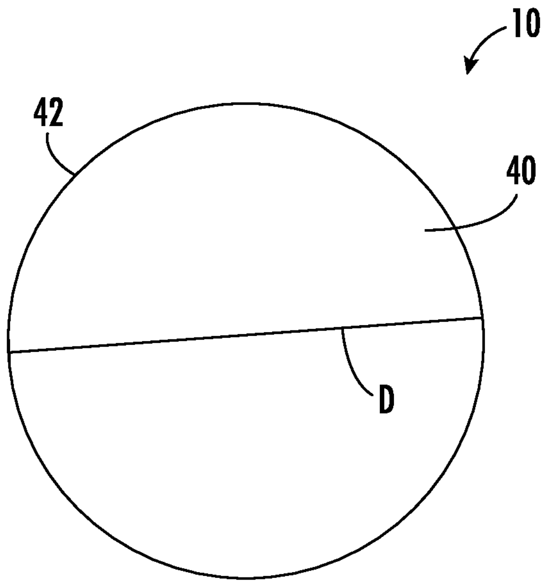
FIG. 2 is a cross-sectional view of the implantable medical device of FIG. 1.

Referring to FIGS. 1-2, for example, one embodiment of an implantable device 10 is shown. The implantable device as shown in FIGS. 1-2 can be a monolithic device. As used herein, the term "monolithic" generally means that the device is formed from a single constituent layer or member, which is often referred to as a "core." Thus, the monolithic device generally lacks additional release layers, such as shells, membranes, sheaths, etc., such that the core itself can define an exterior peripheral surface of the device. The implantable device 10 includes a core 40 having a generally circular cross-sectional shape and is elongated so that the resulting device is generally cylindrical in nature. During use of the device 10, a therapeutic agent is capable of being released from the core 40 so that it exits from the outer surface 42 of the implantable device 10.

As shown, the implantable device can have a length (L) and a cross-sectional diameter (D). The length (L) can range from about 2.5 cm to about 7 cm, such as about 3 cm to about 6 cm, such as about 4 cm to about 5 cm. In certain embodiments, the length (L) is about 5 cm. The cross-sectional diameter (D) can range from about 2 mm to about 5 mm, such as from about 3 mm to about 4 mm. In embodiments, the cross-sectional diameter is about 3.5 mm. The device can be sized according to desired therapeutic agent loading and implantation time. For example, for longer lasting implants, the size can be increased such that the implant can be loaded with enough therapeutic agent to last for the life of the implant.

Figure 3:
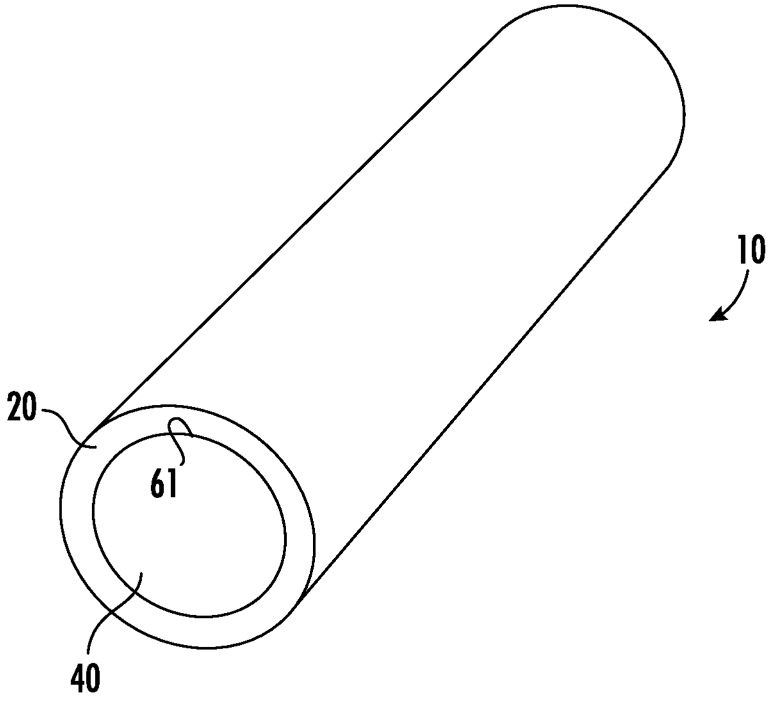
FIG. 3 is a perspective view of one embodiment of the implantable medical device of the present disclosure.
Figure 4:
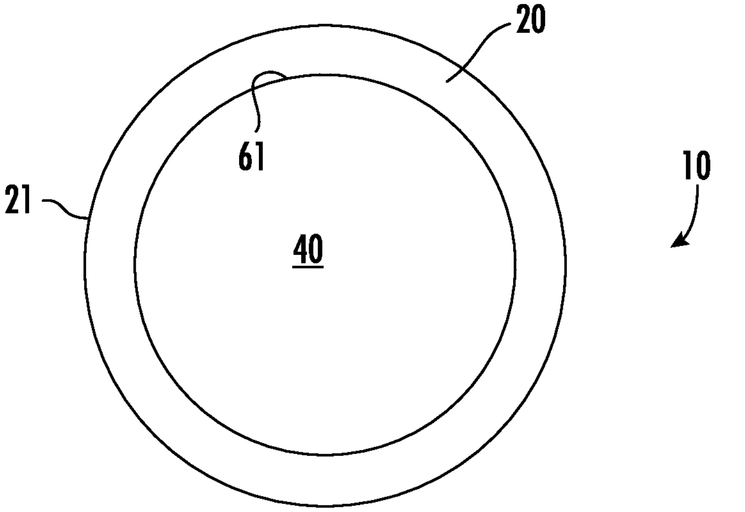
FIG. 4 is a cross-sectional view of the implantable medical device of FIG. 3.

Another embodiment of an implantable device 10 is shown in FIGS. 3-4. The core 40 has a generally circular cross-sectional shape and is elongated so that the resulting device is generally cylindrical in nature. The core 40 defines an outer circumferential surface 61 about which a membrane layer 20 is circumferentially disposed. Similar to the core 40, the membrane layer 20 also has a generally circular cross-sectional shape and is elongated so that it covers the entire length of the core 40. During use of the device 10, a therapeutic agent is capable of being released from the core 40 and through the membrane layer 20 so that it exits from an external surface 21 of the device.

Of course, in other embodiments, the device may contain multiple membrane layers. In the device of FIGS. 3-4, for example, one or more additional membrane layers (not shown) may be disposed over the membrane layer 20 to help further control release of the therapeutic agent. In other embodiments, the device may be configured so that the core is positioned or sandwiched between separate membrane layers.

Figure 5:
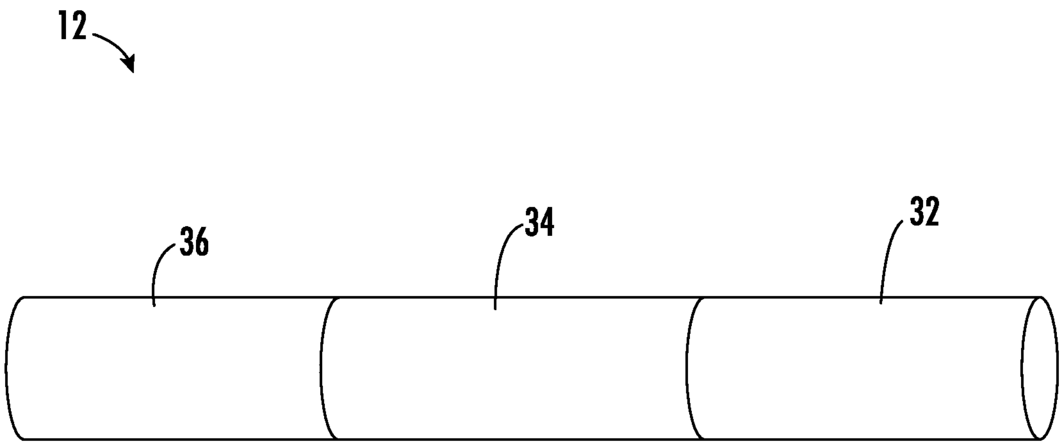
FIG. 5 is a perspective view of one embodiment of the implantable medical device of the present disclosure.

As shown in FIG. 5, the implantable device 12 can include one or more compartments. As shown, the device includes three compartments 32, 34, and 36, however, the disclosure is not so limited. Indeed, two-compartment devices are conceivable in accordance with present disclosure. In fact, any number of compartments or sections can be joined together to form an implantable device as provided herein. As shown, the implantable device 12 includes a first compartment 32, a second compartment 34, and a third compartment 36. Advantageously, the compartments 32, 34, and 36 can each be formulated to contain different amounts of therapeutic agents or different therapeutic agents depending on desired results as will be further discussed hereinbelow. It is also conceivable that the compartments 32, 24, and 36 can be formed from the same core polymer matrix or can each be formed from different core polymer matrix materials. For example, core polymer matrix materials can be modified such that the compartments can have different release rates for therapeutic agents contained therein. Furthermore, any suitable materials can be used or placed between compartments when molding the implantable device.

Additional membrane layers can be added to the implantable device 12 of FIG. 5 as desired (not shown in FIG. 5). For example, in certain embodiments at least one membrane layer can surround the external surface of all compartments 32, 34, 36. In other embodiments, different membrane layers may surround different portions of the compartments 32, 34, and 36. For example, a first membrane can surround the first compartment 32, a second membrane can surround the second compartment 34, and a third membrane can surround the third compartment 36.

Figure 6:
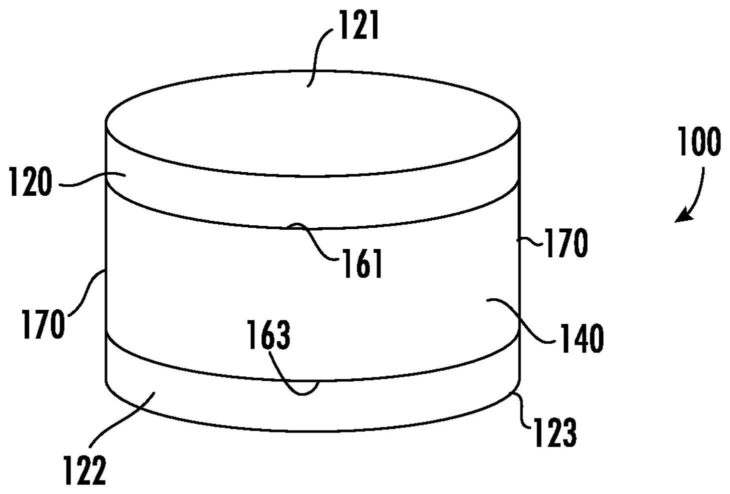
FIG. 6 is a perspective view of another embodiment of the implantable medical device of the present disclosure.
Figure 7:
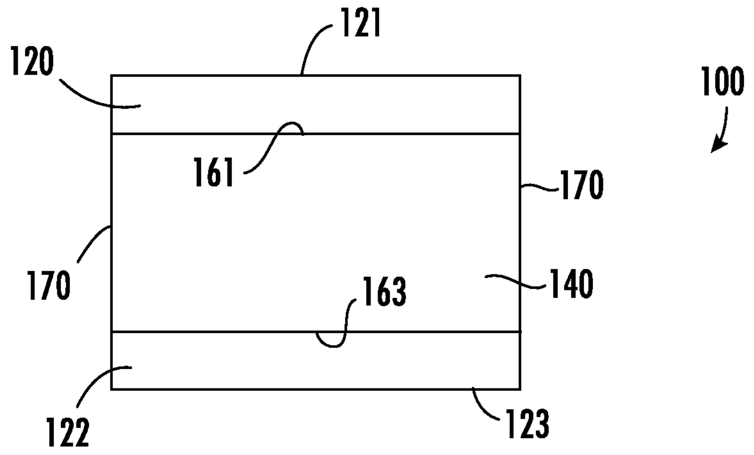
FIG. 7 is a cross-sectional view of the implantable medical device of FIG. 6.

Referring now to FIGS. 6-7, for example, one embodiment of an implantable device 100 is shown that contains a core 140 having a generally circular cross-sectional shape and is elongated so that the resulting device is generally disc-shaped in nature. The core 140 defines an upper outer surface 161 on which is positioned a first membrane layer 120 and a lower outer surface 163 on which is positioned a second membrane layer 122. Similar to the core 140, the first membrane layer 120 and the second membrane layer 122 also have a generally circular cross-sectional shape that generally covers the core 140. If desired, edges of the membrane layers 120 and 122 may also extend beyond the periphery of the core 140 so that they can be sealed together to cover any exposed areas of an external circumferential surface 170 of the core 140. During use of the device 100, a therapeutic agent is capable of being released from the core 140 and through the first membrane layer 120 and second membrane layer 122 so that it exits from external surfaces 121 and 123 of the device. Of course, if desired, one or more additional membrane layers (not shown) may also be disposed over the first membrane layer 120 and/or second membrane layer 122 to help further control release of the therapeutic agent.

In other embodiments, it is contemplated that the device can be contained within a tube, the tube having one or more holes for release of the therapeutic agent. (Not shown in the Figures). The tube material can include any of the polymer materials disclosed herein or can be formed from a metallic material.

V. Use of Device

The implantable device can be effective for sustained release of an antibody over a prolonged period of time such as noted above. Of course, the actual dosage level of the antibody delivered will vary depending on the particular antibody employed and the time period for which it is intended to be released. The dosage level is generally high enough to provide a therapeutically effective amount of the antibody to render a desired therapeutic outcome, i.e., a level or amount effective to reduce or alleviate symptoms of the condition for which it is administered. More particularly, a used herein, the phrase "therapeutically effective amount" means a dose of the therapeutic agent that results in a detectable improvement in one or more symptoms of a disorder, or a dose of antibody that inhibits, prevents, lessens, or delays the progression of a disorder. The exact amount necessary will vary, depending on the subject being treated, the age and general condition of the subject to which the antibody is to be delivered, the capacity of the subject's immune system, the degree of effect desired, the severity of the condition being treated, the particular antibody selected and mode of administration of the composition, among other factors. In one embodiment, for example, a therapeutically effective amount can be from about 0.05 mg to about 5 mg, in some embodiments from about 0.1 mg to about 4 mg, and in some embodiments, from about 0.5 to about 3 mg. The amount of the antibody contained within the individual doses may be expressed in terms of milligrams of drug per kilogram of patient body weight (i.e., mg/kg). For example, the antibody may be administered to a patient at a dose of about 0.0001 to about 10 mg/kg of patient body weight.

The device may be implanted subcutaneously, orally, mucosally, etc., using standard techniques. The delivery route may be intrapulmonary, gastroenteral, subcutaneous, intramuscular, or for introduction into the central nervous system (e.g., intrathecal, intracranial, intraventricular), intraperitoneum or for intraorgan delivery. The device may be placed in a tissue site of a patient in, on, adjacent to, or near a tumor, such as a tumor of the pancreas, biliary system, gallbladder, liver, small bowel, colon, brain, lung, eye, etc.

Specifically, the device may be implanted intratumorally, that is implanted into a tumor. For example, the device can be administered intratumorally, intracancer or post-cancer intratumoral, such as via intracancer puncture. In other embodiments, the drug is administered by intratumoral implantation, peritumoral implantation, or intratumoral implantation after cancer surgery, or via intrathecal implantation. The implantable device of the present disclosure can be implanted into the tumor via any number of procedures currently utilized for brachytherapy. For instance, the implantable device can be placed in a catheter and can be placed in the tumor via placing the catheter in the tumor and releasing the implant from the catheter. Imaging tests (e.g., x-rays, ultrasounds, MRIs, or CT scans) can be utilized to guide or confirm proper placement of the implant in the tumor. Biopsy needles can also be utilized to place the device within the tumor. The implantable device can be placed with guidewires similar to the way that cardiovascular stents and other intravascular devices are placed. Autoinjectors can also be used to place the device. Other devices suitable for implanting devices into tumors of patients can also be utilized to place the implantable device in accordance with this disclosure.

The implantable device of the present disclosure can also be placed during surgical procedures, such as via a laparoscopic procedure or robotic surgery, such as guided robotic surgery. The implantable device can also be inserted by a surgeon with standard hand instruments during a surgical procedure. For example, a surgeon can use tweezers or other suitable devices to implant the device in a tumor during surgery.

The manner in which the device of the present disclosure is implanted within the tumor of a patient may vary as known to those skilled in the art. The route of implantation of the device can depend on a variety of factors, such as the location of the tumor, whether surgery is required, metastasis, tumor size, tumor size, tumor type, patient age, physical condition, fertility status, and any other requirements. For effective therapeutic agent concentration at the site of the tumor, it can be locally administered via intratumoral or peritumoral injection. The device can be implanted prior to or during surgery to remove other tumors, such as tumor resection procedures. The device of the present disclosure can be sized to fit within a needle or other delivery device that can be inserted into the tumor to deliver the device into the tumor.

The implantable device of the disclosure can be directly applied to the cavity formed by the whole or partial resection of the primary or metastatic solid tumor, the tumor surrounding or the tumor body, the residual part of the suspected tumor cell after surgery, or directly placed or injected into or near a primary or metastatic solid tumor that cannot be surgically removed. The implantable device of the present disclosure can be used alone for the treatment of tumors or to prevent postoperative recurrence, or in combination with radiotherapy, immunotherapy (e.g., targeted therapy), and/or chemotherapy.

The implantable device can be effective for sustained release of one or more therapeutic agents (e.g., one or more antibodies) over a prolonged period of time. For example, the implantable device can release an antibody for a time period of about 5 days or more, in some embodiments about 10 days or more, in some embodiments from about 20 days to about 210 days, and in some embodiments, from about 30 days to about 180 days. Further, the present inventors have also discovered that an antibody can be released in a highly controlled manner over the course of the release time period. After a time period of 15 days, for example, the cumulative weight-based release ratio of an antibody may be from about 10% to about 100%, such as from about 20% to about 90%, such as from about 30% to about 80%, such as from about 40% to about 50%. Likewise, after a time period of 35 days, the cumulative weight-based release ratio of an antibody may be from about 20% to about 100%, in some embodiments from about 30% to about 90%, in some embodiments from about 40% to about 80%, such as from about 50% to about 70%, and in some embodiments, from about 35% to about 50%. The "cumulative weight-based release ratio" may be determined by dividing the total amount of therapeutic agent released at a particulate time interval by the total amount of the therapeutic agent initially present, and then multiplying this number by 100. Furthermore, after a time period of 35 days, the cumulative surface area-based release ratio may be from about 5 to about 70 mg/$cm^2$, in some embodiments from about 10 to about 50 mg/$cm^2$, and in some embodiments, from about 15 to about 40 mg/$cm^2$. Likewise, after a time period of 90 days, the cumulative surface area-based release ratio may be from about 15 to about 70 mg/$cm^2$, in some embodiments from about 20 to about 60 mg/$cm^2$, and in some embodiments, from about 30 to about 50 mg/$cm^2$. Furthermore, after a time period of 120 days, the cumulative surface area-based release ratio may be from about 30 to about 70 mg/$cm^2$, in some embodiments from about 35 to about 65 mg/$cm^2$, and in some embodiments, from about 40 to about 50 mg/$cm^2$. The "cumulative surface-based release ratio" may be determined by dividing the amount of therapeutic agent released at a particulate time interval ("mg") by the surface area of the implantable device from which the therapeutic agent can be released ("$cm^2$").

In embodiments, at a time period of about 10 days the implantable device exhibits a cumulative weight-based release ratio of less than 10%. In other embodiments, at a time period of about 20 days, the implantable device exhibits a cumulative weight-based release ratio of less than about 15%. In other embodiments, at a time period of about 40 days, the implantable device exhibits a cumulative weight-based release ratio of less than about 15%. In other embodiments, at a time period of about 60 days, the implantable device exhibits a cumulative weight-based release ratio of less than about 20%. In other embodiments, at a time period of about 80 days, the implantable device exhibits a cumulative weight-based release ratio of less than about 20%. In other embodiments, at a time period of about 90 days, the implantable device exhibits a cumulative weight-based release ratio of less than about 20%. In other embodiments, at a time period of about 100 days, the implantable device exhibits a cumulative weight-based release ratio of less than about 20%. In other embodiments, at a time period of about 120 days, the implantable device exhibits a cumulative weight-based release ratio of less than about 25%.

In other embodiments, however, at a time period of about 20 days, the implantable device exhibits a cumulative weight-based release ratio of less than about 30%, such as from about 20% to about 30%. In still other embodiments, at a time period of about 20 days, the implantable device exhibits a cumulative weight-based release ratio of greater than 50%, such as between about 50% and about 60%. In embodiments, at a time period of about 7 days, the implantable device exhibits a cumulative weight-based release ratio of less than about 10%, such as from about 4% to about 8%. In other embodiments, at a time period of about 14 days, the implantable device exhibits a cumulative weight-based release ratio of less than about 20%, such as from about 14% to about 20%. In other embodiments, at a time period of about 21 days, the implantable device exhibits a cumulative weight-based release ratio of less than about 30%, such as from about 25% to about 30%. In other embodiments, at a time period of about 28 days, the implantable device exhibits a cumulative weight-based release ratio of less than about 40%, such as from about 30% to about 40%. In other embodiments, at a time period of about 60 days, the implantable device exhibits a cumulative weight-based release ratio of less than about 42%, such as from about 38% to about 42%.

The implantable device may be suitable for delivering an antibody to treat a wide variety of conditions, such as cancer, allergies, inflammation, immunologically mediated diseases, metabolic diseases, eye disorders (e.g., angiogenic eye disorders), etc. In one embodiment, the implantable device may release an antibody that can treat cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer. In one specific embodiment, the implantable device may deliver an anti-HER2 antibody to treat a cancer that "overexpresses" a HER receptor. Such cancers include those that have significantly higher levels of a HER receptor, such as HER2, at the cell surface thereof, compared to a noncancerous cell of the same tissue type. Such overexpression may be caused by gene amplification or by increased transcription or translation. If desired, treatment may include a combination of the antibody formulation and a chemotherapeutic agent. The combined administration includes co-administration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, during, or following, administration of the antibody formulation in accordance with the present disclosure. In this embodiment, the timing between at least one administration of the chemotherapeutic agent and at least one administration of the antibody formulation in accordance with the present disclosure is approximately 1 month or less, such as approximately 2 weeks or less. Alternatively, the chemotherapeutic agent and the antibody formulation may be administered concurrently to the patient, in a single formulation or separate formulations.

The implantable device may also be suitable for treatment of an angiogenic eye disorder, which includes any disease of the eye which is caused by or associated with the growth or proliferation of blood vessels or by blood vessel leakage. Non-limiting examples of angiogenic eye disorders that are treatable using the methods of the present disclosure include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV;

e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, and diabetic retinopathies.

The device of the disclosure can be combined with conventional chemotherapy, immunotherapy, hyperthermia therapy, photochemotherapy, electrotherapy, biological therapy, hormone therapy, magnetic therapy, ultrasound therapy, radiotherapy, and gene therapy, etc., so that the anti-tumor or anti-cancer effect is enhanced. Therefore, it can be combined with the above non-surgical treatment at the same time as the local slow release, thereby further enhancing the anticancer effect. When used in combination with the above non-surgical therapies, the device of the present disclosure can be applied simultaneously with non-surgical therapy or can be applied within a few days before the implementation of non-surgical therapy, with the aim of enhancing tumor sensitivity as much as possible. Therefore, it provides a more effective method for eradicating human and animal primary and metastatic solid tumors.

If desired, the implantable device may be sealed within a package (e.g., sterile blister package) prior to use. The materials and manner in which the package is sealed may vary as is known in the art. In one embodiment, for instance, the package may contain a substrate that includes any number of layers desired to achieve the desired level of protective properties, such as 1 or more, in some embodiments from 1 to 4 layers, and in some embodiments, from 1 to 3 layers. Typically, the substrate contains a polymer film, such as those formed from a polyolefin (e.g., ethylene copolymers, propylene copolymers, propylene homopolymers, etc.), polyester (e.g., polyethylene terephthalate, polyethylene naphthalate, polybutylene terephthalate, etc.), vinyl chloride polymer, vinyl chloridine polymer, ionomer, etc., as well as combinations thereof. One or multiple panels of the film may be sealed together (e.g., heat sealed), such as at the peripheral edges, to form a cavity within which the device may be stored. For example, a single film may be folded at one or more points and sealed along its periphery to define the cavity within with the device is located. To use the device, the package may be opened, such as by breaking the seal, and the device may then be removed and implanted into a patient.

The present disclosure may be better understood by the following examples.

Test Methods

Drug Release: The release of a pharmaceutical formulation (e.g., lysozyme) may be determined using an in vitro method. More particularly, implantable device samples may be placed in 150 milliliters of an aqueous PBS buffer solution. The solutions are enclosed in stoppered centrifuge tubes. The flasks are then placed into a temperature-controlled incubator and continuously shaken at 100 rpm. A temperature of 37° C. is maintained through the release experiments to mimic in vivo conditions. Samples are taken in regular time intervals by completely exchanging the aqueous buffer solution. The concentration of an antibody in solution may be determined via UV/Vis absorption spectroscopy using a Cary 3500 split beam instrument. From this data, the amount of the antibody released per sampling interval (microgram per day) may be calculated and plotted over time (day). Further, the cumulative release ratio of the antibody may be calculated as a percentage by dividing the amount of the antibody released at each sampling interval by the total amount of antibody initially present, and then multiplying this number by 100. This percentage is then plotted over time (day).

Examples 1-3

Figure 8:
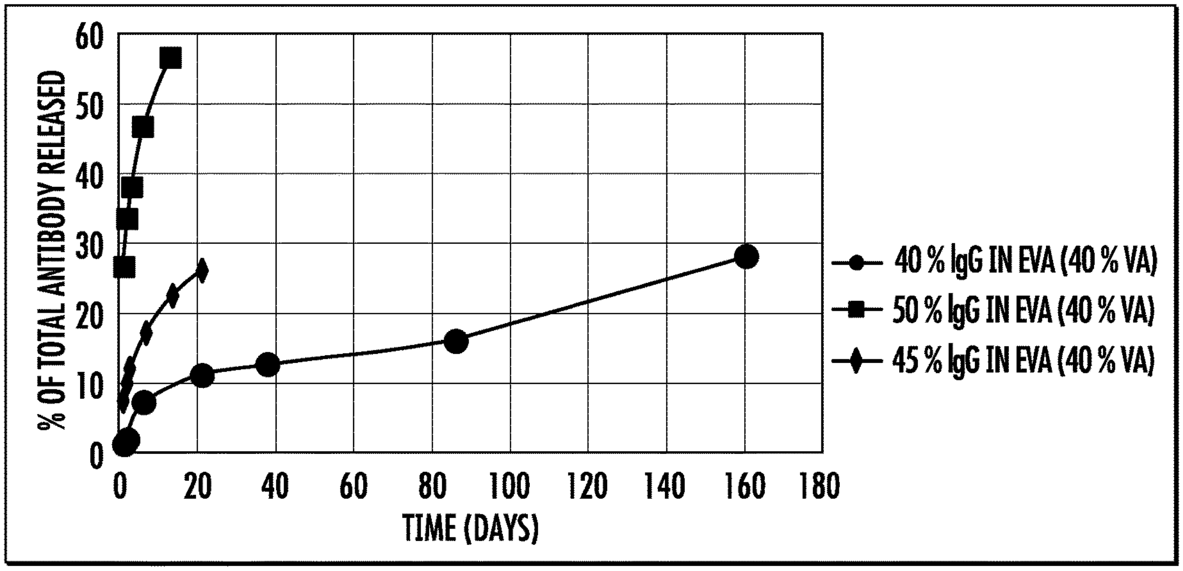
FIG. 8 is a graph showing the cumulative weight-based release percentage of an IgG antibody pharmaceutical formulation versus release time (hours) for Examples 1-3.
Figure 9:
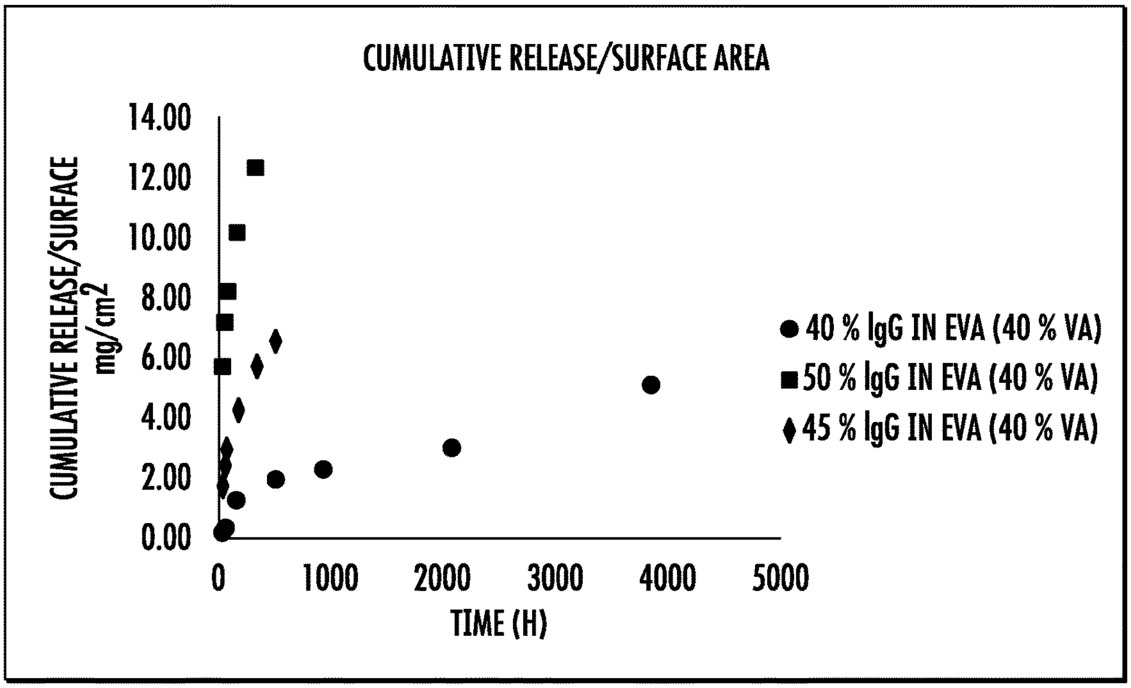
FIG. 9 is a graph showing the cumulative release of the surface area versus time for Examples 1-3.

A rod-shaped monolithic implant containing human plasma derived IgG antibody was produced via extrusion. For Example 1, the device contained 60 wt. % Ateva® 4030AC and 40 wt. % IgG antibody. For Example 2, the device contained 50 wt. % Ateva® 4030AC and 50 wt. % IgG antibody. For Example 3, the device contained 55 wt. % Ateva® 4030AC and 45 wt. % IgG antibody. The devices of Examples 1-3 were formed by melt extruding the components using a 11 mm twin-screw extruder. Extrusion was accomplished using a screw speed of 50 rpm with barrel temperatures set to achieve a nominal melt temperature of 60° C. The rods had a diameter of 3.5 mm and were cut to a length of 3 cm for elution testing. The release of IgG from the rods was measured in PBS buffer in a shaking incubator maintained at 37° C. At regular intervals, the buffer was exchanged with fresh buffer, and the removed buffer characterized using UV-Vis absorbance spectroscopy to measure the concentration of IgG antibody released. The resulting cumulative release rate (%) over 160 days is shown in FIG. 8 and the elution data for Example 1 as expressed in total mass per unit surface area of the sample is shown in FIG. 9. For Example 1, only about 30% of the total antibody was eluted in 160 days. For Example 2, almost 60% of the total antibody was released in less than 20 days. For Example 3, about 25% of the antibody was eluted around day 21. Results for Example 1 are shown in Table 1 below. Results for Example 2 are shown in Table 2 below. Results for Example 3 are shown in Table 3 below

TABLE 1

| Example 1 | | |
|---|---|---|
| Time (Days) | Area normalized release (mg/cm$^2$) | Total % released |
| 1 | 0.25 | 1.37 |
| 2 | 0.37 | 2.04 |
| 6 | 1.30 | 7.09 |
| 21 | 2.04 | 11.13 |
| 38 | 2.34 | 12.76 |
| 86 | 3.00 | 16.37 |
| 160 | 5.16 | 28.13 |

TABLE 2

| Example 2 | | |
|---|---|---|
| Time (Days) | Area normalized release (mg/cm$^2$) | Total % released |
| 1 | 5.77 | 26.67 |
| 2 | 7.27 | 33.52 |
| 3 | 8.28 | 38.15 |
| 6 | 10.20 | 46.94 |
| 13 | 12.38 | 56.87 |

TABLE 3

| Example 3 | | |
|---|---|---|
| Time (Days) | Area normalized release (mg/cm$^2$) | Total % released |
| 1 | 1.81 | 7.07 |
| 2 | 2.50 | 9.78 |
| 3 | 3.03 | 11.87 |
| 7 | 4.37 | 17.12 |
| 14 | 5.76 | 22.54 |
| 21 | 6.65 | 25.94 |

Example 4

A pharmaceutical formulation was initially formed from the following components in Table 4:

TABLE 4

| Component | Concentration (wt. %) |
|---|---|
| Trastuzumab biosimilar (Syd Labs) | 51.3 |
| Trehalose | 46.6 |
| L-Histidine monohydrochloride monohydrate | 1.2 |
| L-Histidine | 0.7 |
| Sorbitan, monododecanoate | 0.2 |

Figure 10:
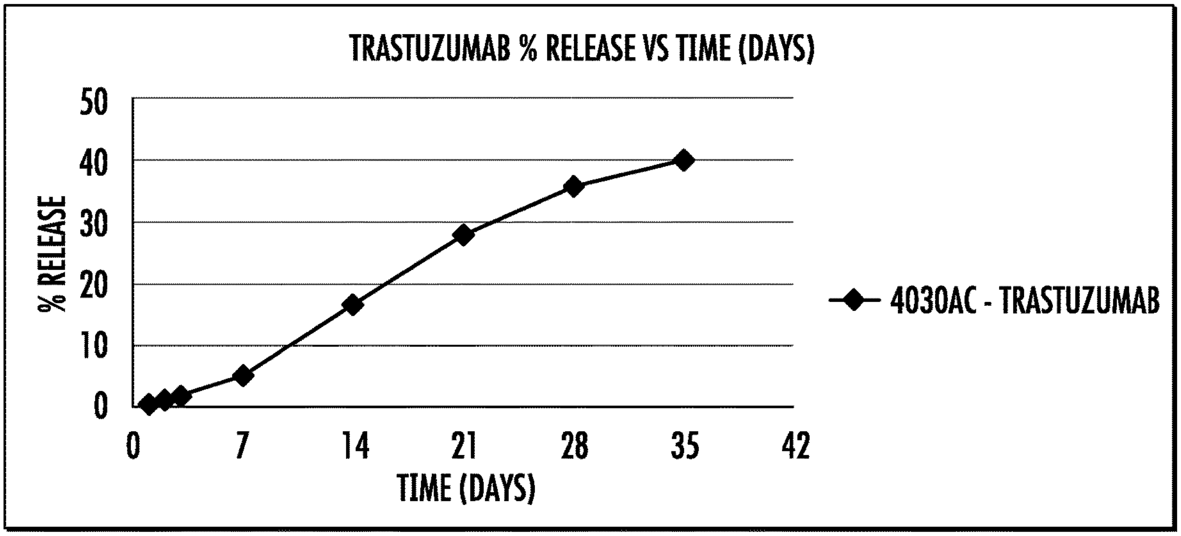
FIG. 10 is a graph showing the cumulative weight-based release percentage of a trastuzumab pharmaceutical formulation versus release time (hours) for Example 4.

To form the formulation, the trastuzumab biosimilar was first lyophilized from an aqueous buffer and then the additional excipients were combined with the antibody to form a solid powder. Once formed, the powder was incorporated into an implantable device so that the resulting device contained 55 wt. % Ateva® 4030AC and 45 wt. % of the trastuzumab powder. The device was formed by melt extruding the components using a 11 mm twin-screw extruder. Extrusion was accomplished using a screw speed of 55 rpm with barrel temperatures set to achieve a nominal melt temperature of 60° C. The rod had a diameter of 3 mm and was cut to a length of 1 cm for elution testing. The release of the trastuzumab biosimilar from the rod was measured in PBS buffer in a shaking incubator maintained at 37° C. At regular intervals, the buffer was exchanged with fresh buffer, and the removed buffer characterized using UV-Vis absorbance spectroscopy to measure the concentration of trastuzumab antibody released. The resulting cumulative release rate (%) over 35 days is shown in FIG. 10. Approximately 40% of the total antibody was released in 35 days.

Results for Example 4 are shown in Table 5 below.

TABLE 5

| Example 4 | | |
|---|---|---|
| Time (Days) | Area normalized release (mg/cm$^2$) | Total % released |
| 1 | 0.310 | 0.340 |
| 2 | 0.440 | 1.123 |
| 3 | 0.544 | 1.751 |
| 7 | 1.13 | 5.29 |
| 14 | 3.02 | 16.77 |
| 21 | 4.87 | 28.00 |
| 28 | 6.15 | 35.78 |
| 35 | 6.86 | 40.16 |
| 42 | 7.27 | 42.64 |
| 49 | 7.57 | 44.44 |
| 56 | 7.81 | 45.95 |
| 63 | 7.95 | 46.80 |
| 77 | 8.07 | 47.53 |

TABLE 5-continued

| Example 4 | | |
|---|---|---|
| Time (Days) | Area normalized release (mg/cm$^2$) | Total % released |
| 84 | 8.18 | 48.18 |
| 91 | 8.29 | 48.84 |
| 98 | 8.42 | 49.65 |
| 105 | 8.53 | 50.35 |
| 112 | 8.63 | 50.96 |
| 119 | 8.74 | 51.67 |
| 126 | 8.87 | 52.47 |
| 140 | 9.10 | 53.86 |
| 154 | 9.30 | 55.11 |
| 182 | 9.58 | 56.81 |

Examples 5-6

Figure 11:
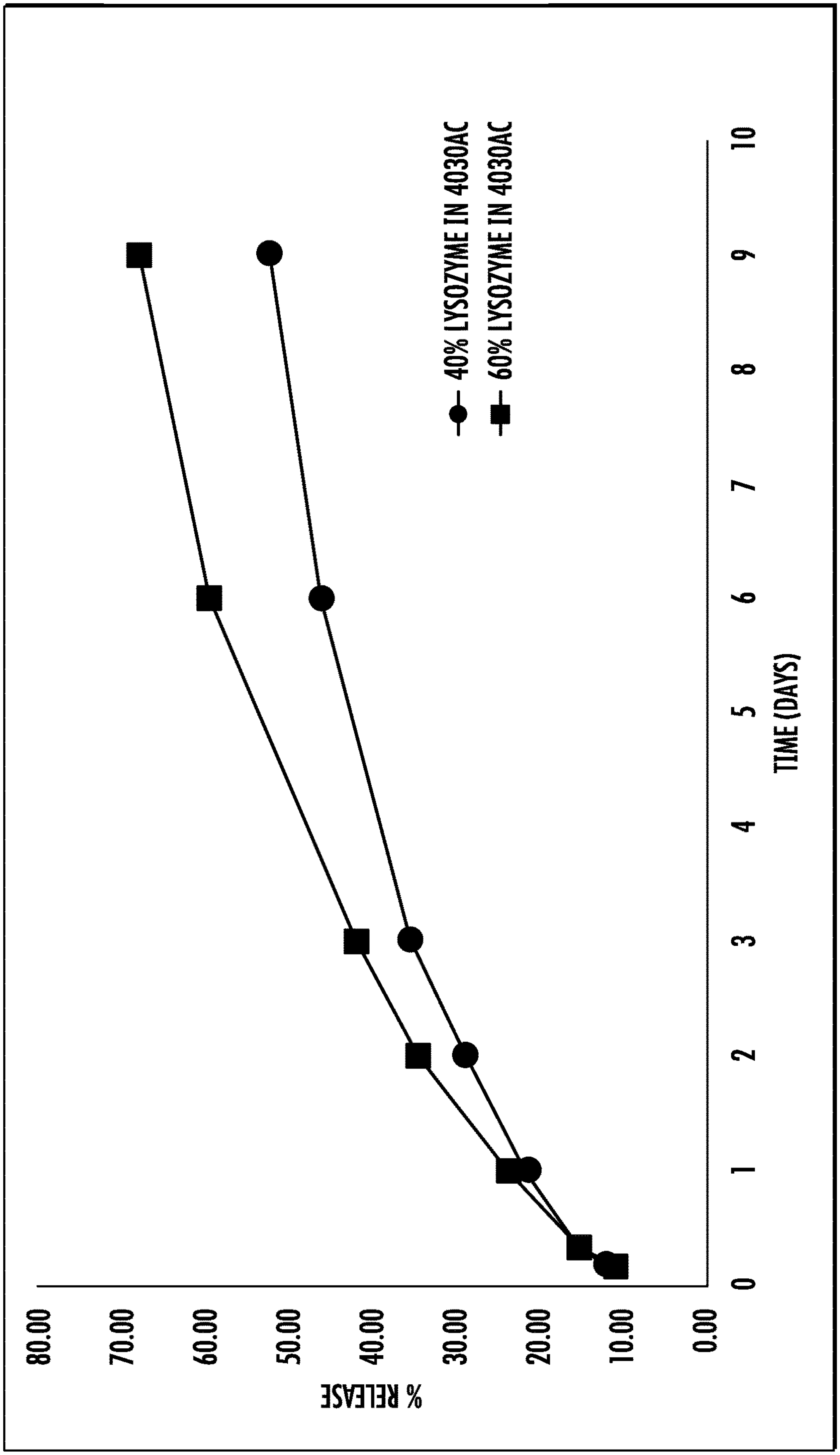
FIG. 11 is a graph showing the cumulative weight-based release percentage of lysozyme versus release time (hours) for Examples 5-6.
Figure 12:
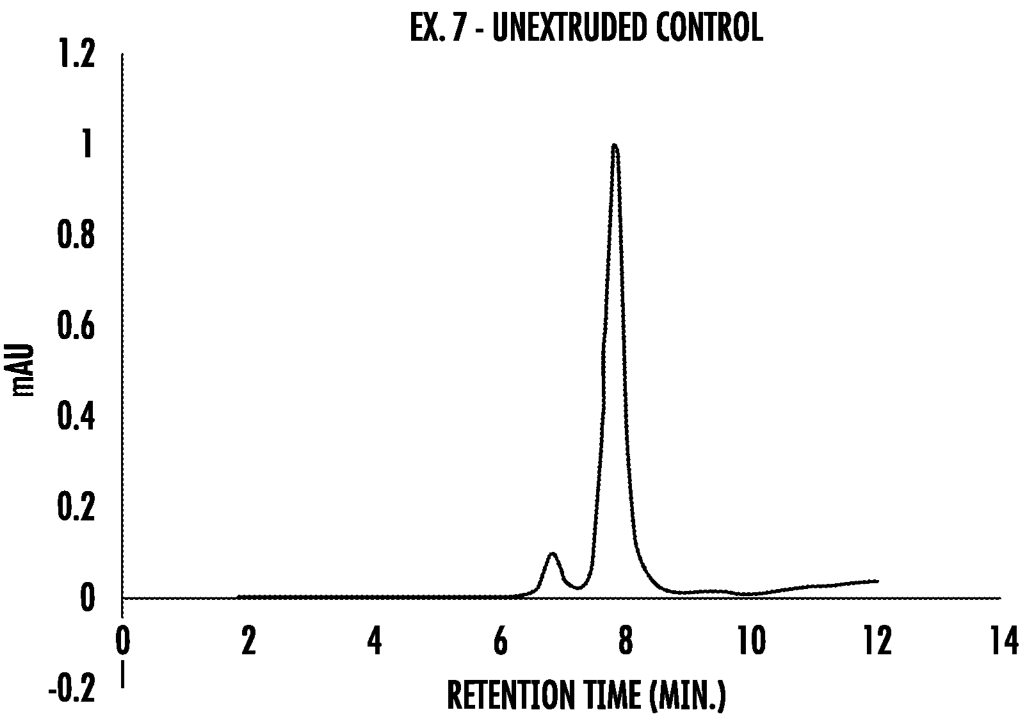
FIG. 12 is an SEC chromatogram for Example 7.
Figure 13:
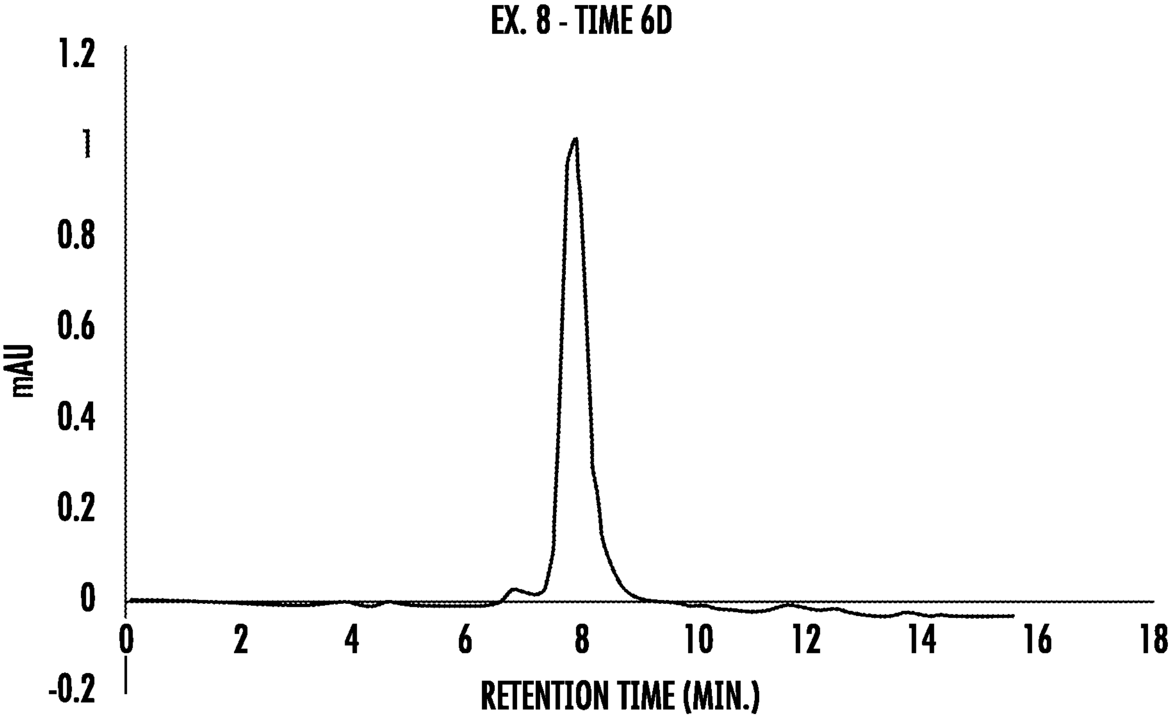
FIG. 13 is an SEC chromatogram for Example 8.
Figure 14:
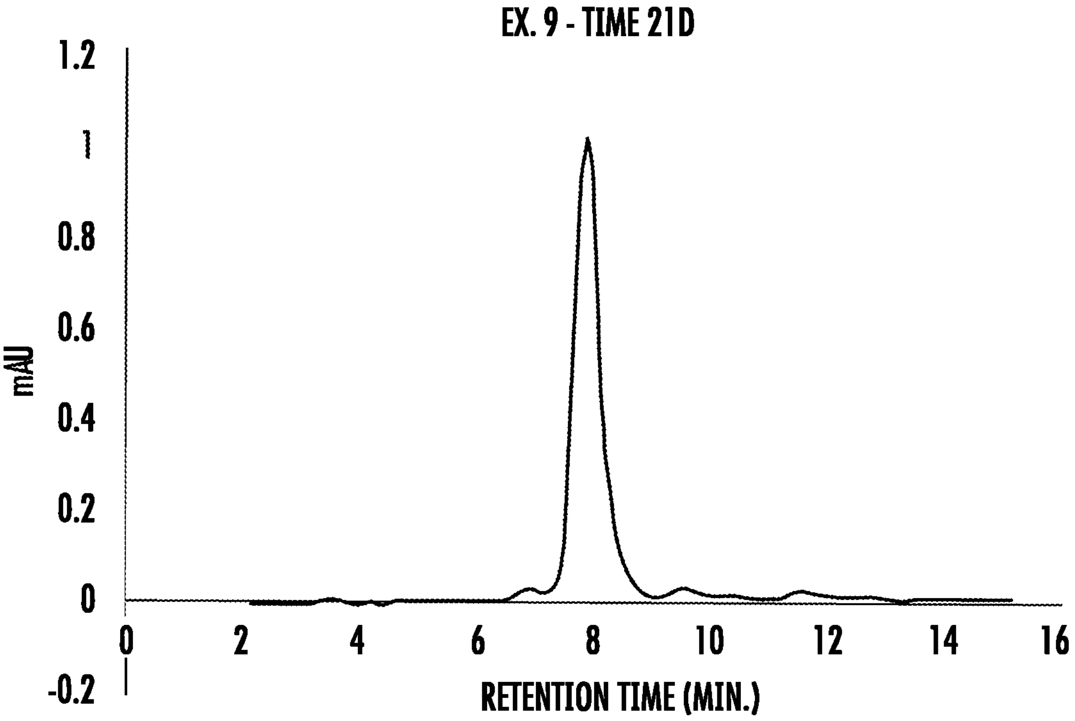
FIG. 14 is an SEC chromatogram for Example 9.
Figure 15:
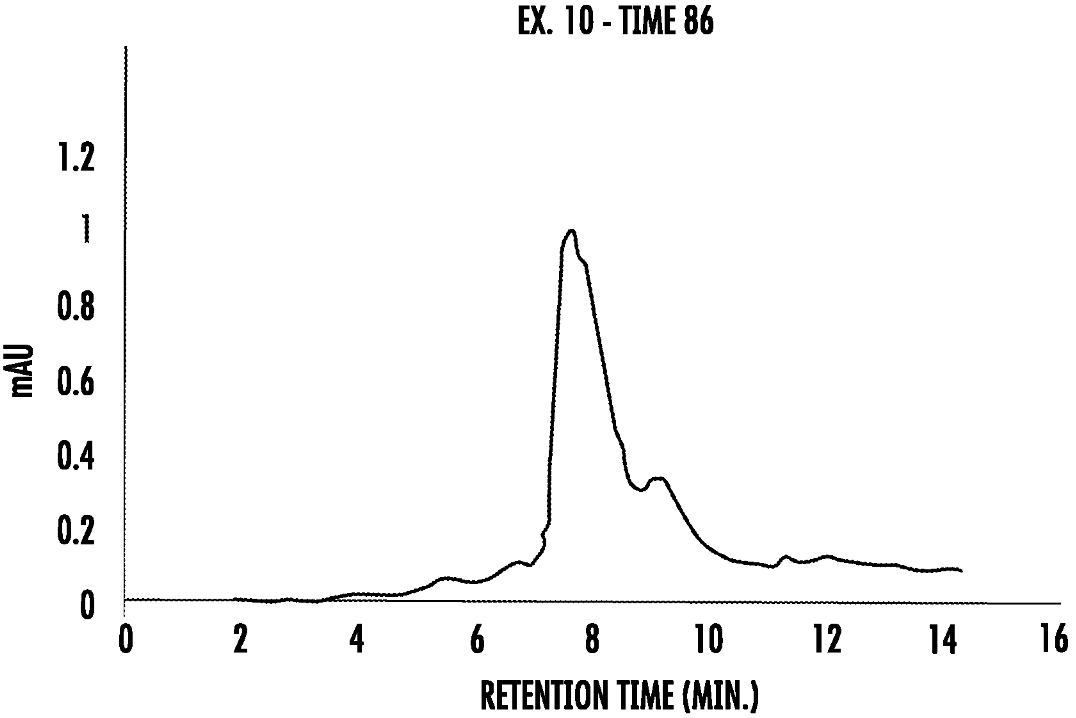
FIG. 15 is an SEC chromatogram for Example 10.
Figure 16:
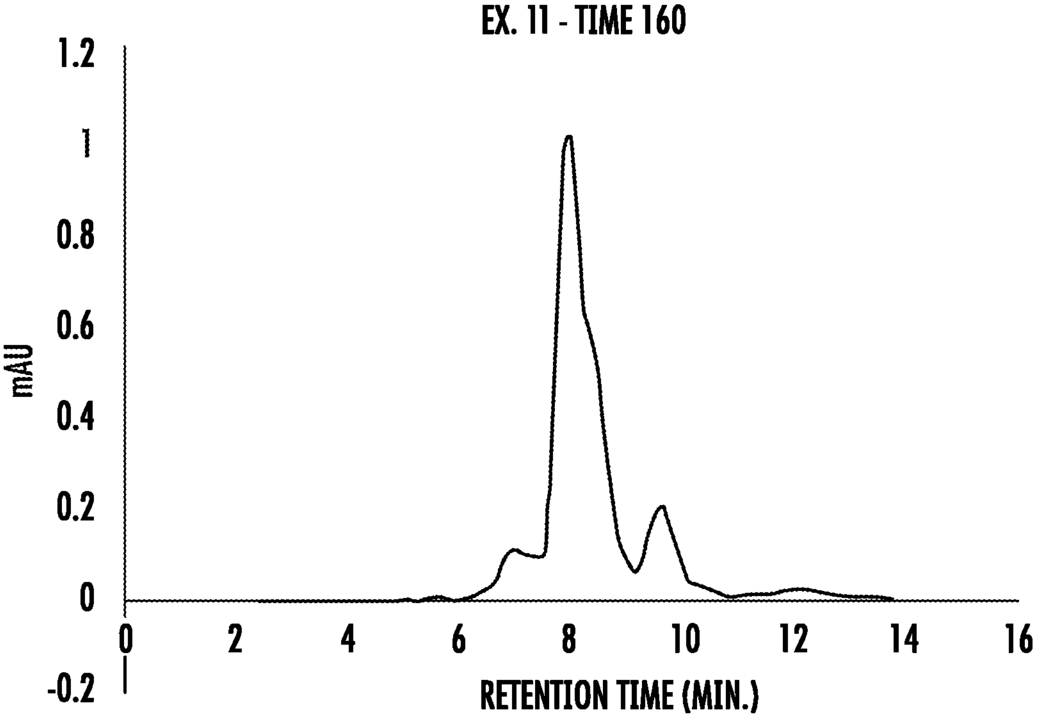
FIG. 16 is an SEC chromatogram for Example 11.

A rod-shaped monolithic implant containing lysozyme was produced via extrusion. For Example 5, the device contained 60 wt. % Ateva® 4030AC and 40 wt. % lysozyme. For Example 6, the device contained 40 wt. % Ateva® 4030AC and 60 wt. % lysozyme. The devices of both examples were formed by melt extruding the components using a 11 mm twin-screw extruder. Extrusion was accomplished using a screw speed of 100 rpm with barrel temperatures set to achieve a nominal melt temperature of 75° C. The rods had a diameter of 3.5 mm and were cut to a length of 3 cm for elution testing. The release of lysozyme from the rods was measured in PBS buffer in a shaking incubator maintained at 37° C. At regular intervals, the buffer was exchanged with fresh buffer, and the removed buffer characterized using UV-Vis absorbance spectroscopy to measure the concentration of lysozyme released. The resulting cumulative release rate (%) over 9 days is shown in FIG. 11. For Example 5, about 50% of the total lysozyme was eluted in 9 days. For Example 6, greater than 60% of the total lysozyme was released in less than 9 days. Results for Examples 5-6 are shown in Tables 6 and 7 below.

TABLE 6

| Example 5 | | |
|---|---|---|
| Time | Area normalized release (mg/cm$^2$) | Total % released |
| 4 hours | 6.11 | 11.98 |
| 8 hours | 7.86 | 15.40 |
| 24 hours | 11.17 | 21.89 |
| 48 hours | 14.79 | 29.00 |
| 72 hours | 18.09 | 35.45 |
| 6 days | 23.46 | 45.99 |
| 9 days | 26.63 | 52.21 |

TABLE 7

| Example 6 | | |
|---|---|---|
| Time (Days) | Area normalized release (mg/cm$^2$) | Total % released |
| 4 hours | 3.52 | 10.87 |
| 8 hours | 4.96 | 15.32 |
| 24 hours | 7.70 | 23.81 |
| 48 hours | 11.17 | 34.54 |
| 72 hours | 13.47 | 41.65 |

TABLE 7-continued

| Example 6 | | |
|---|---|---|
| Time (Days) | Area normalized release (mg/cm$^2$) | Total % released |
| 6 days | 19.21 | 59.39 |
| 9 days | 21.90 | 67.69 |

Examples 7-11

To characterize the protein after drug release, freshly prepared solutions of human-plasma derived IgG antibody as well as solutions collected at selected time points during the elution study described in Example 1 were characterized via size exclusion chromatography (SEC) using an HPLC system equipped with an Agilent AdvanceBio SEC column. Phosphate buffer (0.15 M; pH 7.0) was used as elution media and flow rate was maintained at 1 mL/min. The detection wavelength was set at 280 nm. These samples are described Table 8 below.

TABLE 8

| Example | Description |
|---|---|
| Ex. 7 | Freshly prepared IgG solution (1 mg/ml) |
| Ex. 8 | Solution collected at 6-day time point from Ex. 1 |
| Ex. 9 | Solution collected at 21-day time point from Ex. 1 |
| Ex. 10 | Solution collected at 86-day time point from Ex. 1 |
| Ex. 11 | Solution collected at 160-day time point from Ex. 1 |

The SEC chromatograms are plotted in FIGS. 12-16. Freshly prepared solution (Ex. 7) exhibits a large protein monomer peak (8-minute retention time) as well as a small protein dimer peak (7-minute retention time) (see FIG. 12). At the 6 and 21-day time points (Ex. 8 and Ex. 9) the collected solutions show well defined monomer peaks and small dimer peaks (see FIGS. 13-14). At the 86-day (Ex. 10) and 160-day (Ex. 11) time points significant protein degradation becomes apparent via the introduction of a new peak present at higher retention times (9-minute retention time). Additionally, some protein aggregation is detected in Ex. 10 through the introduction of a small peak at lower retention times (5.5 minutes). (See FIGS. 15-16).

Examples 12-14

Rod shaped core/membrane samples were produced via a core-sheath vacuum compression molding. In the first step, core and membrane compounds were prepared separately via 11 mm twin-screw extruder respectively. Formulations for the core and membranes for Examples 12-14 are shown in Table 9 below.

TABLE 9

| | Core Diameter (2 mm) Length (1 cm) | | Membrane Thickness (0.25 mm) | |
|---|---|---|---|---|
| Example | Ateva ® 4030AC (wt. %) | IgG (wt. %) | Ateva ® 4030 (wt. %) | Mannitol (wt. %) |
| 12 | 40 | 60 | 45 | 55 (Particle size 125 um) |
| 13 | 40 | 60 | 55 | 35 (Particle size 125 um) |
| 14 | 40 | 60 | 55 | 35 (Particle size 75 um) |

Multilayer rods were then formed using a multi-step process via core and membrane vacuum compression molding. To form the membrane, the membrane material was placed in a small chamber, heated, and then compressed into a mold under vacuum at a temperature of 80° C. for 10 minutes, followed by cooling for 2 minutes under vacuum. Multi-layer rod structures were then built up by inserting the core (2 mm) into the membrane followed by heating and compressing the core and membrane under vacuum in the same machine at a temperature of 65° C. for 25 minutes, followed by cooling under vacuum for 5 minutes.

Figure 17:
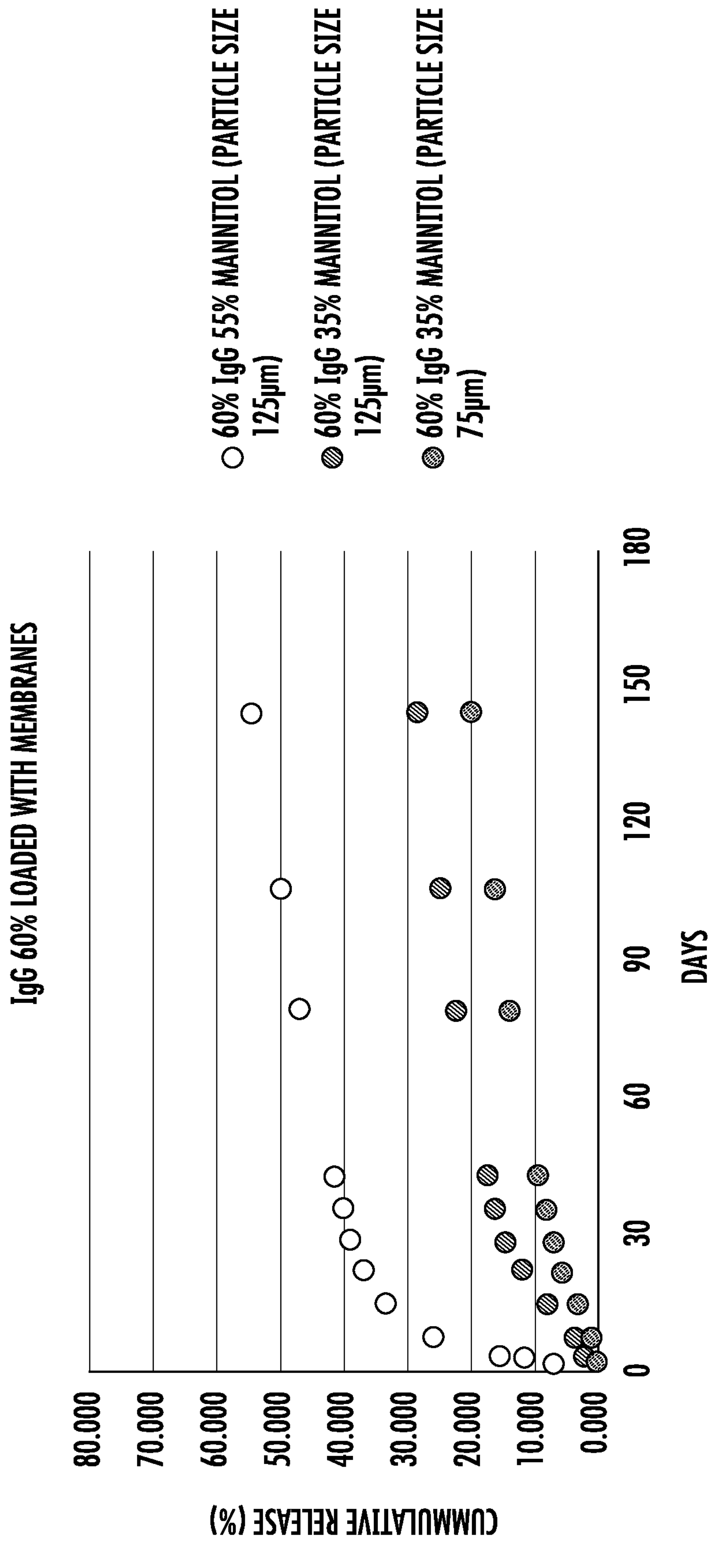
FIG. 17 is a graph showing the cumulative weight-based release percentage of IgG versus release time (Days) for Examples 12-14.

The sealed multi-layer rods were used for elution testing. The release of IgG from these rods into PBS buffer was measured in a shaking incubator maintained at 37° C. At regular intervals, the buffer was exchanged with fresh buffer, and the removed buffer characterized using UV-Vis absorbance spectroscopy to measure the concentration of IgG released. Cumulative release of IgG from Examples 12-14 is shown in FIG. 17. Results for Examples 12-14 are shown in Table 10 below.

TABLE 10

| | % Release Cumulative per Day | | | | | | | | | | | |
|---|---|---|---|---|---|---|---|---|---|---|---|---|
| | Day | | | | | | | | | | | |
| | 1 | 2 | 3 | 7 | 14 | 21 | 28 | 35 | 42 | 79 | 105 | 144 |
| Ex. 12 | 7.3 | 11.5 | 15.4 | 25.9 | 33.3 | 36.7 | 38.8 | 40.3 | 41.5 | 46.8 | 50.2 | 54.1 |
| Ex. 13 | 1.2 | 1.7 | 2.1 | 3.8 | 8.1 | 12.0 | 14.5 | 16.2 | 17.5 | 22.1 | 24.8 | 28.2 |
| Ex. 14 | 0.3 | 0.3 | 0.3 | 1.0 | 2.9 | 5.3 | 7.0 | 8.2 | 9.2 | 13.6 | 16.1 | 19.6 |

These and other modifications and variations of the present disclosure may be practiced by those of ordinary skill in the art, without departing from the spirit and scope of the present disclosure. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed is:

1. An implantable device for intratumoral delivery of a therapeutic agent, comprising:

a polymer matrix within which is dispersed a pharmaceutical formulation that includes one or more therapeutic agents and optionally, one or more excipients, wherein the one or more therapeutic agents comprise one or more antibodies and the polymer matrix contains a hydrophobic polymer, wherein the hydrophobic polymer has a melt flow index of from about 0.2 to about 100 grams per 10 minutes as determined in accordance with ASTM D1238-20 at a temperature of 190° C. and a load of 2.16 kilograms and/or a melting temperature of from about 20° C. to about 70° C. as determined in accordance with ASTM D3418-21, wherein the hydrophobic polymer comprises one or more ethylene vinyl acetate copolymers, wherein the polymer matrix further comprises one or more amino acids, as well as pharmaceutically acceptable salts thereof.

2. The implantable device of claim 1, wherein the weight ratio of the one or more therapeutic agents to the polymer matrix is from about 0.7 to about 2.

3. The implantable device of claim 1, wherein the pharmaceutical formulation constitutes from about 30 wt. % to about 50 wt. % of the device and the polymer matrix constitutes from about 50 wt. % to about 70 wt. % of the device.

4. The implantable device of claim 1, wherein within a time period of 15 days, the device exhibits a cumulative weight-based release ratio of the one or more antibodies of from about 10% to about 55%.

5. The implantable device of claim 1, wherein within a time period of 35 days, the device exhibits a cumulative weight-based release ratio of the antibody of about 20% to about 100%.

6. The implantable device of claim 1, wherein at a time period of about 20 days the device exhibits a cumulative weight-based release ratio of the antibody of less than 15 wt. %.

7. The implantable device of claim 1, wherein the one or more antibodies include an anti-PD-1 antibody, anti-PD-L1 antibody, anti-CLTA-4 antibody, anti-HER2 antibody, anti-VEGF antibody, anti-cKIT antibody, anti-4-1BB antibody, or a combination thereof.

8. The implantable device of claim 1, wherein the one or more antibodies comprise an antibody drug conjugate (ADC).

9. The implantable device of claim 8, wherein the ADC comprises an anti-CLTA-4 antibody linked to one or more chemotherapeutic agents, an anti-PD1 antibody linked to one or more chemotherapeutic agents, an anti-VEGF antibody linked to one or more chemotherapeutic agents, an anti-HER2 antibody linked to one or more chemotherapeutic agents, an anti-cKIT antibody linked to one or more chemotherapeutic agents, and combinations thereof.

10. The implantable device of claim 8, wherein the ADC has a drug-to-antibody ratio (DAR) of from about 0 to 15, such as from about 0 to 8, such as from about 2 to 4.

11. The implantable device of claim 1, wherein the one or more antibodies comprise a multispecific antibody.

12. The implantable device of claim 1, wherein the one or more antibodies comprise an antibody fragment.

13. The implantable device of claim 1, wherein the one or more antibodies comprise an immunocytokine.

14. The implantable device of claim 1, wherein the one or more antibodies comprises an antibody-small interfering RNA (siRNA) conjugate (ARC).

15. The implantable device of claim 1, wherein the therapeutic agent is homogenously dispersed within the polymer matrix.

16. The implantable device of claim 1, comprising one or more membrane layers.

17. The implantable device of claim 16, further comprising a first membrane layer comprises a first membrane polymer matrix containing an ethylene vinyl acetate copolymer.

18. The implantable device of claim 1, wherein the device has a thickness of from about 0.1 to about 10 millimeters and/or a length of from about 1 to about 250 millimeters.

19. A method for prohibiting and/or treating a condition, disease, and/or cosmetic state of a patient, the method comprising implanting the device of claim 1 in a tumor of the patient.

* * * * *